United States Patent
Haraguchi et al.

(10) Patent No.: US 11,207,144 B2
(45) Date of Patent: Dec. 28, 2021

(54) MOTIVE POWER TRANSMISSION ADAPTER AND MEDICAL MANIPULATOR SYSTEM

(71) Applicant: RIVERFIELD INC., Tokyo (JP)

(72) Inventors: Daisuke Haraguchi, Tokyo (JP); Koki Shindo, Tokyo (JP); Hiroki Ujiie, Tokyo (JP)

(73) Assignee: RIVERFIELD INC., Tokyo (JP)

(*) Notice: Subject to any disclaimer, the term of this patent is extended or adjusted under 35 U.S.C. 154(b) by 162 days.

(21) Appl. No.: 16/320,911

(22) PCT Filed: Dec. 15, 2017

(86) PCT No.: PCT/JP2017/045147
§ 371 (c)(1),
(2) Date: Jan. 25, 2019

(87) PCT Pub. No.: WO2018/211730
PCT Pub. Date: Nov. 22, 2018

(65) Prior Publication Data
US 2019/0159853 A1    May 30, 2019

(30) Foreign Application Priority Data

May 16, 2017    (JP) .............................. JP2017-097295

(51) Int. Cl.
*A61B 34/00*    (2016.01)
*B25J 15/04*    (2006.01)
(Continued)

(52) U.S. Cl.
CPC .............. *A61B 34/70* (2016.02); *A61B 34/35* (2016.02); *A61B 34/71* (2016.02); *A61B 46/10* (2016.02);
(Continued)

(58) Field of Classification Search
CPC ......... A61B 34/70; A61B 34/71; A61B 46/10; A61B 90/40; A61B 34/35;
(Continued)

(56) References Cited

U.S. PATENT DOCUMENTS

| | | | |
|---|---|---|---|
| 8,876,805 B2 | 11/2014 | Kaercher et al. | |
| 2006/0052664 A1 | 3/2006 | Julian et al. | |

(Continued)

FOREIGN PATENT DOCUMENTS

| | | |
|---|---|---|
| CN | 106361433 A | 2/2017 |
| EP | 1815950 A1 | 8/2007 |

(Continued)

OTHER PUBLICATIONS

Feb. 20, 2018 International Search Report issued in International Patent Application No. PCT/JP2017/045147.
(Continued)

*Primary Examiner* — Muhammad S Islam
*Assistant Examiner* — Devon A Joseph
(74) *Attorney, Agent, or Firm* — Oliff PLC

(57) ABSTRACT

A motive power transmission adapter includes a casing and at least one power transmission portion. The casing is disposed between a surgical tool and a power unit for driving the surgical tool. In addition, the casing includes a clean surface which is a surface facing the surgical tool disposed in a clean region and an unclean surface which is a surface facing the power unit disposed in an unclean region. At least one power transmission portion is movable relative to the casing and transmits a movement of the drive portion to the driven portion. In addition, at least one power transmission portion is disposed to be movable in a direction in which the clean surface and the unclean surface extend and is disposed (Continued)

BACK ◄──────► FRONT between the drive portion and the driven portion in a direction intersecting a linear motion direction of the drive portion.

25 Claims, 26 Drawing Sheets

(51) Int. Cl.
    *A61B 90/40*     (2016.01)
    *A61B 34/35*     (2016.01)
    *A61B 46/10*     (2016.01)
    *A61B 17/00*     (2006.01)
    *A61B 90/00*     (2016.01)

(52) U.S. Cl.
    CPC ............... *A61B 90/40* (2016.02); *B25J 15/04* (2013.01); *A61B 2017/00017* (2013.01); *A61B 2017/00477* (2013.01); *A61B 2090/065* (2016.02)

(58) Field of Classification Search
    CPC .... A61B 2090/065; A61B 2017/00017; A61B 2017/00477; B25J 2017/00477
    See application file for complete search history.

(56) References Cited

U.S. PATENT DOCUMENTS

| | | | |
|---|---|---|---|
| 2010/0170519 A1* | 7/2010 | Romo | A61B 34/30 128/852 |
| 2012/0059360 A1* | 3/2012 | Namiki | A61B 34/30 606/1 |
| 2013/0172859 A1 | 7/2013 | Kaercher et al. | |
| 2014/0007732 A1* | 1/2014 | Ogawa | A61B 34/37 74/491 |
| 2017/0014998 A1* | 1/2017 | Langenfeld | B25J 9/104 |
| 2017/0027656 A1 | 2/2017 | Robert et al. | |
| 2017/0143438 A1* | 5/2017 | Komuro | A61B 34/37 |
| 2017/0151028 A1 | 6/2017 | Ogawa et al. | |
| 2017/0156807 A1 | 6/2017 | Robert et al. | |
| 2017/0333143 A1* | 11/2017 | Yoshii | A61B 90/11 |
| 2018/0110581 A1* | 4/2018 | Kamata | G02B 7/001 |
| 2018/0228562 A1 | 8/2018 | Robert et al. | |
| 2019/0039241 A1 | 2/2019 | Langenfeld et al. | |
| 2019/0083189 A1* | 3/2019 | Wada | A61B 18/1492 |
| 2019/0192241 A1 | 6/2019 | Xu et al. | |

FOREIGN PATENT DOCUMENTS

| | | |
|---|---|---|
| JP | 2008-519665 A | 6/2008 |
| JP | 2012-213425 A | 11/2012 |
| JP | 5608486 B2 | 10/2014 |
| WO | 2016/098421 A1 | 6/2016 |
| WO | 2016/194263 A1 | 12/2016 |

OTHER PUBLICATIONS

Jul. 5, 2021 Office Action issued in Chinese Patent Application No. 201780047848.1.

Jan. 20, 2021 Extended Search Report issued in European Patent Application No. 1790191.0.

* cited by examiner

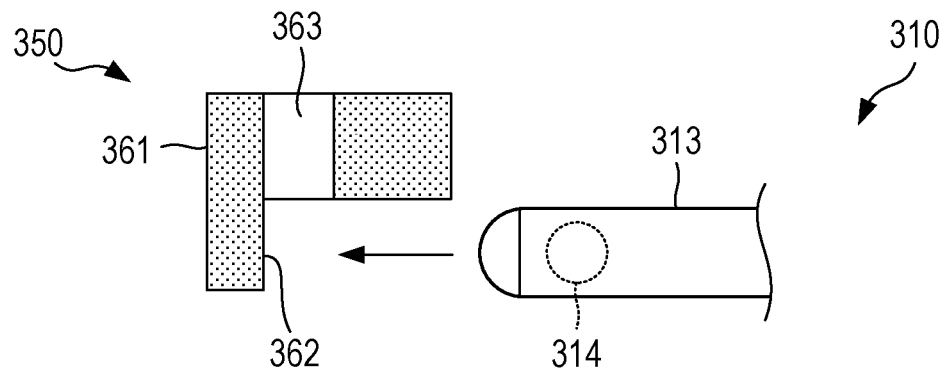
FIG.12A    BACK ←→ FRONT
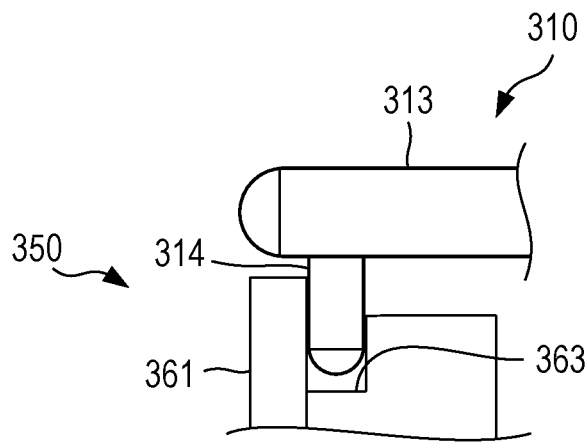
FIG.12B    BACK ←→ FRONT
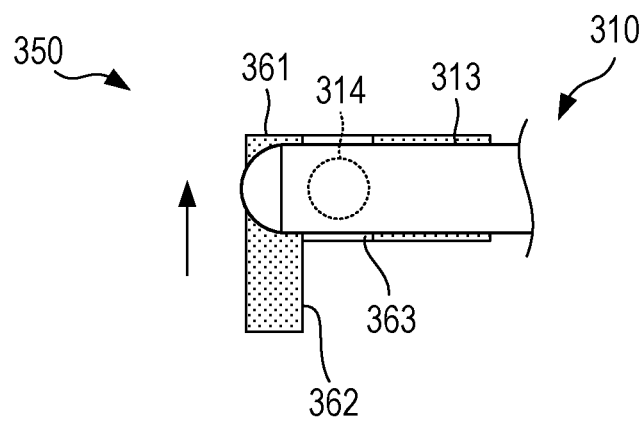
FIG.12C    BACK ←→ FRONT

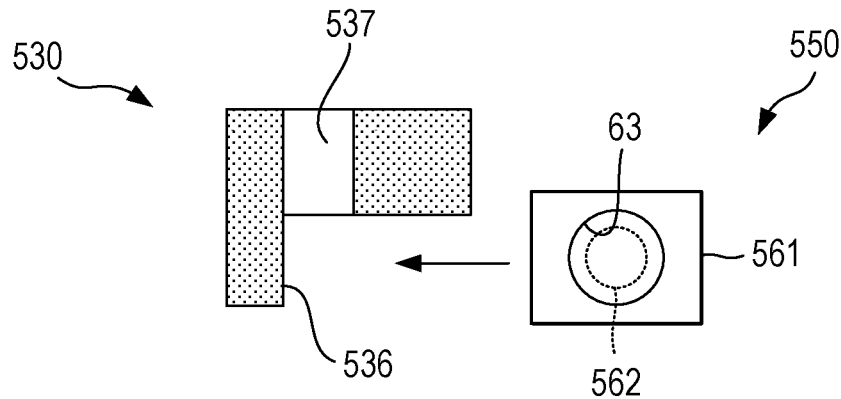
FIG.19A  BACK ⟷ FRONT
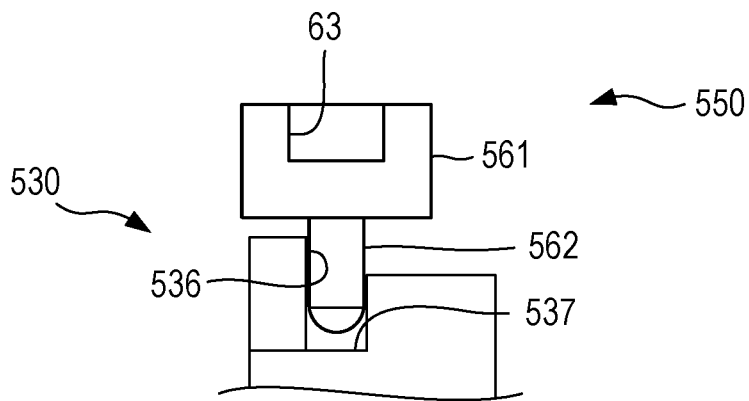
FIG.19B  BACK ⟷ FRONT
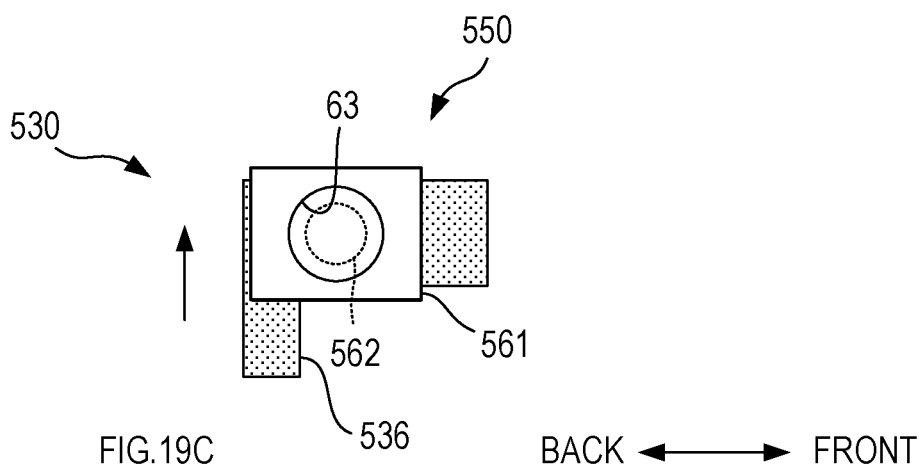
FIG.19C  BACK ⟷ FRONT

MOTIVE POWER TRANSMISSION ADAPTER AND MEDICAL MANIPULATOR SYSTEM

CROSS-REFERENCE TO RELATED APPLICATION

The present international application claims priority based on Japanese Patent Application No. 2017-097295 filed to Japanese Patent Office on May 16, 2017, and the content of Japanese Patent Application No. 2017-097295 is incorporated by reference in its entirety.

TECHNICAL FIELD

The present disclosure relates to a motive power transmission adapter and a medical manipulator system suitable for surgery.

BACKGROUND ART

In recent years, a medical treatment using a robot has been proposed to reduce a burden on an operator or to reduce a labor in medical facilities. For example, in a surgical field, Patent Document 1 discloses a proposal concerning a medical manipulator system in which an operator treats a patient by a multi-degree-of-freedom manipulator having a multi-degree-of-freedom arm which can be remotely controlled.

PRIOR ART DOCUMENT

Patent Document

Patent Document 1: Japanese Patent No. 5608486

SUMMARY OF THE INVENTION

Problems to be Solved by the Invention

A motive power transmission adapter is necessary so as not to contaminate a clean region when a surgical tool is attached or detached during surgery. The surgical tool is frequently replaced during surgery, and thus, it is very important to secure safety and ease of attachment and detachment of the surgical tool. When the motive power transmission adapter disclosed in Patent Document 1 is adopted, problems described below occur.

It is possible to prevent contamination of the clean region using the motive power transmission adapter disclosed in Patent Document 1. However, in a state where the surgical tool is removed from the motive power transmission adapter, a power transmission portion protrudes from an adapter body toward a surgical field in a linear motion direction. An amount of the protrusion of the power transmission portion is changed within a range in which the power transmission portion performs the linear motion.

Accordingly, there is a possibility that the power transmission portion is caught and damaged unexpectedly in a glove of an operator (assistant) who performs a removal work of the surgical tool. There is a concern that a clean portion may be contaminated by the damage of the glove. In addition, due to the glove being caught, a sudden displacement of a robot arm or the surgical tool connected to the power transmission portion may occur, and thus, there is a concern that an instrument position may be forcibly repositioned.

As a countermeasure against this, it is considered that a wall is provided on the adapter body such that an operator's hand does not enter a movable region of the power transmission portion. However, there is a problem that it is difficult to adjust a position of the power transmission portion when the surgical tool is attached due to the provided wall.

In addition, in order to eliminate the need for adjusting the position when the surgical tool is attached, a configuration which biases the power transmission portion to the attachment position using a spring or the like is also considered. However, the power transmission portion is driven and controlled against a biasing force of the spring or the like, and thus, there are problems that a driving force required for the control increases and a size of a power unit increases.

In addition, there is a problem that hysteresis occurs in the driving force due to the biasing force of the spring or the like, which may lead to instability of the surgical tool control. Due to the occurrence of the hysteresis in the driving force, it is difficult to realize a highly accurate force sense detection function which is being considered for introduction to a surgery robot.

Preferably, an aspect of the present disclosure is to provide a motive power transmission adapter and a medical manipulator system capable of suppressing mixture of a clean region and an unclean region and improving ease and safety of attachment and detachment of a surgical tool.

Means for Solving the Problems

A motive power transmission adapter according to a first aspect of the present disclosure includes a casing and at least one power transmission portion. The casing is disposed between a surgical tool and a power unit for driving the surgical tool. In addition, the casing includes a clean surface which is a surface facing the surgical tool disposed in a clean region and an unclean surface which is a surface facing the power unit disposed in an unclean region. At least one power transmission portion is configured to be movable relative to the casing and to transmit a movement of the drive portion to the driven portion. In addition, at least one power transmission portion is disposed to be movable in a direction in which the clean surface and the unclean surface extend, and is disposed between a drive portion which is provided in the power unit and linearly moves and a driven portion which is provided in the surgical tool, in a direction intersecting a linear motion direction of the drive portion.

According to a second aspect of the present disclosure, there is provided a medical manipulator system including: a power unit; a surgical tool; and the motive power transmission adapter according to the first aspect of the present disclosure. The power unit is disposed in an unclean region and includes at least one drive portion driven in a linear motion direction. The surgical tool is disposed in a clean region and includes at least one driven portion which receives a transmission of a driving force from the at least one power transmission portion and is driven.

According to the motive power transmission adapter of the first aspect of the present disclosure and the medical manipulator system of the second aspect of the present disclosure, it is possible to operate at least one driven portion according to a linear motion of at least one drive portion by at least one power transmission portion which moves in the direction in which the clean surface and the unclean surface extend. Therefore, at least one power transmission portion moving into or moving out of the clean region or the unclean region is suppressed, and mixture of the clean region and the unclean region is easily prevented.

In addition, since a movement direction of at least one power transmission portion is the direction in which the clean surface and the unclean surface extend, at least one power transmission portion does not easily protrude from the motive power transmission adapter, and an unexpected interference between an operator's hand (glove) and at least one power transmission portion is easily suppressed. Moreover, at least one power transmission portion does not come into easy contact with an external article, and thus, it is possible to suppress an unexpected movement of at least one power transmission portion generated by the contact with the external article, and when the surgical tool is attached, the position of the at least one power transmission portion is easily adjusted.

In the first aspect of the disclosure, an unclean-side engagement portion configured to engage with or to be disengaged from the drive portion and to transmit a linear motion of the drive portion may be provided in a region of the at least one power transmission portion facing the drive portion. Moreover, a clean-side engagement portion configured to engage with or to be disengaged from the driven portion and to transmit a movement of the at least one power transmission portion to the driven portion may be provided in a region of the at least one power transmission portion facing the driven portion.

In this way, at least one power transmission portion includes the unclean-side engagement portion and the clean-side engagement portion, and thus, at least one power transmission portion and the drive portion can engage with and can be disengaged from each other, and at least one power transmission portion and the driven portion can engage with and can be disengaged from each other. Moreover, a force generated by the linear movement of the drive portion can be transmitted to the driven portion via at least one power transmission portion.

In the first aspect of the disclosure, the casing may include a guide portion configured to extend in the linear motion direction of the drive portion. The at least one power transmission portion may be disposed to be movable relative to the casing along the guide portion.

In this way, at least one power transmission portion includes the guide portion which is disposed to be movable in the linear motion direction, and thus, at least one power transmission portion is prevented from moving in a direction different from the linear motion direction. Accordingly, positioning between at least one power transmission portion and the drive portion can be easily performed, and positioning between at least one power transmission portion and the driven portion can be easily performed.

In the first aspect of the disclosure, the at least one power transmission portion may be a plurality of power transmission portions, and the plurality of power transmission portions may be provided in the casing.

In this way, the plurality of power transmission portions are provided, and thus, it is possible to transmit a plurality of movements to the surgical tool.

In the configuration, the plurality of power transmission portions may be disposed in the casing formed in a flat surface shape including the linear motion direction of the drive portion and may be disposed to be arranged in the direction intersecting the linear motion direction of the drive portion.

In this way, the plurality of power transmission portions are arranged to be disposed on the flat surface, and thus a configuration of the motive power transmission adapter is easily simplified to improve manufacturability of the motive power transmission adapter. Moreover, the plurality of power transmission portions are arranged to be disposed on the flat surface, and thus, in a case where the surgical tool is removed from the plurality of power transmission portions, it is not necessary to move the surgical tool toward a patient present on an extension in the linear motion direction of the drive portion, and it is possible to remove the surgical tool while moving the surgical tool in a lateral direction intersecting the linear motion direction. Accordingly, for example, even in a case where the surgical tool is attached to the motive power transmission adapter so as to be fixed and locked to the motive power transmission adapter, and thereafter, the surgical tool is unexpectedly unlocked and is disconnected from the motive power transmission adapter, the surgical tool falls off in the above-described lateral direction. That is, it is possible to prevent the surgical tool from unexpectedly falling off from the motive power transmission adapter toward the patient.

In the configuration, the casing may be formed in a tubular shape extending in the linear motion direction of the drive portion, one of the power unit and the surgical tool being disposed inside the casing, and the other of the power unit and the surgical tool being disposed outside the casing. In addition, the plurality of power transmission portions may be disposed on a side surface of the casing and may be disposed to be arranged in the direction intersecting the linear motion direction of the drive portion.

In this way, the plurality of power transmission portions are disposed to be arranged on the tubular side surface of the casing, and thus the configuration of the motive power transmission adapter can be easily simplified to improve manufacturability of the motive power transmission adapter. The tubular side surface of the casing may be rephrased as a cylindrical peripheral surface and a polygonal tubular side surface.

In the first aspect of the disclosure, the casing may include a first regulation portion configured to abut against at least one of the surgical tool and the power unit and to regulate a relative movement direction between at least abutting one of the surgical tool and the power unit and the casing in the linear motion direction of the drive portion.

In this way, the first regulation portions is provided, and thus, when at least one of the surgical tool and the power unit is attached to or detached from the motive power transmission adapter, a direction in which at least one of the surgical tool and the power unit moves relative to the motive power transmission adapter is regulated. Accordingly, workability in the attachment and detachment of at least one of the surgical tool and the power unit or safety in surgery is easily improved.

In the first aspect of the disclosure, the at least one power transmission portion may include a first driven abutment surface configured to abut against a driven engagement portion of the driven portion when the surgical tool moves relative to the casing along the linear motion direction and engages with the casing.

In this way, the first driven abutment surface is provided, and thus, when the surgical tool is attached to the motive power transmission adapter, it is possible to regulate the position of the driven portion. Accordingly, at least one power transmission portion and the driven portion easily engage with each other, and thus, workability is easily improved when the surgical tool is attached to the motive power transmission adapter.

In the configuration, the at least one power transmission portion may include a first driven holding portion. The first driven holding portion may be formed to have a length in the direction intersecting the linear motion direction with respect to the first driven abutment surface. Moreover, the first driven holding portion may be configured to regulate a relative movement in the linear motion direction between the driven engagement portion of the driven portion which moves relative to the first driven abutment surface in the intersection direction and the clean-side engagement portion of the at least one power transmission portion.

In this way, the first driven holding portion is provided, and thus, it is possible to transmit a movement in both directions in the linear motion direction between at least one power transmission portion and the driven portion. Since an engagement state between at least one power transmission portion and the driven portion is maintained, controllability of the surgical tool easily increases, and safety is easily secured in surgery.

In the first aspect of the disclosure, the power transmission portion preferably includes a first drive abutment surface which abuts against a drive engagement portion of the drive portion when the power unit moves relative to the casing along the linear motion direction and engages with the casing.

In this way, the first drive abutment surface is provided, and thus, it is possible to regulate the position of the power unit when the power unit is attached to the motive power transmission adapter. Therefore, the power transmission portion and the power unit easily engage with each other, and thus, workability is easily improved when the power unit and the motive power transmission adapter are attached to each other.

In the configuration, the at least one power transmission portion may include a first drive holding portion. The first drive holding portion may be formed to have a length in the direction intersecting the linear motion direction with respect to the first drive abutment surface and may be configured to regulate a relative movement in the linear motion direction between the drive engagement portion of the drive portion which moves relative to the first drive abutment surface in the intersection direction and the unclean-side engagement portion of the at least one power transmission portion.

In this way, the first drive holding portion is provided, and thus, it is possible to transmit a movement in both directions in the linear motion direction between at least one power transmission unit and the drive portion. Since the engagement state between at least one power transmission portion and the drive portion is maintained, controllability of the surgical tool easily increases, and safety is easily secured in surgery.

In the first aspect of the disclosure, the at least one power transmission portion may include a first engagement convex portion configured to engage with at least one of the drive portion and the driven portion and a first elastic portion configured to be elastically deformed by a force applied to the first engagement convex portion.

In this way, the first engagement convex portion and the first elastic portion are provided, and thus, the power unit or the surgical tool is easily attached to the motive power transmission adapter. That is, when the power unit or the surgical tool is attached, the first elastic portion is deformed, and thus, the first engagement convex portion easily engages with the drive portion and the driven portion. Moreover, the first engagement convex portion is pressed onto at least one of the drive portion and the driven portion by a biasing force generated by deformation of the first elastic portion.

In the configuration, the at least one power transmission portion may include a first detection unit configured to detect a movement of the first engagement convex portion by elastic deformation of the first elastic portion.

In this way, the first detection unit is provided, and thus, it is possible to detect the movement of the first engagement convex portion by the elastic deformation of the first elastic portion. Accordingly, when the power unit or the surgical tool is attached, it is possible to detect a movement such as protrusion or retraction of the first engagement convex portion, and the power unit or the surgical tool is reliably attached to the motive power transmission adapter easily.

In the configuration, the first engagement convex portion may include an inclined surface in which a cross-sectional area of the first engagement convex portion increases from a distal end of the first engagement convex portion toward a root thereof.

In this way, the inclined surface is provided in the first engagement convex portion, and thus, compared to a case where the inclined surface is not provided, a gap (rattling) generated when the first engagement convex portion engages with the drive portion or the driven portion is easily suppressed.

In the configuration, the at least one power transmission portion may include a first engagement concave portion configured to engage with at least one of a convex portion provided in the drive portion and a convex portion provided in the driven portion. Moreover, the first engagement concave portion may include an inclined surface in which an opening area of the first engagement concave portion increases from a bottom surface toward an opening.

In this way, the inclined surface is provided in the first engagement concave portion, and thus, compared to a case where the inclined surface is not provided in the first engagement concave portion, a gap (rattling) generated when the first engagement concave portion engages with the drive portion or the driven portion is easily suppressed.

In the second aspect of the disclosure, at least one of the power unit and the surgical tool may include a second regulation portion configured to abut against the casing and regulate a relative movement direction of the abutting casing in a linear motion direction of the at least one drive portion.

In this way, the second regulation portion is provided, and thus, when the motive power transmission adapter is attached to or detached from the power unit or the surgical tool, a direction in which the motive power transmission adapter moves relative to the power unit or the surgical tool is regulated. Therefore, workability in the attachment and detachment of the motive power transmission adapter or safety in surgery is easily improved.

In the second aspect of the disclosure, the at least one drive portion may include a second drive abutment surface configured to abut against a transmission engagement portion of the at least one power transmission portion when the power unit moves relative to the casing along the linear motion direction and engages with the casing.

In this way, the second drive abutment surface is provided, and thus, it is possible to regulate the position of at least one power transmission portion when the motive power transmission adapter is attached to the power unit. Therefore, at least one drive portion and at least one power transmission portion easily engage with each other, and thus, workability is easily improved when the power unit and the motive power transmission adapter are attached to each other.

In the configuration, the at least one drive portion may include a second drive holding portion formed to have a length in the direction intersecting the linear motion direction with respect to the second drive abutment surface and configured to regulate a relative movement in the linear motion direction between the transmission engagement portion which moves relative to the second drive abutment surface in the intersection direction and the at least one drive portion.

In this way, the second drive holding portion is provided, and thus, it is possible to transmit the movement in both directions in the linear motion direction between at least one drive portion and at least one power transmission portion. Since an engagement state between at least one drive portion and at least one power transmission portion is maintained, controllability of the surgical tool easily increases, and safety is easily secured in surgery.

In the second aspect of the disclosure, the at least one driven portion may include a second driven abutment surface which abuts against a transmission engagement portion of the at least one power transmission portion when the surgical tool moves relative to the casing along the linear motion direction and engages with the casing.

In this way, the second driven abutment surface is provided, and thus, it is possible to regulate the position of at least one power transmission portion when the motive power transmission adapter is attached to the surgical tool. Therefore, at least one driven portion and at least one power transmission portion easily engage with each other, and thus, workability is easily improved when the surgical tool and the motive power transmission adapter are attached to each other.

In the configuration, the at least driven portion may include a second driven holding portion formed to have a length in the direction intersecting the linear motion direction with respect to the second driven abutment surface and configured to regulate a relative movement in the linear motion direction between the transmission engagement portion which moves relative to the second driven abutment surface in the intersection direction and the at least one driven portion.

In this way, the second driven holding portion is provided, and thus, it is possible to transmit the movement in both directions in the linear motion direction between at least one driven portion and at least one power transmission portion. Since an engagement state between at least one driven portion and at least one power transmission portion is maintained, controllability of the surgical tool easily increases, and safety is easily secured in surgery.

In the second aspect of the disclosure, at least one of the at least one drive portion and the at least one driven portion includes a second engagement convex portion configured to engage with the at least one power transmission portion and a second elastic portion configured to be elastically deformed by a force applied to the second engagement convex portion.

In this way, the second engagement convex portion and the second elastic portion are provided, and thus, the power unit or the surgical tool is easily attached to the motive power transmission adapter. That is, when the power unit or the surgical tool is attached, the second elastic portion is deformed, and thus, the second engagement convex portion easily engages with the power transmission portion. Moreover, the second engagement convex portion is pressed onto at least one power transmission portion by a biasing force generated by deformation of the second elastic portion.

In the configuration, at least one of the at least one drive portion and the at least one driven portion may include a second detection unit configured to detect a movement of the second engagement convex portion by elastic deformation of the second elastic portion.

In this way, the second detection unit is provided, and thus, it is possible to detect the movement of the second engagement convex portion by the elastic deformation of the second elastic portion. Accordingly, when at least one of the power unit and the surgical tool is attached to the motive power transmission adapter, it is possible to detect a movement such as protrusion or retraction of the second engagement convex portion, and the power unit or the surgical tool is reliably attached to the motive power transmission adapter easily.

In the configuration, the second engagement convex portion may include an inclined surface in which a cross-sectional area of the second engagement convex portion increases from a distal end of the second engagement convex portion toward a root thereof.

In this way, the inclined surface is provided in the second engagement convex portion, and thus, compared to a case where the inclined surface is not provided in the second engagement convex portion, a gap (rattling) generated when the second engagement convex portion engages with the power transmission portion is easily suppressed.

In the configuration, at least one of the at least one drive portion and the at least one driven portion may include a second engagement concave portion configured to engage with a convex portion provided in the at least one power transmission portion. In addition, the second engagement concave portion may include an inclined surface in which an opening area of the second engagement concave portion increases from a bottom surface toward an opening.

In this way, the inclined surface is provided in the second engagement concave portion, and thus, compared to a case where the inclined surface is not provided, a gap (rattling) generated when the second engagement concave portion engages with the power transmission portion is easily suppressed.

In the second aspect of the disclosure, the at least one drive portion may be a plurality of drive portions and the at least one driven portion may be a plurality of driven portions. In addition, the power unit may include the plurality of drive portions, and a plurality of actuator units configured to push the plurality of drive portions in a pushing direction along linear motion directions of the plurality of drive portions and to pull the plurality of drive portions in a pulling direction. In addition, the surgical tool may include the plurality of driven portions corresponding to the plurality of drive portions. In a case where the plurality of driven portions are moved by the plurality of drive portions, one of the drive portions may be moved in one of the pushing direction and the pulling direction by corresponding one of the actuator units so as to move one of the driven portions and at least one of the other drive portions may be biased in one of the pushing direction and the pulling direction by corresponding at least one of the actuator units.

In this way, one drive portion moves in one of the pushing direction and the pulling direction, and at least one of the other drive portions is biased to one of the pushing direction and the pulling direction. Accordingly, a contact state between at least one power transmission portion and at least one driven portion is easily maintained. Specifically, even when an engagement structure between at least one power transmission portion and at least one driven portion is simply configured, the contact state between both can be maintained. Therefore, the surgical tool is easily attached to or detached from the motive power transmission adapter.

According to the motive power transmission adapter and the medical manipulator system of the present disclosure, the linear motion of the drive portion is transmitted to the driven portion by the power transmission portion moving in the direction in which the clean surface and the unclean surface extend. Accordingly, the mixture between the clean region and the unclean region is suppressed, and it is possible to improve ease and safety in attachment and detachment of the surgical tool.

BRIEF DESCRIPTION OF THE DRAWINGS

FIG. 12A is a schematic diagram illustrating a state where a driven engagement portion is separated from a first driven abutment surface, FIG. 12B is a schematic diagram illustrating a state where the driven engagement portion abuts against the first driven abutment surface, and FIG. 12C is a schematic diagram illustrating a state where the driven engagement portion is held by a first driven holding portion.

FIG. 19A is a schematic diagram illustrating a state in which a transmission engagement portion is separated from a second drive abutment surface, FIG. 19B is a schematic diagram illustrating a state where the transmission engagement portion abuts against the second drive abutment surface, and FIG. 19C is a schematic diagram illustrating a state in which the transmission engagement portion is held by a second drive holding portion.

Figure 1:
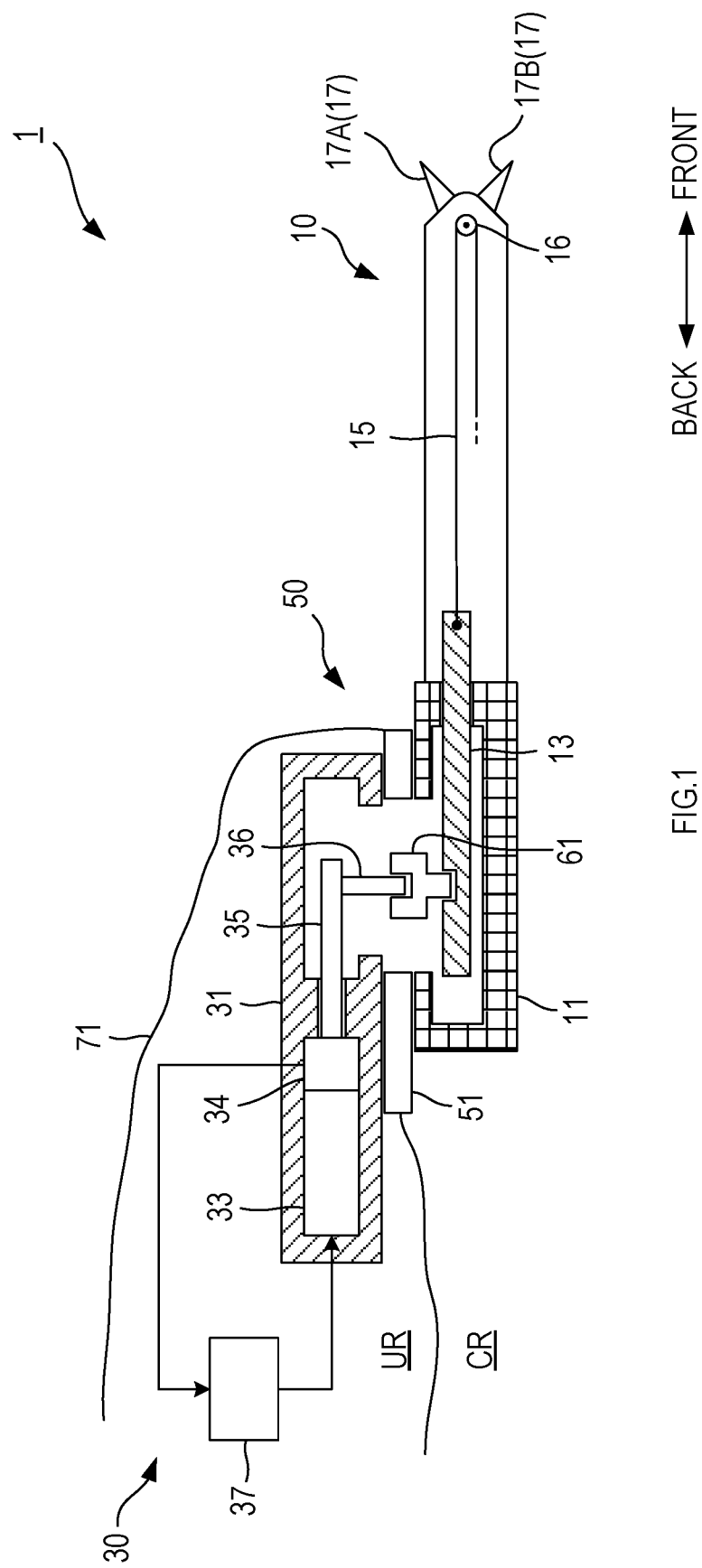
FIG. 1 is a schematic diagram illustrating a configuration of a medical manipulator according to a first embodiment of the present disclosure.

EXPLANATION OF REFERENCE NUMERALS 1, 101, 201, 301, 401, 501, 601, 701, 701A, 701B, 701C, 701D, 701E, 701F, 801, 901: medical manipulator system, 50, 150, 250, 350, 450, 550, 650, 750, 750A, 750B, 750C, 750D, 750E, 750F, 850: motive power transmission adapter, 10, 110, 210, 310, 410, 710F, 810, 910: surgical tool, 13, 313, 413, 813A, 813B, 913A, 913B: driven portion, 14, 314: driven-side engagement portion, 30, 130, 230, 530, 630, 730, 730A, 730B, 730C, 830: power unit, 35, 535, 835A, 835B: drive portion, 36: drive-side engagement portion, 51: casing, 52: clean surface, 53: unclean surface, 54: clean surface slit (guide portion), 61, 361, 561, 661: power transmission portion, 112: second surgical tool regulation portion (second regulation portion), 132: second power regulation portion (second regulation portion), 152: first surgical tool regulation portion (first regulation portion), 153: first power regulation portion (first regulation portion), 254: guide portion, 362: first driven abutment surface, 363: first driven holding portion, 414: second driven abutment surface, 415: second driven holding portion, 462: transmission engagement portion, 536: second drive abutment surface, 562: transmission engagement portion, 636: drive engagement portion, 662: first drive abutment surface, 663: first drive holding portion, 762, 762A, 762B, 762E: clean-side engagement portion (first engagement convex portion), 763, 763A, 763B: first elastic portion, 736, 736A, 736B, 736E: drive-side engagement portion (second engagement convex portion), 737, 737A, 737B: second elastic portion, 765C, 765D: first detection unit, 738E: second inclined surface, 739C, 739D: second detection unit, 714F: driven-side engagement portion (second engagement concave portion), 715F: second inclined surface, 763F: unclean-side engagement portion (first engagement concave portion), 764F: first inclined surface, 833A, 833B: actuator unit

MODE FOR CARRYING OUT THE INVENTION

[First Embodiment]

Figure 2:
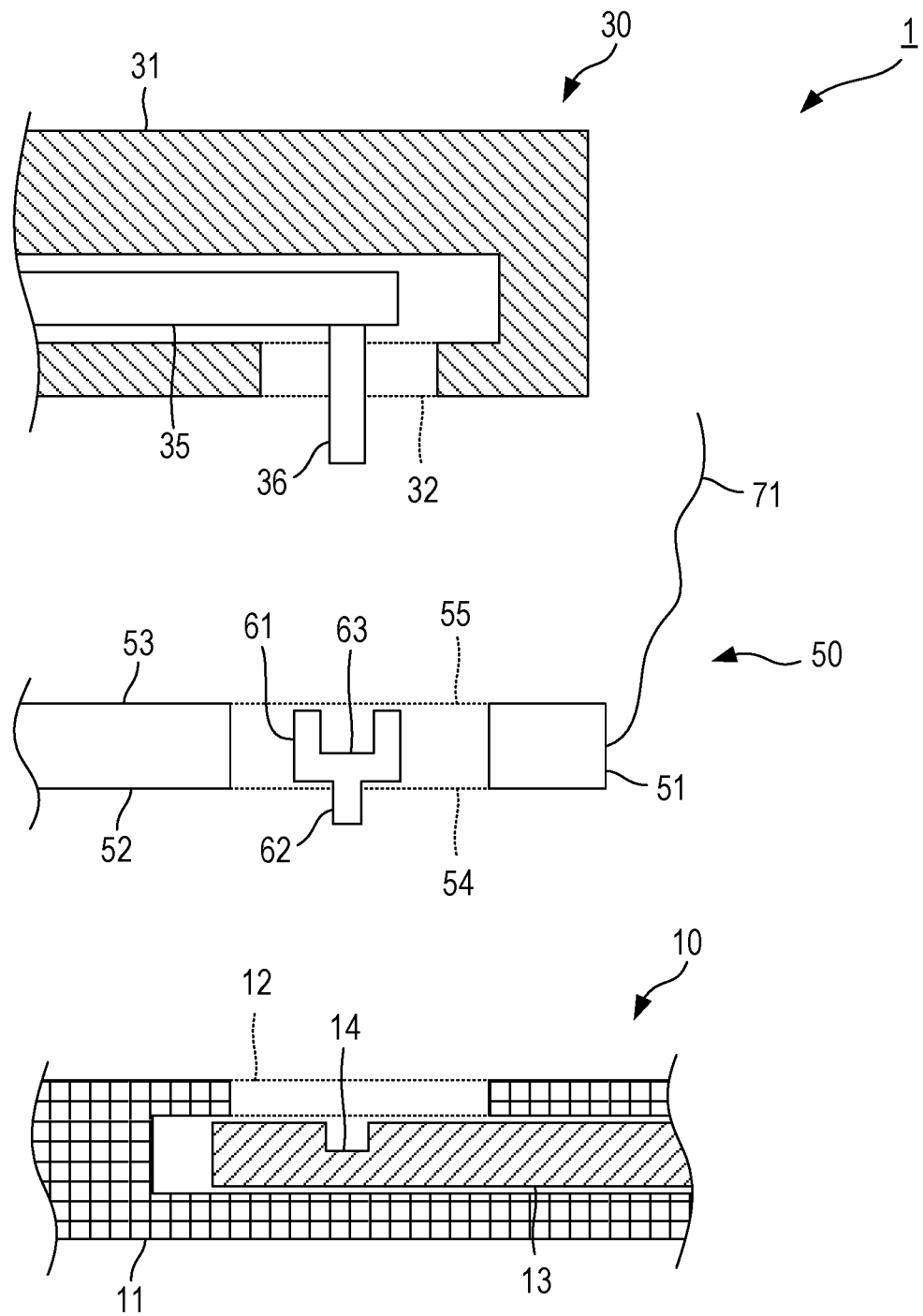
FIG. 2 is a partially enlarged diagram illustrating a configuration around a motive power transmission adapter of FIG. 1.

Hereinafter, a medical manipulator system 1 and a motive power transmission adapter 50 according to a first embodiment of the present disclosure will be described with reference to FIG. 1 and FIG. 2. In the first embodiment, the medical manipulator system 1 for treating a patient in a surgical field and the motive power transmission adapter 50 used in the medical manipulator system 1 will be described. As shown in FIG. 1, the medical manipulator system 1 includes a surgical tool 10, a power unit 30, and the motive power transmission adapter 50.

The surgical tool 10 is used to treat a patient in the medical manipulator system 1 and is disposed in a clean region CR. As shown in FIGS. 1 and 2, the surgical tool 10 includes a surgical tool casing 11, a driven portion 13, a wire 15, a drive pulley 16, and a forceps 17.

The surgical tool casing 11 has a shape which extends in a front-rear direction (hereinafter, referred to as a "linear motion direction"). In addition, the driven portion 13, the wire 15, and the drive pulley 16 are accommodated inside the surgical tool casing 11, and the surgical tool casing 11 supports the forceps 17.

A rear portion which is a portion on the power unit 30 side (rear side) in the surgical tool casing 11 is formed in a plate shape which extends in the front-rear direction and a right-left direction (a direction perpendicular to a paper surface of FIG. 1) and is attached to the motive power transmission adapter 50. The driven portion 13 is disposed inside the rear portion of the surgical tool casing 11. In the first embodiment, an example in which six driven portions 13 are disposed to be arranged in the right-left direction is described.

A surgical tool slit 12 formed in a groove shape extending in the linear motion direction is provided in a region in which the driven portion 13 is disposed on a surface facing the motive power transmission adapter 50 in the rear portion of the surgical tool casing 11. That is, six surgical tool slits 12 are disposed to be arranged in the right-left direction.

A front portion which is a portion extending forward from the rear portion of the surgical tool casing 11 is a rod-shaped portion extending in the linear motion direction. A space in which the wire 15 extends in the linear motion direction and is disposed is provided inside the front portion of the surgical tool casing 11. The drive pulley 16 and the forceps 17 are disposed on a front end portion of the surgical tool casing 11.

The driven portion 13 is a member which is formed in a columnar shape extending in the front-rear direction. The driven portion 13 is disposed to be linearly movable in the front-rear direction in an internal space which is formed in the rear portion of the surgical tool casing 11. A driven-side engagement portion 14 formed in a concave shape to be able to engage and disengage with a clean-side engagement portion 62 of a power transmission portion 61 is provided on a side surface on a rear side of the driven portion 13.

The driven-side engagement portion 14 is formed in a concave shape on a side surface of the driven portion 13 facing the motive power transmission adapter 50. In other words, the driven-side engagement portion 14 is formed on a side surface of the driven portion 13 facing the surgical tool slit 12.

The wire 15 is a member which is formed in a string shape, is disposed in an internal space provided in the front portion of the surgical tool casing 11, and transmits a movement of the driven portion 13 to the forceps 17. A different driven portion 13 is attached to each of end portions of the wire 15.

The drive pulley 16 is a disk or a columnar member which is rotatably supported around a rotation axis. In addition, the drive pulley 16 is disposed on a front end in the front portion of the surgical tool casing 11 and a movable piece 17A of the forceps 17 (described later) is fixed to the drive pulley 16.

The forceps 17 is disposed on a front end of the surgical tool casing 11 and is used as a treatment tool in surgery. The forceps 17 includes the movable piece 17A which is fixed to the drive pulley 16 and whose movement is controlled by a rotation of the drive pulley 16 and a fixed piece 17B which is fixed to the surgical tool casing 11. In the forceps 17, the movement of the movable piece 17A is controlled, and thus, an object is interposed between the movable piece 17A and the fixed piece 17B.

Moreover, in the first embodiment, the example in which the forceps 17 includes the movable piece 17A and the fixed piece 17B is described. However, the forceps 17 may include two movable pieces 17A. In this case, a group of the driven portion 13, the wire 15, and the drive pulley 16 for moving one movable piece 17A and a group of a driven portion 13, a wire 15, and a drive pulley 16 for moving the other movable piece 17A may be provided.

Moreover, in the first embodiment, the example in which the forceps 17 serving as the treatment tool is provided in the surgical tool 10 and a patient is treated using the forceps 17 is described. However, a tool other than the forceps 17 may be as a treatment tool used in the surgical tool 10.

The power unit 30 generates power for moving the forceps 17 of the surgical tool 10 and controls the movement of the forceps 17. Moreover, the power unit 30 is disposed in an unclean region UR. As shown in FIGS. 1 and 2, the power unit 30 includes a power unit casing 31, an actuator unit 33, a detection unit 34, a drive portion 35, and a control unit 37. In addition, a position sensor (not shown) which detects a position of the drive portion 35 is also provided in the power unit 30.

The actuator unit 33 and the detection unit 34 are accommodated inside the power unit casing 31, and the drive portion 35 is supported by the power unit casing 31 so as to be linearly movable in the front-rear direction. Moreover, a region in which the motive power transmission adapter 50 can be attached and detached on a surface extending in the front-rear direction and the right-left direction is formed in front of the power unit casing 31.

The drive portion 35 is disposed inside the front portion of the power unit casing 31. Moreover, the actuator unit 33 and the detection unit 34 are disposed in the rear portion of the power unit casing 31. In the first embodiment, an example in which six sets of the drive portions 35, the actuator units 33, and the detection units 34 are disposed to be arranged in the right-left direction is described.

A power unit slit 32 which is formed in a groove shape extending in the linear motion direction is provided in a region in which the drive portion 35 is disposed on a surface of the power unit casing 31 facing the motive power transmission adapter 50. That is, six power unit slits 32 are disposed to be arranged in the right-left direction.

Based on a control signal output from the control unit 37, the actuator unit 33 generates a force which linearly moves the drive portion 35 in the front-rear direction. In the first embodiment, an example in which the actuator unit 33 is driven by an air pressure is described. However, the actuator unit 33 may be an actuator driven by an electromagnetic force or may be an actuator driven by other known driving methods.

The detection unit 34 is a sensor which detects a force applied in a direction along the front-rear direction in a force applied to the drive portion 35 from the outside of the medical manipulator system 1. A portion between the detection unit 34 and the control unit 37 is configured such that a signal related to the force detected by the detection unit 34 is transmitted to the control unit 37. In addition, the method and the configuration for detecting the force by the detection unit 34 can use any known method and configuration, and are not particularly limited. Moreover, the detection unit 34 may be disposed inside the power unit casing 31 or may be disposed inside the control unit 37.

The drive portion 35 is disposed inside the power unit casing 31 which is formed in a rod shape extending in the front-rear direction. The drive portion 35 is linearly moved in the front-rear direction by the actuator unit 33. A drive-side engagement portion 36 which engages with an unclean-side engagement portion 63 of the power transmission portion 61 and is formed in a rod shape is provided on a front side surface of the drive portion 35.

The drive-side engagement portion 36 is formed in a rod shape protruding toward the motive power transmission adapter 50 on a side surface of the drive portion 35 facing the motive power transmission adapter 50. In other words, the drive-side engagement portion 36 is formed on the side surface of the drive portion 35 facing the power unit slit 32.

The control unit 37 generates a control signal which controls a movement of the actuator unit 33 based on an operation input of the operator and outputs the generated control signal to the actuator unit 33. Moreover, a signal related to the force output from the detection unit 34 is input to the control unit 37. The control unit 37 generates a control signal for controlling the movement of the actuator unit 33 based on the signal related to the input force, or sends a signal to an operation unit (not shown) operated by the operator so as to provide information of the force applied to the surgical tool 10 to the operator.

The motive power transmission adapter 50 is disposed between the surgical tool 10 and the power unit 30 which drives the surgical tool 10. The motive power transmission adapter 50 transmits the driving force generated by the power unit 30 to the surgical tool 10. In addition, the motive power transmission adapter 50 partitions the clean region CR where the surgical tool 10 is disposed and the unclean region UR where the power unit 30 is disposed. The motive power transmission adapter 50 includes at least a casing 51, a power transmission portion 61, and a drape 71.

The casing 51 constitutes an outer shape of the motive power transmission adapter 50, and the power transmission portion 61 is disposed inside the casing 51. The casing 51 includes a clean surface 52 and an unclean surface 53. The clean surface 52 is a surface facing the surgical tool 10 disposed in the clean region CR and is a surface to which the surgical tool 10 is attached. The unclean surface 53 is a surface facing the power unit 30 disposed in the unclean region UR and is a surface to which the power unit is attached.

In the clean surface 52, a clean surface slit 54 which is formed in a groove shape extending in the linear motion direction is provided in a region facing the surgical tool slit 12 of the surgical tool 10. In addition, in the unclean surface 53, an unclean surface slit 55 formed in a groove shape extending in the linear motion direction is provided in a region facing the power unit slit 32 of the power unit 30.

In the first embodiment, similarly to the surgical tool slit 12 and the power unit slit 32, an example in which six clean surface slits 54 and six unclean surface slits 55 are disposed to be arranged in the right-left direction is described.

The power transmission portion 61 is disposed in a region interposed between the clean surface slit 54 and the unclean surface slit 55 inside the casing 51. The power transmission portion 61 is movable relative to the casing 51 in the linear motion direction. The linear motion direction is a direction in which the clean surface 52 and the unclean surface 53 extend.

In addition, the power transmission portion 61 transmits the driving force from the drive portion 35 of the power unit 30 to the driven portion 13 of the surgical tool 10. In the first embodiment, an example is described in which six power transmission portions 61 are disposed in the region interposed between the clean surface slit 54 and the unclean surface slit 55.

The clean-side engagement portion 62 is provided on the clean surface 52 side of the power transmission portion 61. The unclean-side engagement portion 63 is provided on the unclean surface 53 side of the power transmission portion 61. The clean-side engagement portion 62 is a rod-shaped portion which is formed so as to protrude from the surface of the power transmission portion 61 on the clean surface 52 side toward the surgical tool 10. Moreover, the clean-side engagement portion 62 can engage with the driven-side engagement portion 14 of the driven portion 13. The unclean-side engagement portion 63 is a concave-shaped portion provided on the surface of the power transmission portion 61 on the unclean surface 53 side. Moreover, the unclean-side engagement portion 63 can engage with the drive-side engagement portion 36 of the drive portion 35.

The drape 71 is a film-shaped member extending from the casing 51 and covers a periphery of the power unit 30. In addition, the unclean region UR on the power unit 30 side and the clean region CR on the surgical tool 10 side are partitioned by the drape 71 so as to be separated from each other. As a material constituting the drape 71, a known material can be used and it is not particularly limited.

Next, attachment and detachment of the power unit 30, the motive power transmission adapter 50, and the surgical tool 10 in the medical manipulator system 1 having the above-described configurations will be described.

As shown in FIG. 1, the motive power transmission adapter 50 is attached to the power unit 30 in the direction in which the drive-side engagement portion 36 of the power unit 30 protrudes. In other words, the above-described direction is a direction intersecting the front-rear direction. In this case, the unclean-side engagement portion 63 of the motive power transmission adapter 50 engages with the drive-side engagement portion 36 of the power unit 30. Moreover, the power unit 30 is covered with the drape 71 of the motive power transmission adapter 50.

The surgical tool 10 is attached to the clean surface 52 of the motive power transmission adapter 50 in the direction in which the clean-side engagement portion 62 of the motive power transmission adapter 50 protrudes. In other words, the above-described direction is a direction intersecting the front-rear direction. In this case, the clean-side engagement portion 62 of the motive power transmission adapter 50 engages with the driven-side engagement portion 14 of the surgical tool 10.

When the surgical tool 10 is removed, the surgical tool 10 is pulled away from the motive power transmission adapter 50 in the direction intersecting the front-rear direction. In other words, when the surgical tool 10 is removed from the motive power transmission adapter 50, it is not necessary to move the surgical tool 10 in the forward direction.

Next, a movement in the medical manipulator system 1 having the above-described configuration will be described.

As shown in FIG. 1, when an instruction to operate the forceps 17 is input to the control unit 37 by the operator who operates the medical manipulator system 1, the control unit 37 generates a control signal according to the instruction of the input operation and performs processing for controlling the actuator unit 33.

The actuator unit 33 generates the driving force which is the force for linearly moving the drive portion 35 in the forward direction, and moves the drive portion 35 by a distance corresponding to the instruction of the input operation. The driving force of the drive portion 35 is transmitted to the driven portion 13 via the engaging power transmission portion 61.

In this case, the driving force of the drive portion 35 moving in the linear motion direction is transmitted to the power transmission portion 61 by the engaged drive-side engagement portion 36 and unclean-side engagement portion 63. The driving force of the power transmission portion 61 in the linear motion direction is transmitted to the driven portion 13 by the engaged clean-side engagement portion 62 and driven-side engagement portion 14.

Similarly to the drive portion 35, the driven portion 13 to which the driving force is transmitted from the power transmission portion 61 is linearly moved in the front-rear direction by the distance corresponding to the instruction of the operation of the operator. The driving force of the driven portion 13 is transmitted to the wire 15, and thus, the drive pulley 16 is rotated by the movement of the wire 15. The drive pulley 16 is rotated according to the movement distance of the wire 15, and the movable piece 17A of the forceps 17 attached to the drive pulley 16 is also rotated.

Next, a movement in a case where the force is detected by the detection unit 34 will be described.

For example, when an external force is applied to the movable piece 17A of the forceps 17 from the outside, the external force is transmitted from the movable piece 17A to the drive pulley 16. Here, examples of the external force include a force which is generated by an article other than the medical manipulator system 1 and other than an object to be grasped by the forceps 17 coming into contact with the forceps 17, a reaction force which is generated when the object is grasped by the forceps 17 and exceeds expectations, and the like.

The external force transmitted to the drive pulley 16 is transmitted to the driven portion 13 via the wire 15. In addition, the external force is transmitted from the driven portion 13 to the drive portion 35 via the power transmission portion 61 and is detected by the detection unit 34. The detection unit 34 which detects the external force outputs information on a magnitude of the detected external force to the control unit 37.

The control unit 37 corrects the control signal output to the actuator unit 33 such that the force applied to the medical manipulator system 1 (for example, forceps 17) does not exceed a desired magnitude or the force applied to the object to be grasped by the forceps 17 does not exceed a desired magnitude. In addition, the control unit 37 sends the signal related to the force to the operation unit (not shown) operated by the operator and provides the information on the force applied to the surgical tool 10 to the operator.

According to the medical manipulator system 1 and the motive power transmission adapter 50 having the above-described configurations, the driving force of the drive portion 35 is transmitted to the driven portion 13 by the power transmission portion 61 moving in the linear motion direction. Accordingly, when the driving force is transmitted, the power transmission portion 61 moving into or moving out of the clean region CR or the unclean region UR is suppressed, and mixture of the clean region CR and the unclean region UR is easily prevented. The linear motion direction is a direction in which the clean surface 52 and the unclean surface 53 extend.

In addition, since the movement direction of the power transmission portion 61 is the direction in which the clean surface 52 and the unclean surface 53 extend, the power transmission portion 61 does not easily protrude from the motive power transmission adapter 50, and unexpected interference between the operator's hand (glove) and the power transmission portion 61 is easily suppressed. Moreover, the power transmission portion 61 does not come into easy contact with an external article, and thus, it is possible to suppress an unexpected movement of the power transmission portion 61 generated by the contact with the outside, and when the surgical tool 10 is attached to the motive power transmission adapter 50, the position of the power transmission portion 61 is easily adjusted.

Moreover, the medical manipulator system 1 and the motive power transmission adapter 50 include the drive-side engagement portion 36 which engages with the unclean-side engagement portion 63 and the driven-side engagement portion 14 which engages with the clean-side engagement portion 62. Accordingly, engagement and disengagement between the power transmission portion 61 and the drive portion 35 and engagement and disengagement between the power transmission portion 61 and the driven portion 13 can be performed. Moreover, the driving force related to the linear movement of the drive portion 35 can be transmitted to the driven portion 13 via the power transmission portion 61.

In addition, in the medical manipulator system 1 and the motive power transmission adapter 50, a plurality of combinations of the driven portions 13, the power transmission portions 61, and the drive portions 35 are provided, and thus, a plurality of movements can be transmitted to the surgical tool 10. In addition, in the first embodiment, the example in which the six driven portions 13, the six power transmission portions 61, and the six drive portions 35 are provided is described. However, the number of the driven portions 13, the number of the power transmission portions 61, and the number of the drive portions 35 may be greater than six or may be smaller than six.

[Second Embodiment]

Next, a second embodiment of the present disclosure will be described with reference to FIGS. 3 to 6. Basic configurations of a medical manipulator system and a motive power transmission adapter of the second embodiment are similar to those of the first embodiment. However, shapes of attachment portions of a surgical tool, the motive power transmission adapter, and a power unit of the second embodiment are different from those of the first embodiment. Accordingly, in the second embodiment, only peripheries of the attachment portions of the surgical tool, the motive power transmission adapter, and the power unit will be described with reference to FIGS. 3 to 6, and descriptions of other configurations or the like are omitted.

Figure 3:
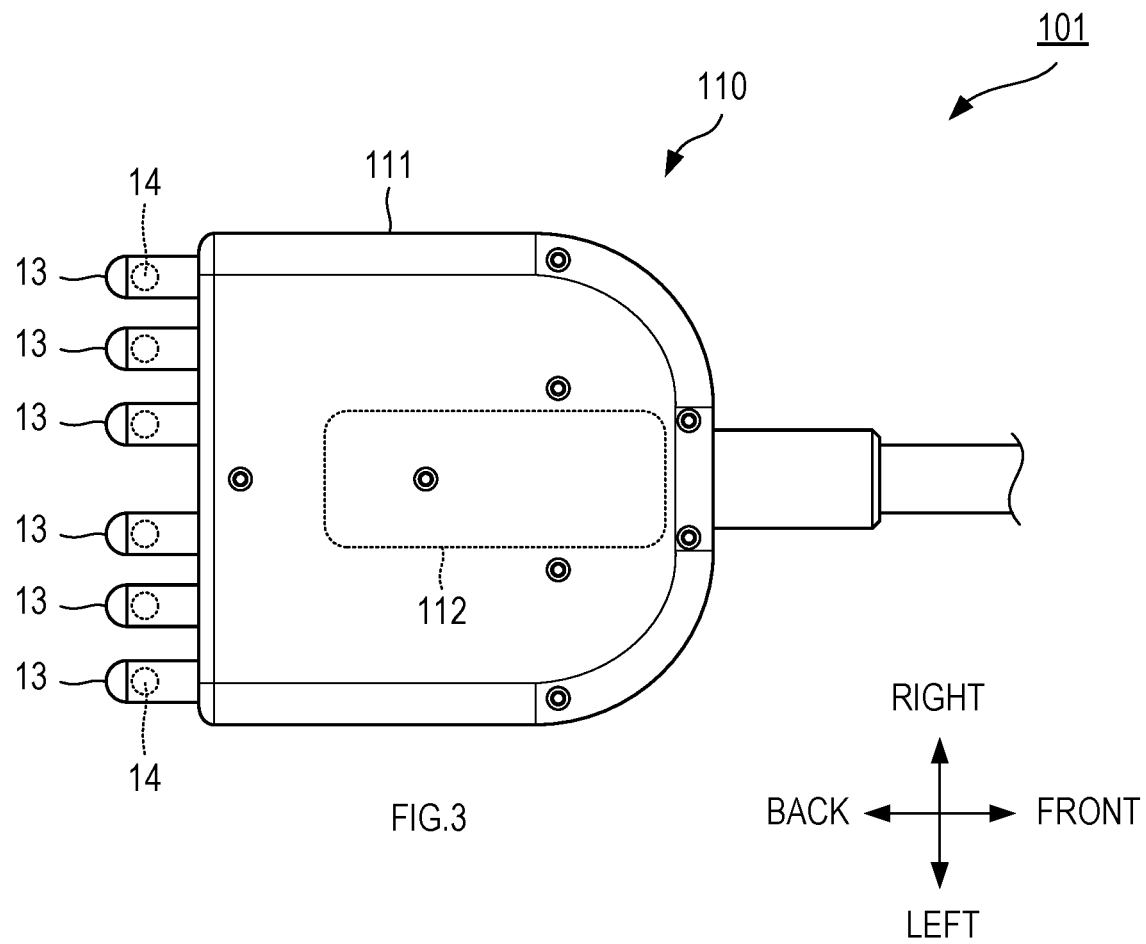
FIG. 3 is a schematic diagram illustrating a configuration of a surgical tool of a medical manipulator according to a second embodiment of the present disclosure.

As shown in FIG. 3, in a surgical tool casing 111 of the surgical tool 110 in the medical manipulator system 101 of the second embodiment, a power unit 130 side, that is, a rear portion which is a portion on the rear side is formed in a flat surface shape or a flat plate shape including the linear motion direction (front-rear direction) and the right-left direction. Similarly to the surgical tool casing 10 of the first embodiment, the driven portion 13, the wire 15, and the drive pulley 16 are accommodated inside the surgical tool casing 111, and the surgical tool casing 111 supports the forceps 17.

The rear portion of the surgical tool casing 111 is attached to a motive power transmission adapter 150. The driven portion 13 protruding toward the rear side is disposed on a rear end of the rear portion of the surgical tool casing 111. The driven portion 13 is disposed so as to be movable relative to the surgical tool casing 11 in the linear motion direction.

In addition, the driven-side engagement portion 14 is provided in a portion of the driven portion 13 protruding from the surgical tool casing 111. In the second embodiment, an example in which six driven portions 13 are disposed to be arranged in the right-left direction will be described.

A second surgical tool regulation portion 112 is provided on a surface (rear-side surface on a paper surface in FIG. 3) of the rear portion of the surgical tool casing 111 facing the motive power transmission adapter 150. The second surgical tool regulation portion 112 corresponds to an example of a second regulation portion. The second surgical tool regulation portion 112 is a portion which is formed so as to protrude from the surgical tool casing 111 and abuts against a first surgical tool regulation portion 152 (described later) of the motive power transmission adapter 150. The second surgical tool regulation portion 112 is formed in a ridge shape which rises so as to extend in the front-rear direction at the center of the surgical tool casing 111 in the right-left direction.

Figure 4:
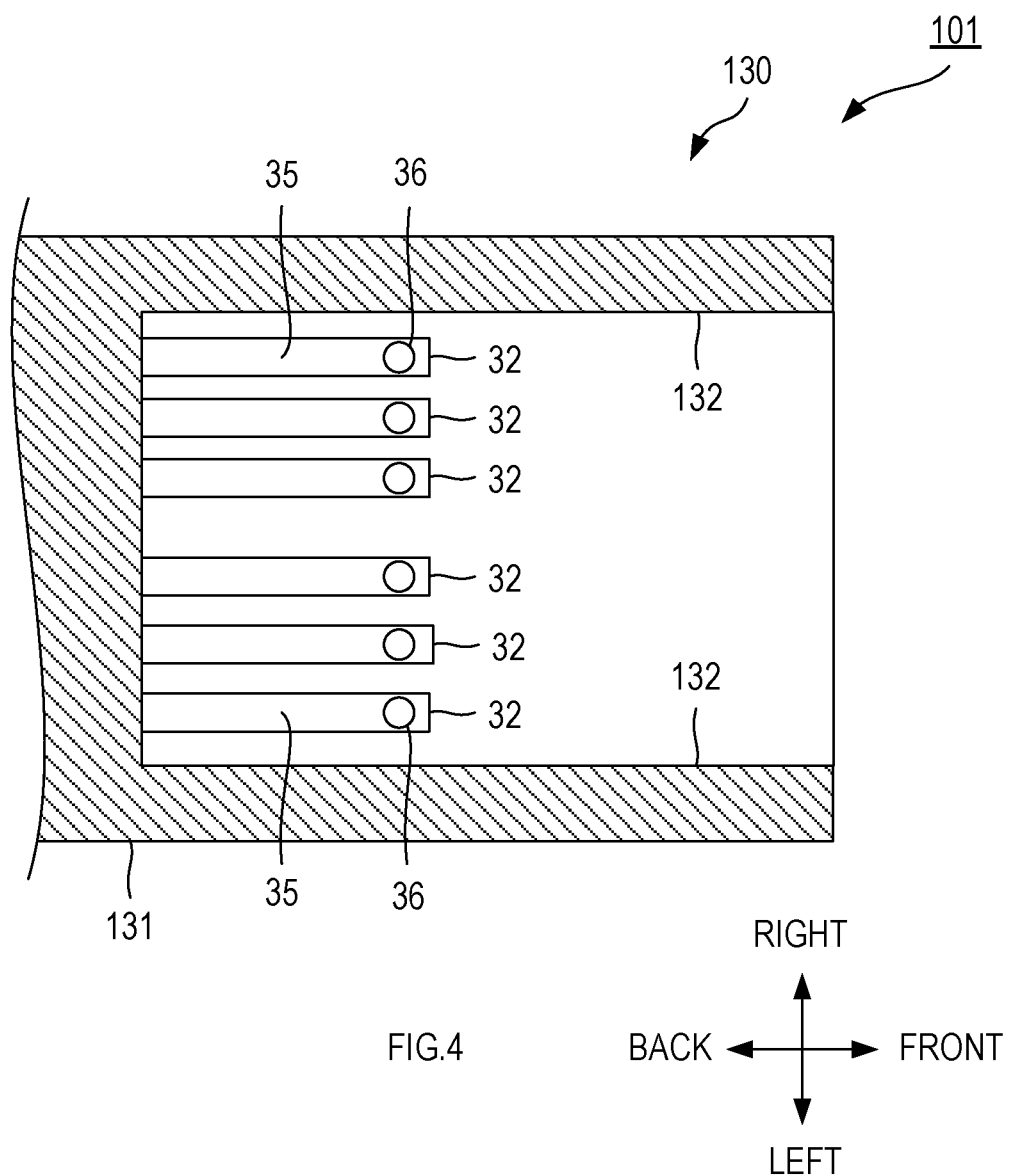
FIG. 4 is a schematic diagram illustrating a configuration of a power unit of the medical manipulator according to the second embodiment of the present disclosure.

As shown in FIG. 4, a power unit casing 131 of the power unit 130 in the medical manipulator system 101 is formed in a rectangular parallelepiped shape. Moreover, similarly to the power unit casing 31 of the first embodiment, the actuator unit 33, the detection unit 34, and the drive portion 35 are accommodated inside the power unit casing 131.

A region which is a surface extending in the front-rear direction and the right-left direction and in which the motive power transmission adapter 150 can be attached and detached is formed on a front side of the power unit casing 131. The power unit slits 32 formed in a groove shape extending in the linear motion direction are provided in the region. The power unit slits 32 are disposed to be arranged in the right-left direction which is the direction intersecting the linear motion direction.

In addition, a pair of second power regulation portions 132 is provided at positions adjacent to the region, in which the power unit slits 32 are provided, in the right-left direction. The pair of second power regulation portions 132 corresponds to an example of a second regulation portion. The pair of second power regulation portions 132 is provided on a right-side end portion and a left-side end portion, respectively, in the front portion of the power unit casing 131, and the pair of second power regulation portions 132 is a pair of surfaces which extends in the front-rear direction and the second power regulation portions 132 face each other. In other words, the motive power transmission adapter 150 is disposed between the pair of second power regulation portions 132 and the pair of second power regulation portions 132 abuts against first power regulation portions 153 (described later) of the power transmission portion 61.

Figure 5:
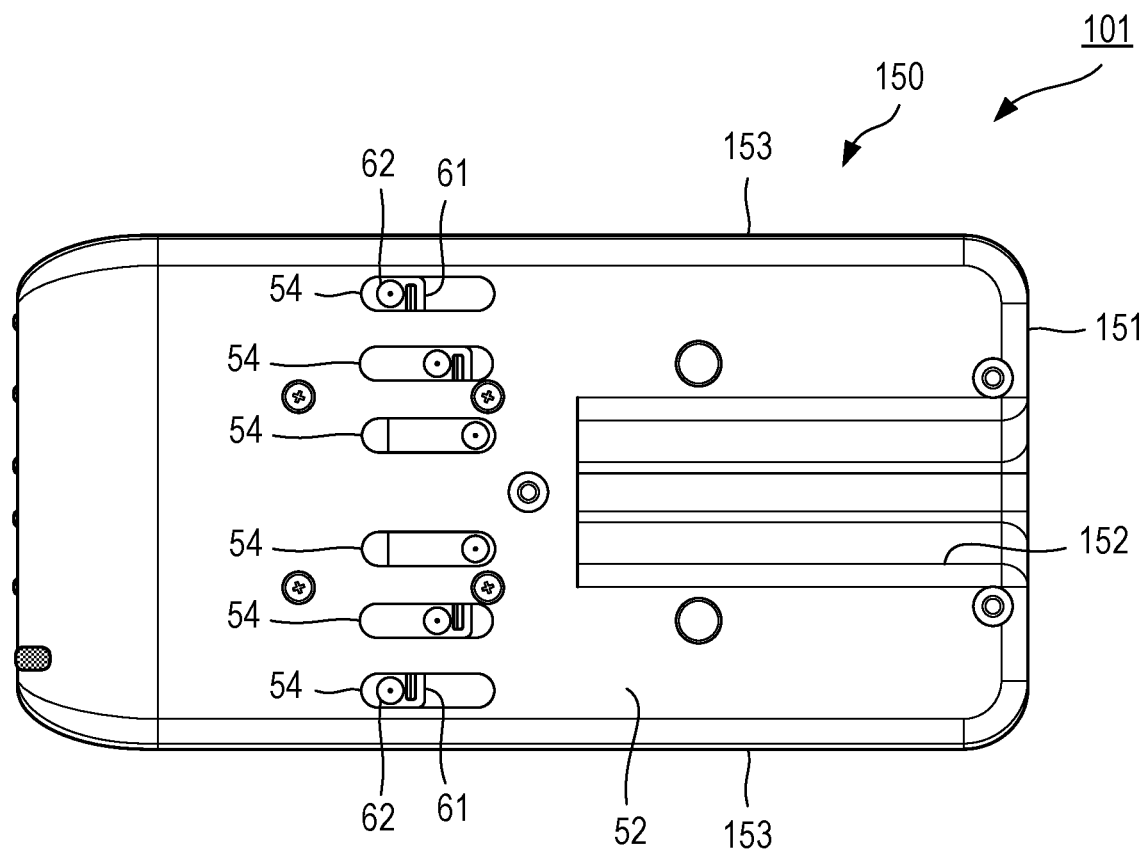
FIG. 5 is a schematic diagram illustrating a configuration of a motive power transmission adapter of the medical manipulator according to the second embodiment of the present disclosure.

As shown in FIG. 5, a casing 151 of the motive power transmission adapter 150 in the medical manipulator system 101 is formed in a flat surface or a plate shape extending in the front-rear direction and the right-left direction, and the power transmission portions 61 are disposed inside the casing 151.

Clean surface slits 54 formed in a groove shape extending in the linear motion direction are provided on the clean surface 52 of the casing 151. Moreover, the first surgical tool regulation portion 152 abutting against the second surgical tool regulation portion 112 of the surgical tool 110 is provided in a region in a forward direction from the clean surface slits 54 of the clean surface 52. The first surgical tool regulation portion 152 corresponds to an example of a first regulation portion. The first surgical tool regulation portion 152 is a concave portion which is provided at the center of the clean surface 52 in the right-left direction and extends in the front-rear direction. The second surgical tool regulation portion 112 can be inserted into the first surgical tool regulation portion 152 while abutting against the first surgical tool regulation portion 152, and thus, the second surgical tool regulation portion 112 can be removed. In the second embodiment, an example in which an end portion of the first surgical tool regulation portion 152 in the forward direction is open is described.

The first power regulation portions 153 abutting against the second power regulation portions 132 of the power unit 130 are provided on edges of the casing 151 which are end portions in the right-left direction and extend in the front-rear direction. The first power regulation portion 153 corresponds to an example of the first regulation portion. The first power regulation portions 153 abut against the second power regulation portions 132 when the casing 151 is disposed inside the second power regulation portion 132 of the power unit 130.

Next, attachment and detachment of the power unit 130, the motive power transmission adapter 150, and the surgical tool 110 in the medical manipulator system 101 having the above-described configurations will be described.

Figure 6:
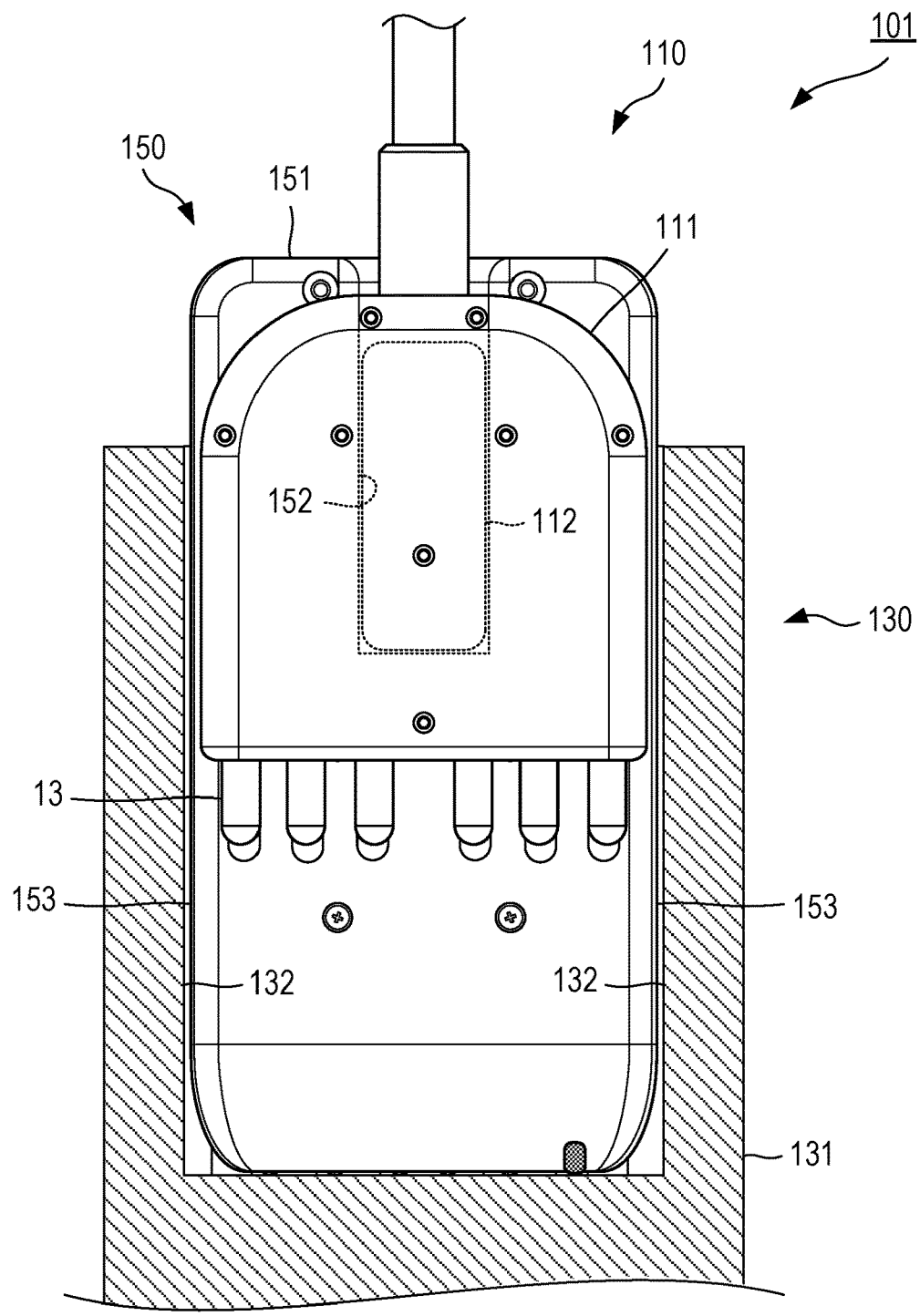
FIG. 6 is a schematic diagram illustrating attached states of the surgical tool, the motive power transmission adapter, and the power unit.

As shown in FIG. 6, the motive power transmission adapter 150 is attached to the power unit 130 from a side of the power unit 130 in which the second power regulation portions 132 are provided, that is, from a front side with respect to a paper surface of FIG. 6. In this case, the motive power transmission adapter 150 is disposed between the pair of second power regulation portions 132, and the first power regulation portions 153 of the motive power transmission adapter 150 abut against the pair of second power regulation portions 132 of the power unit 130. In this case, a relative movement in the front-rear direction between the power unit 130 and the motive power transmission adapter 150 is allowed, and a relative movement in the right-left direction therebetween is regulated.

The surgical tool 110 is attached from the clean surface 52 side on which the first surgical tool regulation portion 152 of the motive power transmission adapter 150 is provided, that is, from a front side with respect the paper surface of FIG. 6. In this case, the second surgical tool regulation portion 112 of the surgical tool 110 is inserted into the first surgical tool regulation portion 152 of the motive power transmission adapter 150. In this case, the first surgical tool regulation portion 152 and the second surgical tool regulation portion 112 abut against each other, a relative movement in the front-rear direction between the motive power transmission adapter 150 and the surgical tool 110 is allowed, and a relative movement in the right-left direction therebetween is regulated.

According to the medical manipulator system 101 and the motive power transmission adapter 150 having the above-described configurations, the six power transmission portions 61 are disposed to be arranged on a flat surface, and thus, the configuration of the motive power transmission adapter 150 is easily simplified to improve manufacturability of the motive power transmission adapter 150. In addition, the six power transmission portions 61 are disposed to be arranged on a flat surface, and thus, in a case where the surgical tool 110 is removed from the power transmission portion 61, it is not necessary to move the surgical tool 110 toward a patient present on an extension in the linear motion direction of the drive portion 35, and it is possible to remove the surgical tool 110 from the motive power transmission adapter 150 while moving the surgical tool 110 in a direction intersecting the clean surface 52 of the motive power transmission adapter 150. Accordingly, for example, even in a case where the surgical tool 110 is attached to the motive power transmission adapter 150 so as to be fixed and locked to the motive power transmission adapter 150, and thereafter, the surgical tool 110 is unexpectedly unlocked and is disconnected from the motive power transmission adapter 150, the surgical tool 110 falls off in the direction intersecting the clean surface 52. That is, it is possible to prevent the surgical tool 110 from unexpectedly falling off from the motive power transmission adapter 150 toward the patient.

The first surgical tool regulation portion 151 and the first power regulation portions 153 are provided, and thus, when the surgical tool 110 and the power unit 130 are attached to or detached from the motive power transmission adapter 150, the direction in which the surgical tool 110 and the power unit 130 move relative to each other is regulated in a direction in which the surgical tool 110 and the power unit 130 move toward each other or away from each other and the front-rear direction. Therefore, workability in the attachment and detachment of the surgical tool 110 and the power unit 130 or safety in surgery is easily improved.

The second surgical tool regulation portion 112 and the second power regulation portions 132 are provided, and thus, when the motive power transmission adapter 150 is attached to or detached from the power unit 130 or the surgical tool 110, the direction in which the motive power transmission adapter 150 moves relative to the power unit 130 or the surgical tool 110 is regulated in the direction in which the motive power transmission adapter 150 and the power unit 130 or the surgical tool 110 move toward each other or away from each other and the front-rear direction. Therefore, workability in the attachment and detachment of the motive power transmission adapter 150 or safety in surgery is easily improved.

[Third Embodiment]

Next, a third embodiment of the present disclosure will be described with reference to FIGS. 7 and 8. Basic configurations of a medical manipulator system and a motive power transmission adapter of the third embodiment are similar to those of the first embodiment. However, shapes of attachment portions of a surgical tool, the motive power transmission adapter, and a power unit of the third embodiment are different from those of the first embodiment. Accordingly, in the third embodiment, only peripheries of the attachment portions of the surgical tool, the motive power transmission adapter, and the power unit will be described with reference to FIGS. 7 and 8, and descriptions of other configurations or the like are omitted.

Figure 7:
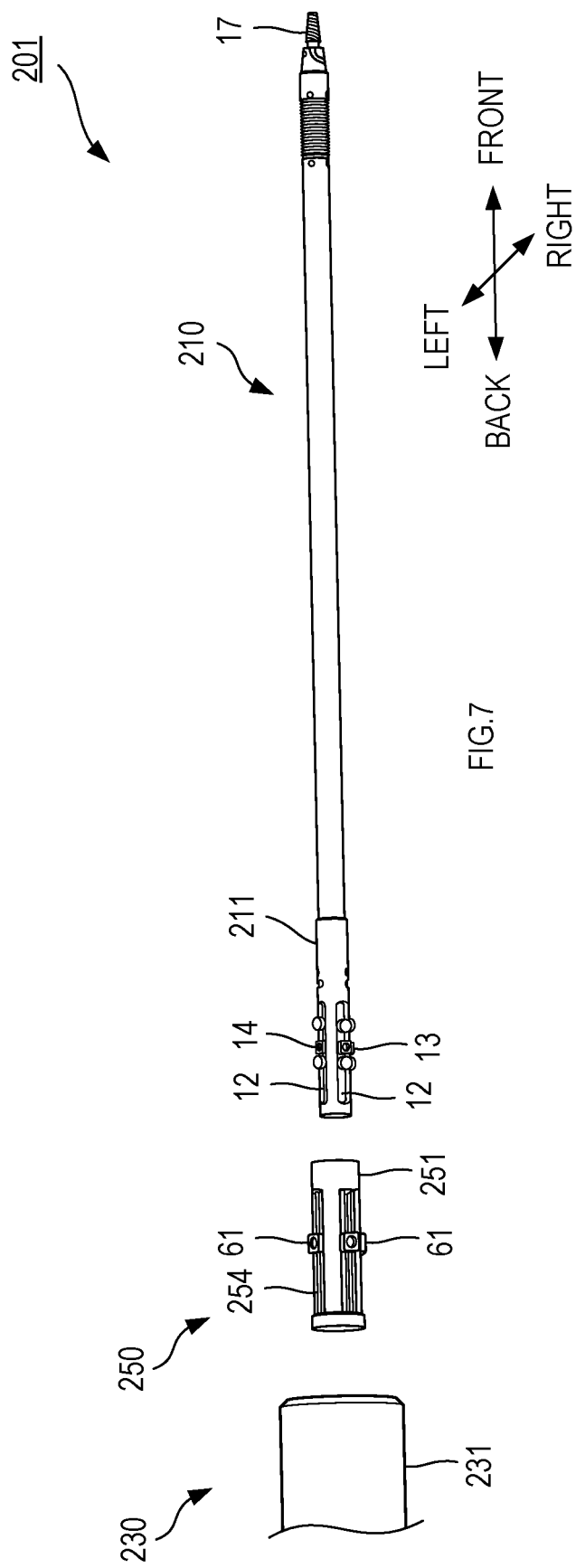
FIG. 7 is a partially enlarged view illustrating a configuration of a medical manipulator according to a third embodiment of the present disclosure.

As shown in FIG. 7, a surgical tool casing 211 of a surgical tool 210 in a medical manipulator system 201 of the third embodiment is formed in a cylindrical shape or a columnar shape about an axis in which a rear portion which is a portion on a power unit 230 side (rear side) extends in the linear motion direction (front-rear direction). Similarly to the surgical tool casing 10 of the first embodiment, the driven portion 13, the wire 15, and the drive pulley 16 are accommodated inside the surgical tool casing 211, and the surgical tool casing 211 supports the forceps 17.

The rear portion of the surgical tool casing 211 is a portion which is attached to a motive power transmission adapter 250. Surgical tool slits 12 extending in the linear motion direction are provided on a circumferential surface of the rear portion of the surgical tool casing 211. In the third embodiment, an example in which four surgical tool slits 12 are disposed at equal intervals in a circumferential direction will be described.

As shown in FIG. 7, a power unit casing 231 of the power unit 230 in the medical manipulator system 201 is formed in a cylindrical shape or a columnar shape. Moreover, similarly to the power unit casing 31 of the first embodiment, the actuator unit 33, the detection unit 34, and the drive portion 35 are accommodated inside the power unit casing 231.

A region which is a cylindrical inner surface about an axis extending along the linear motion direction and in which the motive power transmission adapter 250 can be attached and detached is formed on a front side of the power unit casing 231. The power unit slits 32 formed in a groove shape extending in the linear motion direction are provided in the region. In the third embodiment, an example in which four power unit slits 32 are provided will be described. The four power unit slits 32 are disposed to be arranged at equal intervals in the circumferential direction.

Figure 8:
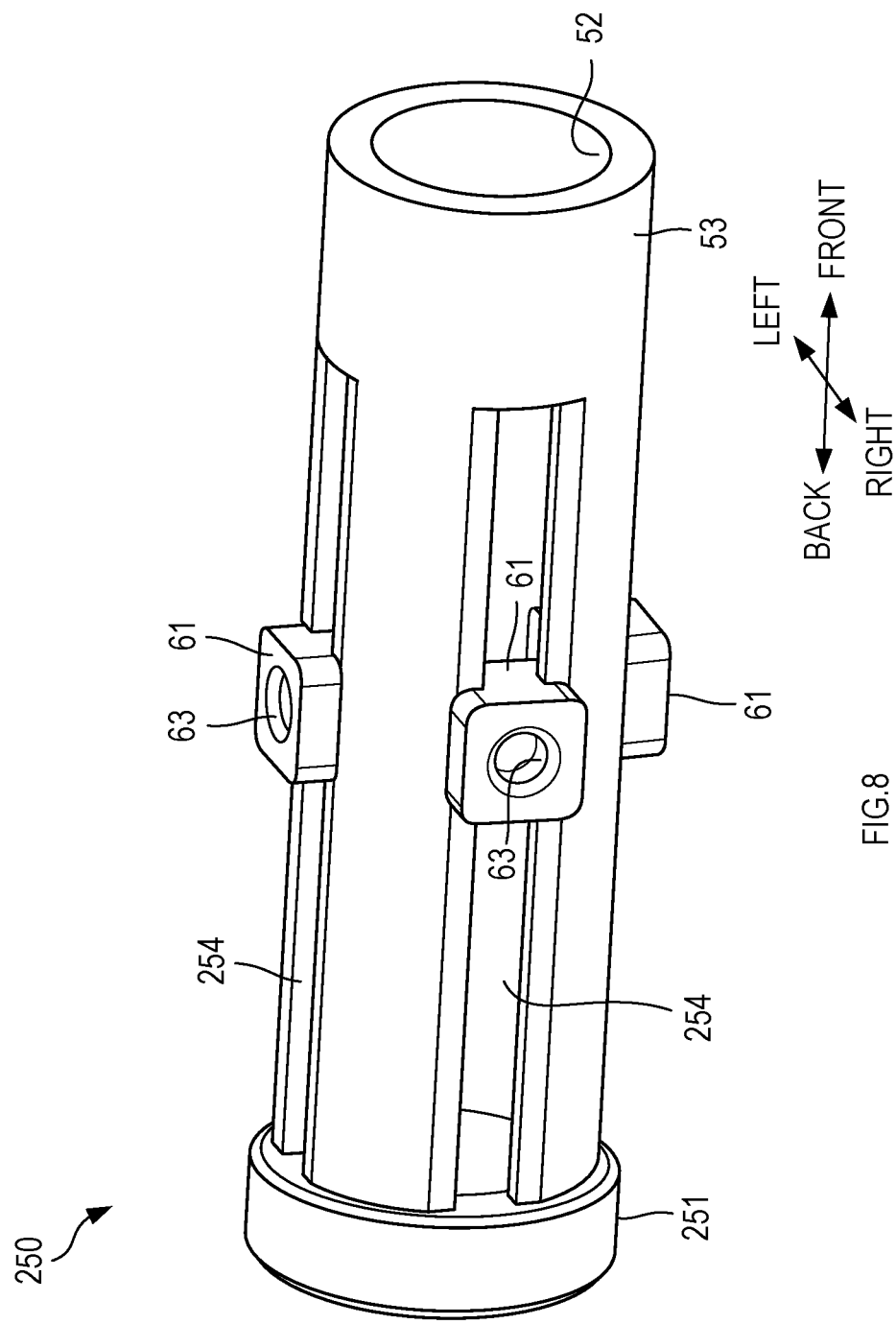
FIG. 8 is a perspective diagram illustrating the configuration of the motive power transmission adapter of FIG. 6.

As shown in FIGS. 7 and 8, a casing 251 of the motive power transmission adapter 250 in the medical manipulator system 201 is formed in a cylindrical shape about the axis extending along the linear motion direction. The power transmission portions 61 are disposed in the casing 251. An inner peripheral surface of the casing 251 is the clean surface 52 and an outer peripheral surface thereof is the unclean surface 53.

A guide portion 254 formed in a groove shape extending in the linear motion direction is provided in the casing 251. In the third embodiment, an example in which four guide portions 254 are disposed to be arranged at equal intervals in the circumferential direction will be described. Each guide portion 254 holds the power transmission portion 61 such that the power transmission portion 61 is relatively movable in the linear motion direction. The first embodiment and the third embodiment are different from each other in that the power transmission portion 61 is not accommodated inside the casing 251 in the third embodiment.

Next, attachment and detachment of the power unit 230, the motive power transmission adapter 250, and the surgical tool 210 in the medical manipulator system 201 having the above-described configurations will be described.

As shown in FIG. 7, the motive power transmission adapter 250 is attached to the power unit 230 from a forward direction side of the power unit 230. Specifically, the motive power transmission adapter 250 moves toward the power unit 230 along the linear motion direction from the front direction side and is inserted into an internal space of the power unit casing 231. When the motive power transmission adapter 250 is removed from the power unit 230, the motive power transmission adapter 250 is pulled forward from the power unit 230 along the linear motion direction.

The surgical tool 210 is attached to the motive power transmission adapter 250 from a forward direction side of the motive power transmission adapter 250. Specifically, the surgical tool 210 moves toward the motive power transmission adapter 250 along the linear motion direction from the front direction side and is inserted into an internal space of the surgical tool casing 211. When the surgical tool 210 is removed from the motive power transmission adapter 250, the surgical tool 210 is pulled forward from the motive power transmission adapter 250 along the linear motion direction.

According to the medical manipulator system 201 and the motive power transmission adapter 250 having the above-described configurations, the four power transmission portions 61 are disposed so as to be circumferentially arranged on an outer peripheral surface of the casing 251 formed in a tubular shape, and thus the configuration of the motive power transmission adapter 250 is easily simplified to improve manufacturability of the motive power transmission adapter 250.

The guide portion 254 in which the power transmission portion 61 is disposed to be movable in the linear motion direction is provided, and thus, the power transmission portion 61 is prevented from moving in a direction different from the linear motion direction. Accordingly, positioning between the power transmission portion 61 and the drive portion 35 and positioning between the power transmission portion 61 and the driven portion 13 are easily performed.

In addition, the above-described embodiment, the example in which the casing 251 of the motive power transmission adapter 250 is formed in a cylindrical shape or a columnar shape is described. However, the casing 251 may be formed in a prismatic cylindrical shape or a prismatic shape. In a case where the casing 251 is formed in a prismatic cylindrical shape or a prismatic shape, the surgical tool casing 211 is similarly formed in a prismatic cylindrical shape or a prismatic shape, and the inner surface of the power unit casing 231 is also formed in a prismatic cylindrical shape or a shape corresponding to a prismatic shape.

Moreover, in the third embodiment, the example in which the four power transmission portions 61 or the four guide portions 254 are provided is described. However, the number of the power transmission portions 61 or the guide portions 254 may be greater than four or may be smaller than four.

[Fourth Embodiment]

Next, a fourth embodiment of the present disclosure will be described with reference to FIGS. 9 to 12. Basic configurations of a medical manipulator system and a motive power transmission adapter of the fourth embodiment are similar to those of the second embodiment. However, shapes of attachment portions of a surgical tool and the motive power transmission adapter of the fourth embodiment are different from those of the second embodiment. Accordingly, in the fourth embodiment, only peripheries of the attachment portions of the surgical tool and the motive power transmission adapter will be described with reference to FIGS. 9 to 12C, and descriptions of other configurations or the like are omitted.

Figure 9:
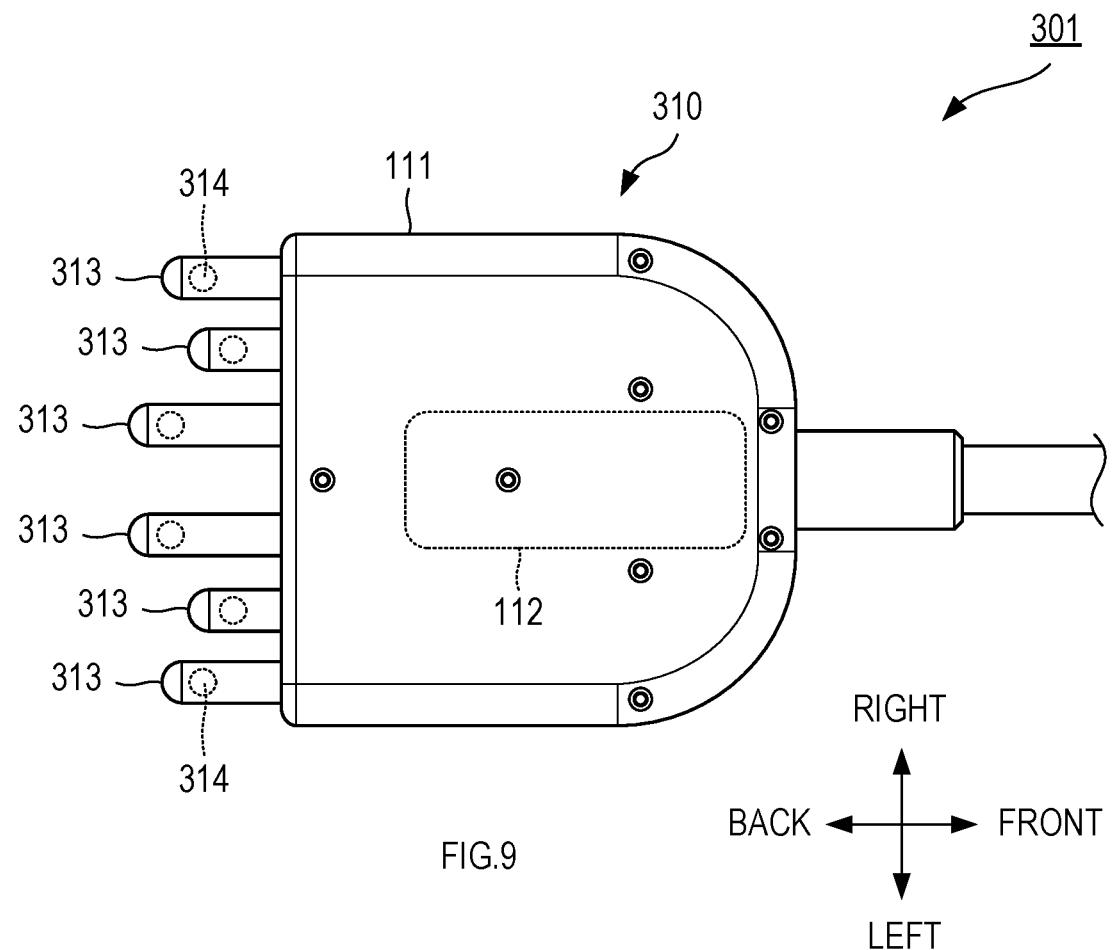
FIG. 9 is a schematic diagram illustrating a configuration of a surgical tool of a medical manipulator according to a fourth embodiment of the present disclosure.

As shown in FIGS. 9 and 12B, a driven engagement portion 314 is provided in a driven portion 313 of a surgical tool 310 in a medical manipulator system 301 of the fourth embodiment. The driven engagement portion 314 is provided in a region which is a rearward end portion of the driven portion 313 and protrudes rearward from the surgical tool casing 111. Moreover, the driven engagement portion 314 is a rod-shaped member which extends from the driven portion 313 toward a motive power transmission adapter 350.

Figure 10:
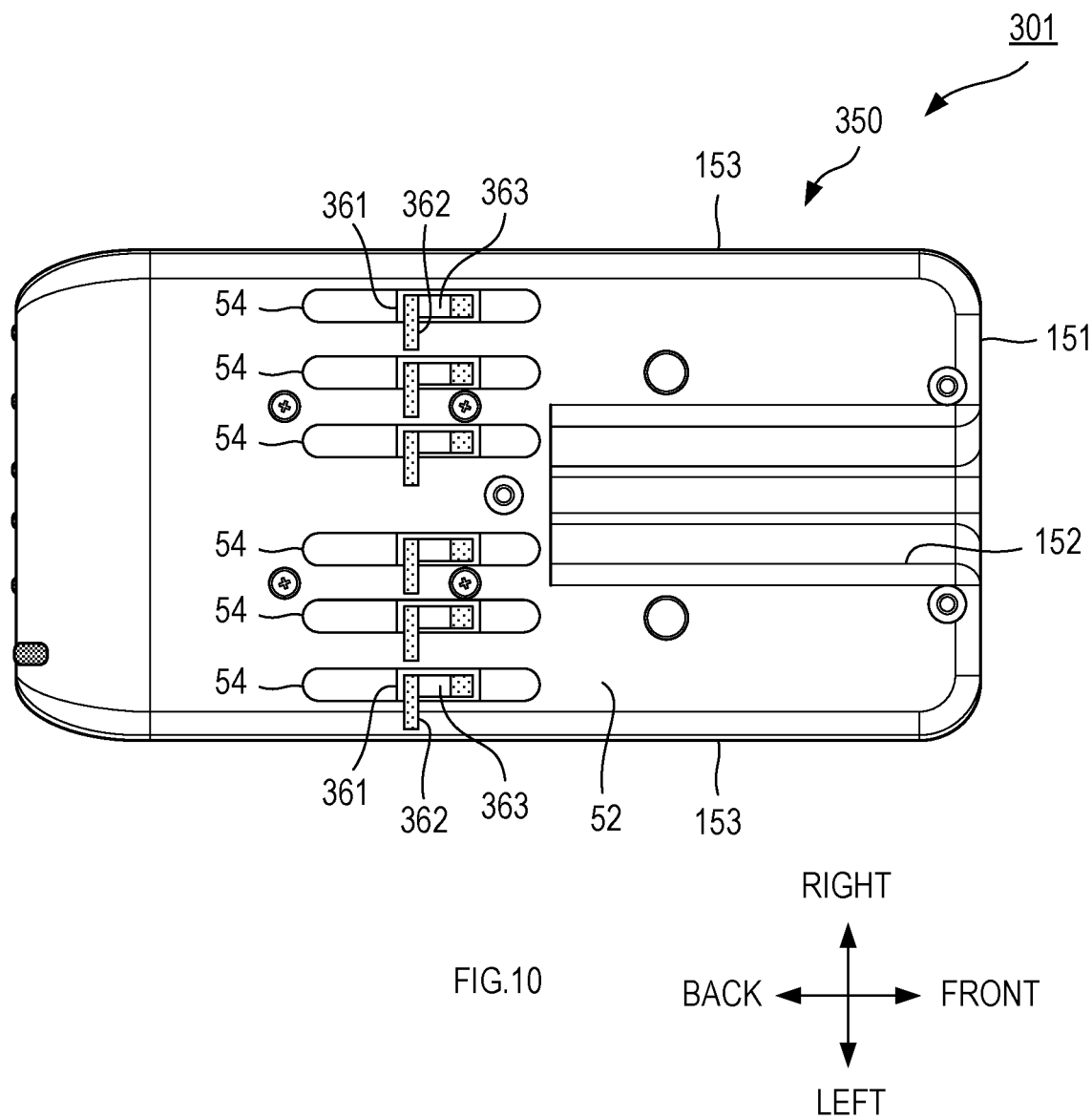
FIG. 10 is a schematic diagram illustrating a configuration of a motive power transmission adapter of the medical manipulator according to the fourth embodiment of the present disclosure.

As shown in FIGS. 10 and 12B, a first driven abutment surface 362 and a first driven holding portion 363 are provided in a power transmission portion 361 of the motive power transmission adapter 350 in the medical manipulator system 301.

The first driven abutment surface 362 is a member which protrudes from a surface of the power transmission portion 361 facing the surgical tool 310 toward the surgical tool 310 and is formed in a plate shape extending in the right-left direction. In the first driven abutment surface 362, one end portion has a shape which protrudes in the right-left direction from the clean surface slit 54.

The first driven holding portion 363 has a concave-shaped portion which is formed to be adjacent to the first driven abutment surface 362. The first driven holding portion 363 holds the driven engagement portion 314 inside the concave-shaped portion thereof. The first driven holding portion 363 is a member which is formed to extend in the front-rear direction, the first driven abutment surface 362 is disposed on a rearward end portion of the first driven holding portion 363, a convex-shape portion protruding toward the surgical tool 310 is formed on a forward end portion of the first driven holding portion 363, and the above-described concave-shaped portion is formed in the center of the first driven holding portion 363. In the concave-shaped portion of the first driven holding portion 363, end portions thereof in the right-left direction are open, and thus, the driven engagement portion 314 can move into or move out of the concave-shaped portion in the right-left direction.

Next, attachment and detachment of the motive power transmission adapter 350 and the surgical tool 310 in the medical manipulator system 301 having the above-described configurations will be described.

When the surgical tool 310 is attached to the motive power transmission adapter 350, as shown in FIG. 12A, the surgical tool 310 moves toward the motive power transmission adapter 350 in a forward direction with respect to the motive power transmission adapter 350.

In this case, the surgical tool 310 is disposed such that a center in the right-left direction is shifted relative to the motive power transmission adapter 350 in the right-left direction, and the driven engagement portion 314 abuts against the first driven abutment surface 362 without interfering with the first driven holding portion 363.

Figure 11:
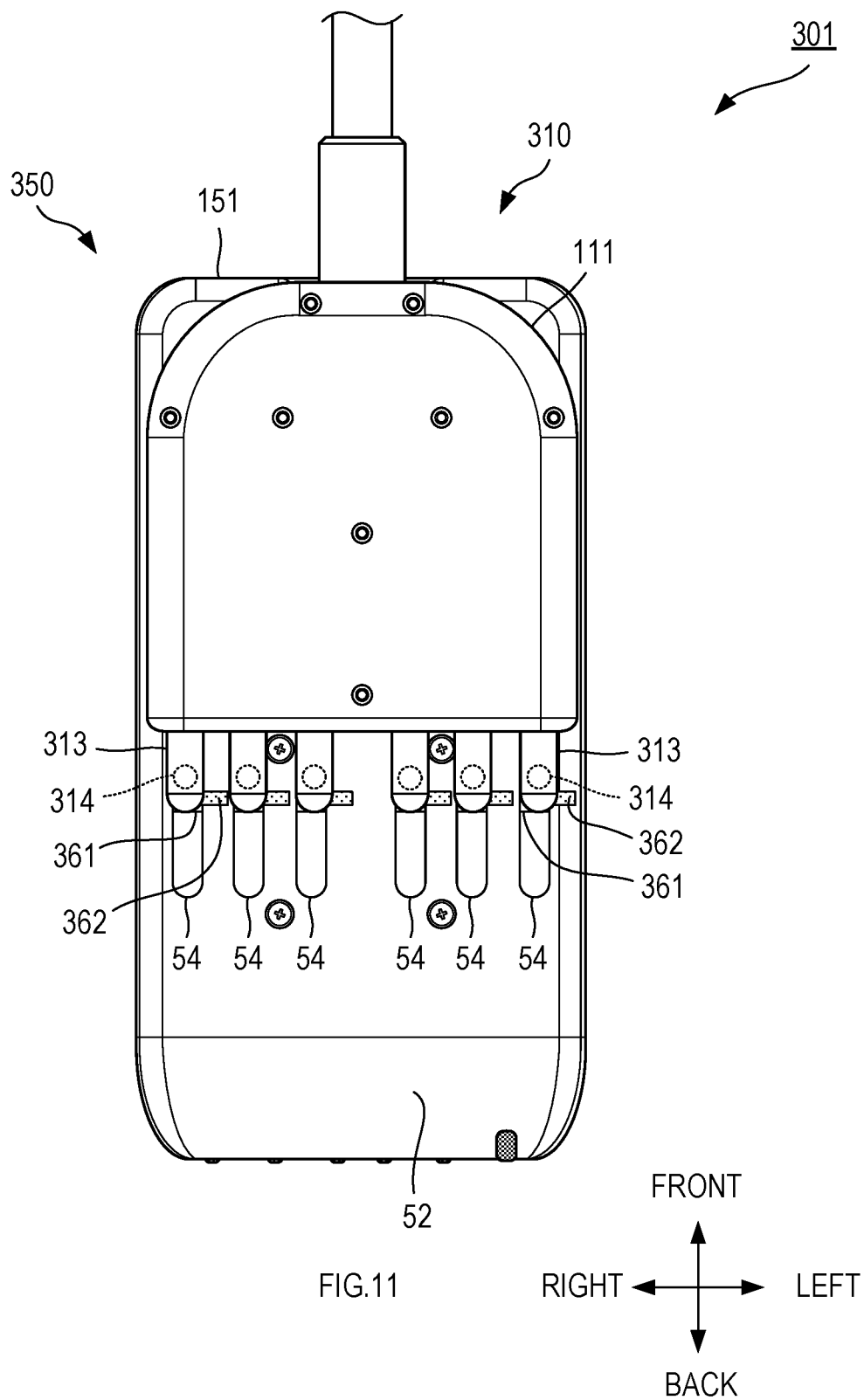
FIG. 11 is a schematic diagram illustrating an attachment state of the surgical tool of FIG. 9 and the motive power transmission adapter of FIG. 10.

As shown in FIG. 12B, the driven engagement portion 314 abuts against the first driven abutment surface 362 and the surgical tool 310 is attached to the motive power transmission adapter 350 at a predetermined relative position (refer to FIG. 11). In this case, the driven portion 313 is regulated by the power transmission portion 361 to be aligned at a desired position. In the fourth embodiment, as shown in FIG. 11, the disposition positions of the six driven portions 313 in the front-rear direction are aligned so as to be the same as each other.

Thereafter, as shown in FIGS. 11 and 12C, the surgical tool 310 is moved in the right-left direction with respect to the motive power transmission adapter 350, and the centers of the motive power transmission adapter 350 and the surgical tool 310 in the right-left direction coincide with each other. In this case, the driven engagement portion 314 is disposed inside the concave-shaped portion of the first driven holding portion 363.

In this disposition, if the power transmission portion 361 moves in the forward direction, the driven engagement portion 314 and the first driven abutment surface 362 abut against each other and a driving force of the power transmission portion 361 is transmitted to the driven portion 313. Conversely, if the power transmission portion 361 moves in the rearward direction, the driven engagement portion 314 abuts against the convex-shaped portion of the first driven holding portion 363, and the driving force of the power transmission portion 361 is transmitted to the driven portion 313.

According to the medical manipulator system 301 and the motive power transmission adapter 350 having the above-described configurations, the first driven abutment surface 362 is provided, and thus, it is possible to regulate the position of the driven portion 313 when the surgical tool 310 is attached to the motive power transmission adapter 350. Therefore, the power transmission portion 361 and the driven portion 313 easily engage with each other, and thus, workability is easily improved when the surgical tool 310 is attached to the motive power transmission adapter 350.

The first driven holding portion 363 is provided, and thus, it is possible to transmit the driving force in both directions in the linear motion direction between the power transmission portion 361 and the driven portion 313, that is, in the forward direction and the rearward direction. Since the engagement state between the power transmission portion 361 and the driven portion 313 is maintained, controllability of the surgical tool 310 easily increases, and safety is easily secured in surgery.

[Fifth Embodiment]

Next, a fifth embodiment of the present disclosure will be described with reference to FIGS. 13 to 15.

Basic configurations of a medical manipulator system and a motive power transmission adapter of the fifth embodiment are similar to those of the second embodiment. However, shapes of attachment portions of a surgical tool and the motive power transmission adapter of the fifth embodiment are different from those of the second embodiment. Accordingly, in the fifth embodiment, only peripheries of the attachment portions of the surgical tool and the motive power transmission adapter will be described with reference to FIGS. 13 to 15, and descriptions of other configurations or the like are omitted.

Figure 13:
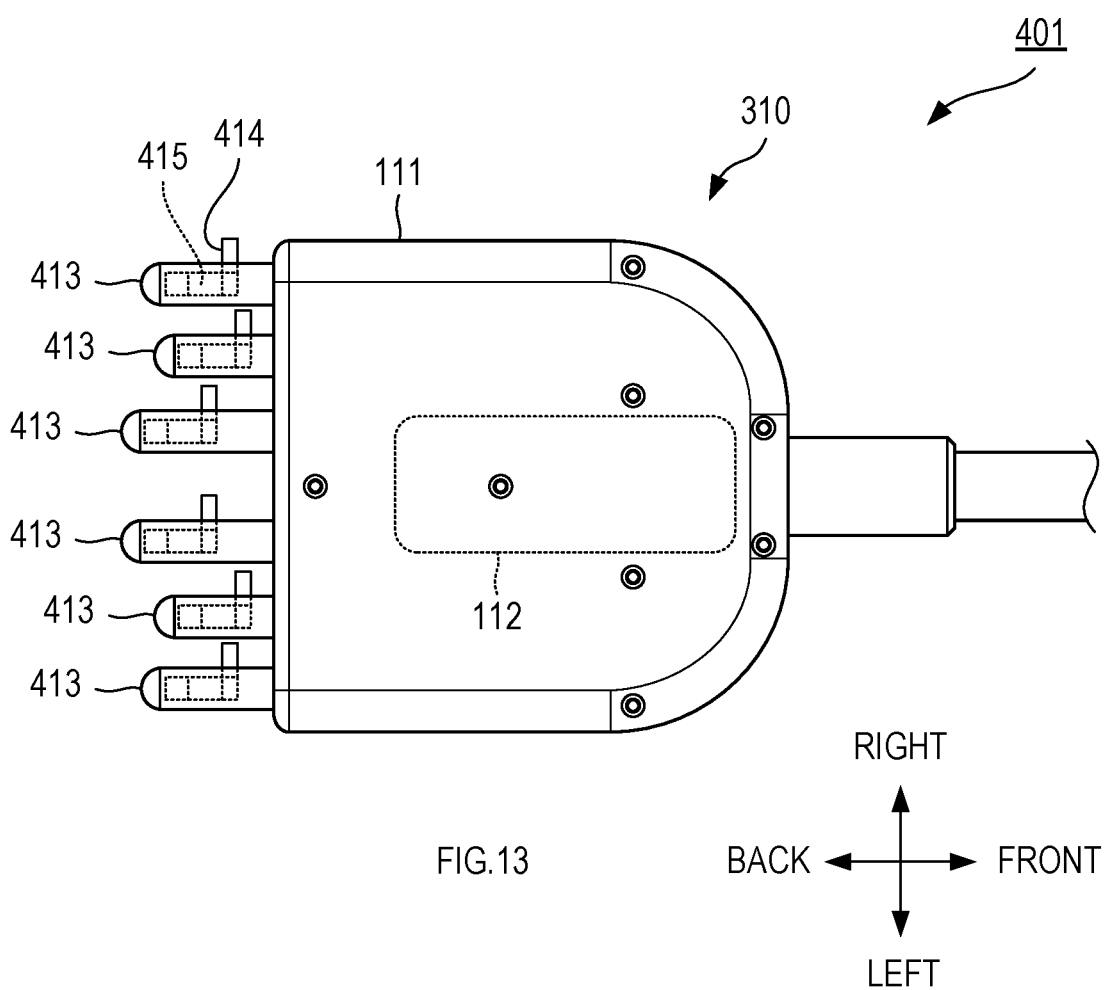
FIG. 13 is a schematic diagram illustrating a configuration of a surgical tool of a medical manipulator according to a fifth embodiment of the present disclosure.

As shown in FIG. 13, driven portions 413 of a surgical tool 410 in a medical manipulator system 401 of the fifth embodiment include second driven abutment surfaces 414 and second driven holding portions 415.

Each second driven abutment surface 414 is a member which protrudes from a surface of the driven portion 413 facing a motive power transmission adapter 450 toward the motive power transmission adapter 450 and is formed in a plate shape extending in the right-left direction. In the second driven abutment surface 414, one end portion has a shape which protrudes in the right-left direction from the driven portion 413.

Each second driven holding portion 415 has a concave-shaped portion which is formed to be adjacent to the second driven abutment surface 414. The second driven holding portion 415 holds a transmission engagement portion 462 inside the concave-shaped portion. The second driven holding portion 415 is a member which is formed to extend in the front-rear direction. The second driven abutment surface 414 is disposed on a forward end portion of the second driven holding portion 415, a convex-shaped portion protruding toward the motive power transmission adapter 450 is formed on a rearward end portion of the second driven holding portion 415, and the above-described concave-shaped portion is formed at the center of the second driven holding portion 415. In the concave-shaped portion of the second driven holding portion 415, end portions thereof in the right-left direction are open, and thus, a transmission engagement portion 462 can move into or move out of the concave-shaped portion in the right-left direction.

Figure 14:
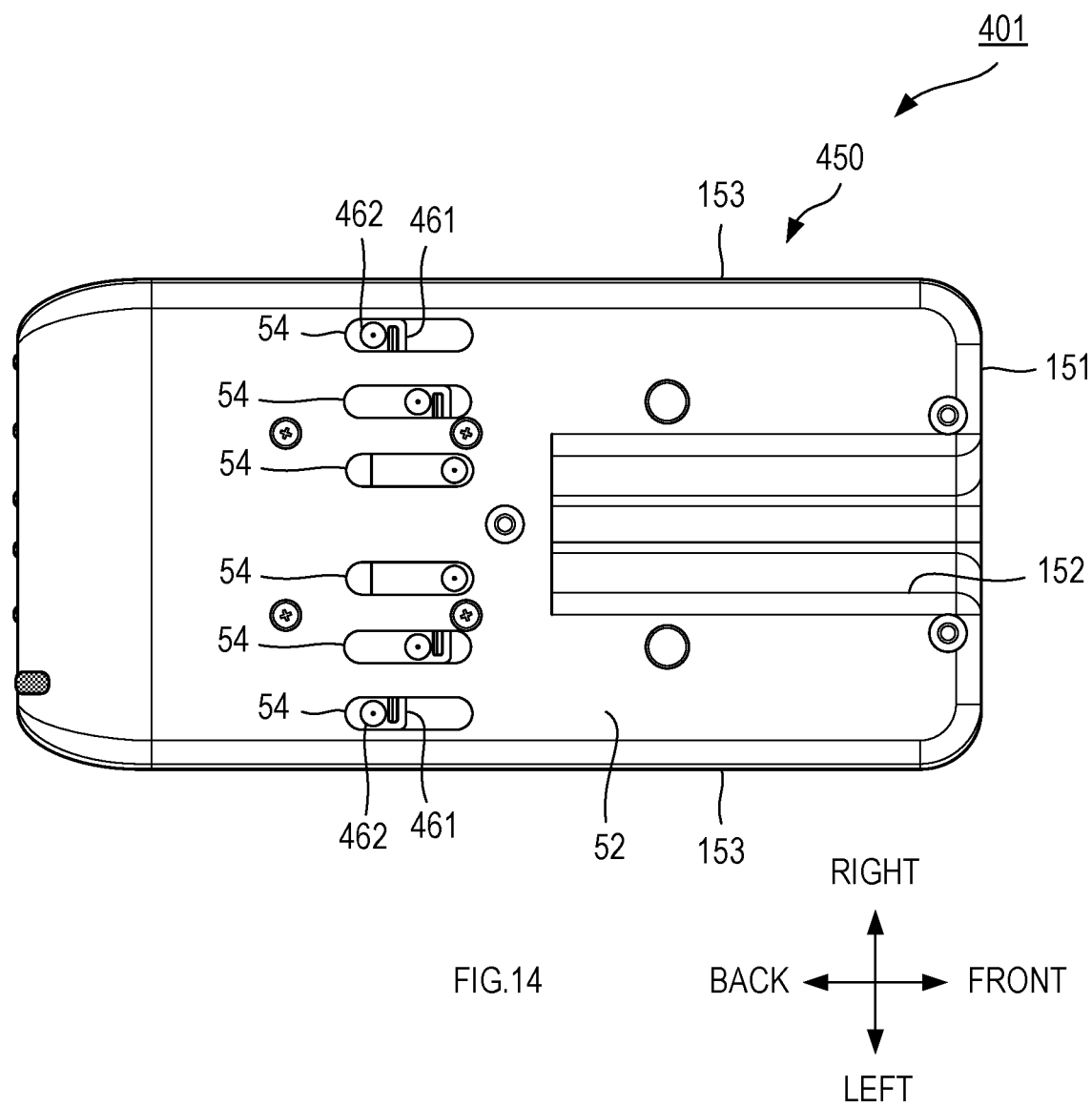
FIG. 14 is a schematic diagram illustrating a configuration of a motive power transmission adapter of the medical manipulator according to the fifth embodiment of the present disclosure.
Figure 15:
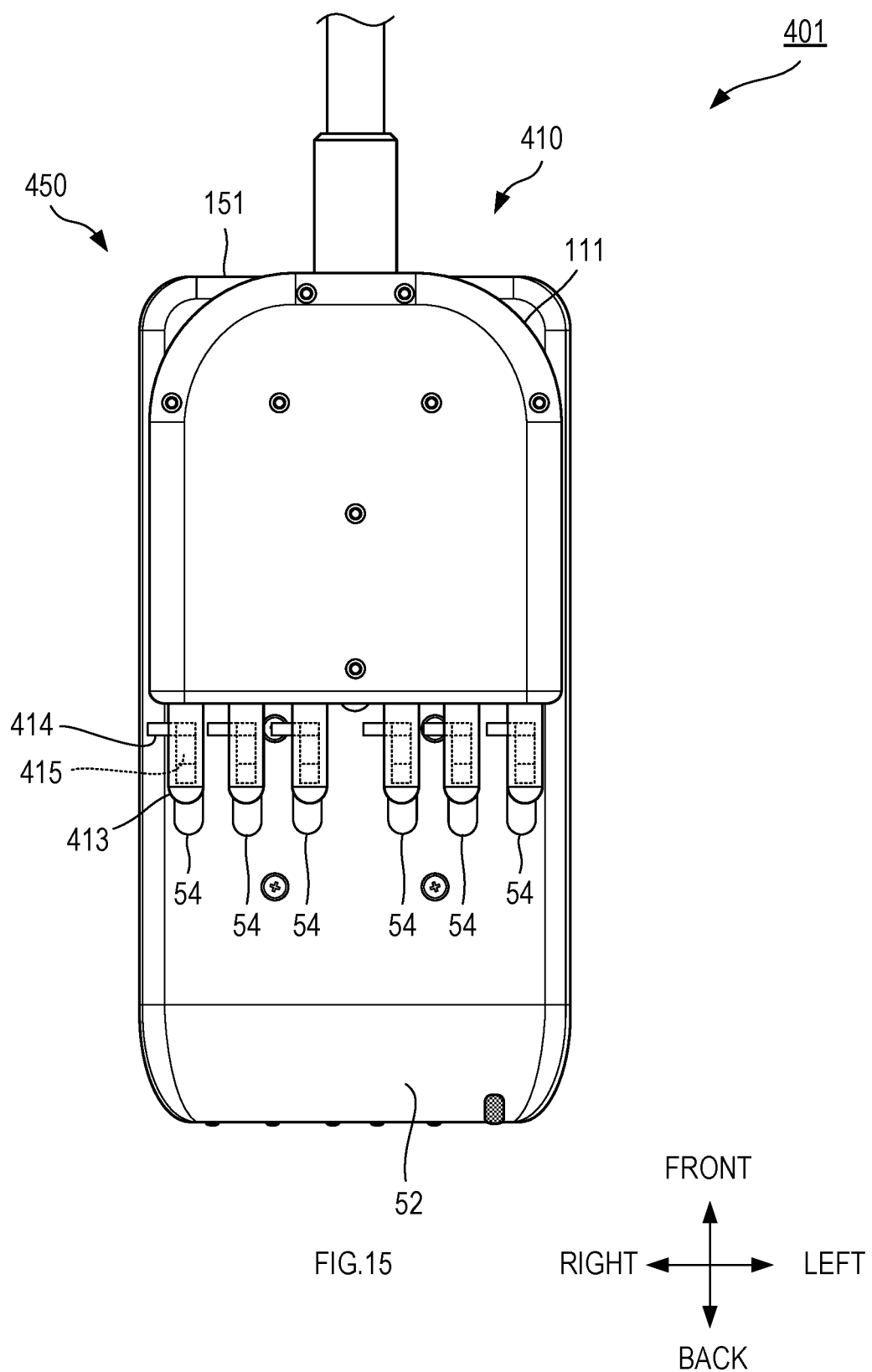
FIG. 15 is a schematic diagram illustrating an attachment state of the surgical tool of FIG. 13 and the motive power transmission adapter of FIG. 14.

As shown in FIG. 14, each of power transmission portions 461 of the motive power transmission adapter 450 in the medical manipulator system 401 includes the transmission engagement portion 462. The transmission engagement portion 462 is a rod-shaped member which extends from the power transmission portion 461 toward the surgical tool 410.

Attachment and detachment of the motive power transmission adapter 450 and the surgical tool 410 in the medical manipulator system 401 having the above-described configurations are similar to those of the fourth embodiment, and thus, descriptions thereof are omitted.

According to the medical manipulator system 401 and the motive power transmission adapter 450 having the above-described configurations, the second driven abutment surface 414 is provided, and thus, it is possible to regulate the position of the power transmission portion 461 when the motive power transmission adapter 450 is attached to the surgical tool 410. Therefore, the driven portion 413 and the power transmission portion 461 easily engage with each other, and thus, workability is easily improved when the surgical tool 410 is attached to the motive power transmission adapter 450.

The second driven holding portion 415 is provided, and thus, it is possible to transmit the movement in both directions in the linear motion direction between the driven portion 413 and the power transmission portion 461, that is, in the forward direction and the rearward direction. Since the engagement state between the driven portion 413 and the power transmission portion 461 is maintained, controllability of the surgical tool 410 easily increases, and safety is easily secured in surgery.

[Sixth Embodiment]

Next, a sixth embodiment of the present disclosure will be described with reference to FIGS. 16 to 19. Basic configurations of a medical manipulator system and a motive power transmission adapter of the sixth embodiment are similar to those of the second embodiment. However, shapes of attachment portions of a power unit and the motive power transmission adapter of the sixth embodiment are different from those of the second embodiment. Accordingly, in the sixth embodiment, only peripheries of the attachment portions of the power unit and the motive power transmission adapter will be described with reference to FIGS. 16 to 19C, and descriptions of other configurations or the like are omitted.

Figure 16:
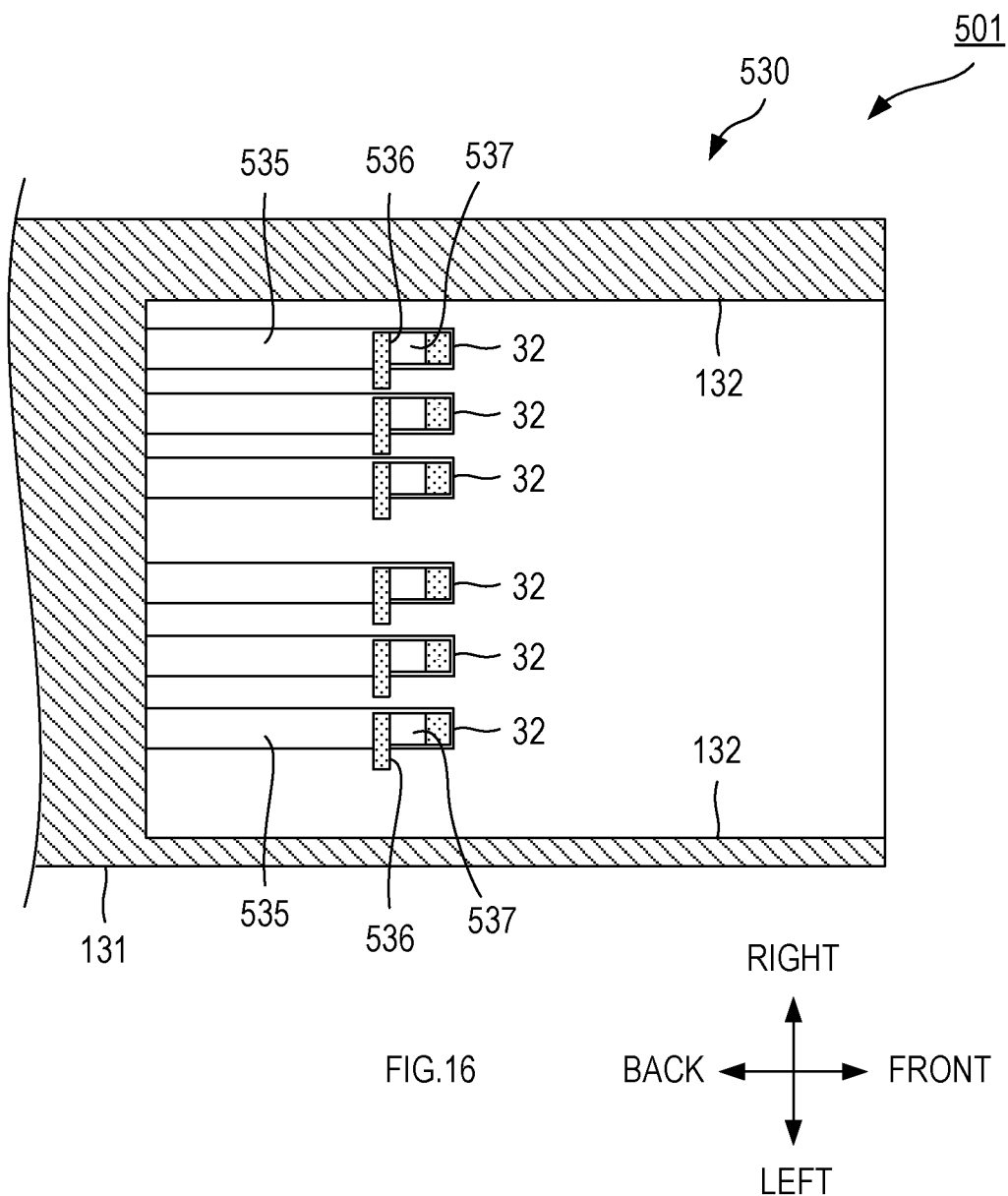
FIG. 16 is a schematic diagram illustrating a configuration of a power unit of a medical manipulator according to a sixth embodiment of the present disclosure.

As shown in FIGS. 16 and 19B, a drive portion 535 of a power unit 530 in a medical manipulator system 501 of the sixth embodiment includes second drive abutment surfaces 536 and second drive holding portions 537.

Each second drive abutment surface 536 is a member which protrudes from a surface of the drive portion 535 facing a motive power transmission adapter 550 toward the motive power transmission adapter 550 and is formed in a plate shape extending in the right-left direction. In the second drive abutment surface 536, one end portion has a shape which protrudes in the right-left direction from a power unit slit 32.

Each second drive holding portion 537 has a concave-shaped portion which is formed to be adjacent to the second drive abutment surface 536. The second drive holding portion 537 holds a transmission engagement portion 562 inside the concave-shaped portion. The second drive holding portion 537 is a member which is formed to extend in the front-rear direction. The second drive abutment surface 536 is disposed on a rearward end portion of the second drive holding portion 537, a convex-shaped portion protruding toward the motive power transmission adapter 550 is formed on a forward end portion of the second drive holding portion 537, and the above-described concave-shaped portion is formed at the center of the second drive holding portion 537. In the concave-shaped portion of the second drive holding portion 537, end portions thereof in the right-left direction are open, and thus, the transmission engagement portion 562 can move into or move out of the concave-shaped portion in the right-left direction.

Figure 17:
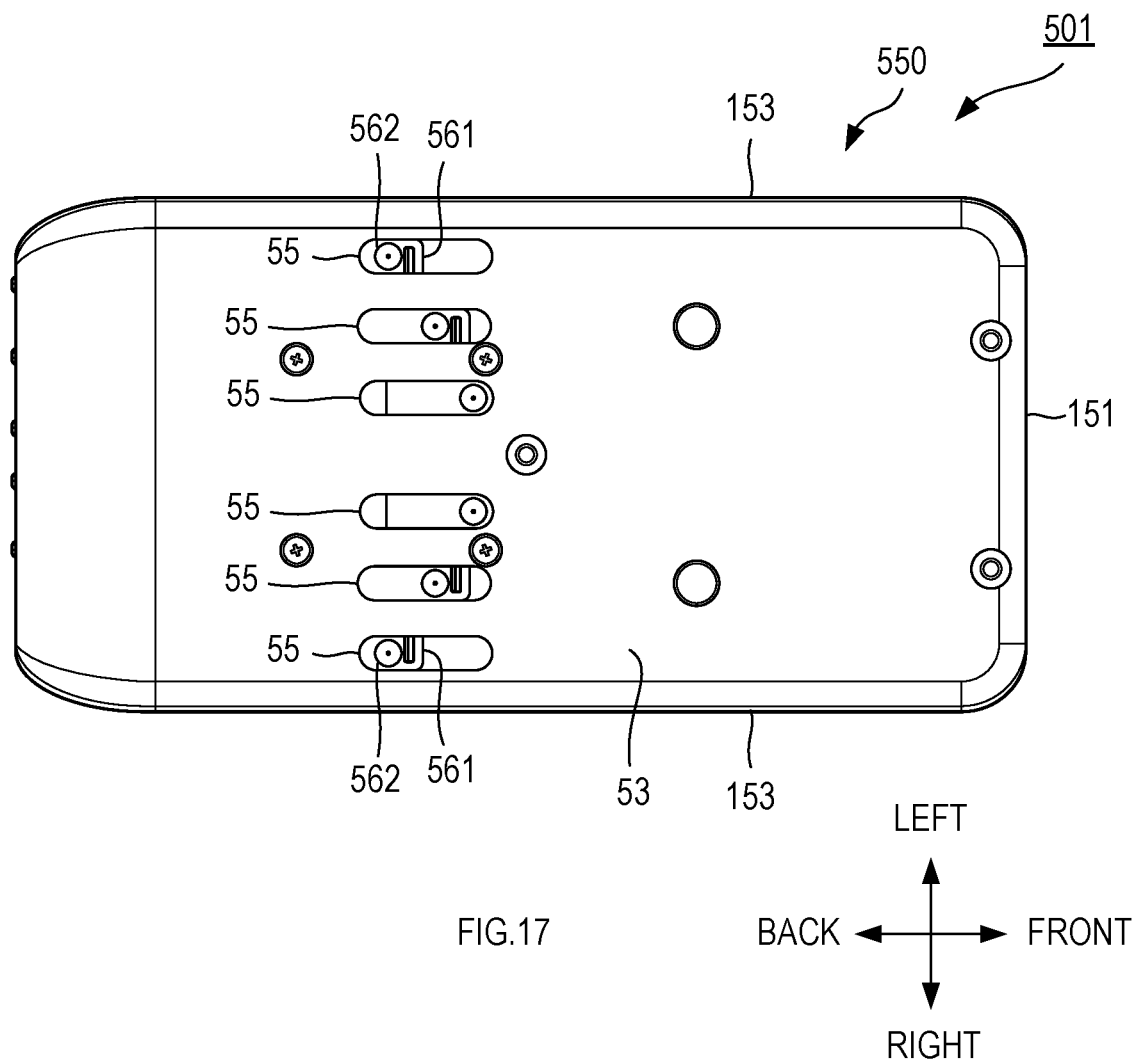
FIG. 17 is a schematic diagram illustrating a configuration of a motive power transmission adapter of the medical manipulator according to the sixth embodiment of the present disclosure.

As shown in FIGS. 17 and 19B, each of power transmission portions 561 of the motive power transmission adapter 550 in the medical manipulator system 501 includes a transmission engagement portion 562. The transmission engagement portion 562 is a rod-shaped member which extends from the power transmission portion 561 toward the power unit 530.

Next, attachment and detachment of the motive power transmission adapter 550 and the power unit 530 in the medical manipulator system 501 having the above-described configurations will be described.

When the motive power transmission adapter 550 is attached to the power unit 530, as shown in FIG. 19A, the motive power transmission adapter 550 moves toward the power unit 530 in a forward direction with respect to the power unit 530.

In this case, the motive power transmission adapter 550 is disposed such that a center of the motive power transmission adapter 550 in the right-left direction is shifted relative to the power unit 530 in the right-left direction, and the transmission engagement portion 562 abuts against the second drive abutment surface 536 without interfering with the second drive holding portion 537.

Figure 18:
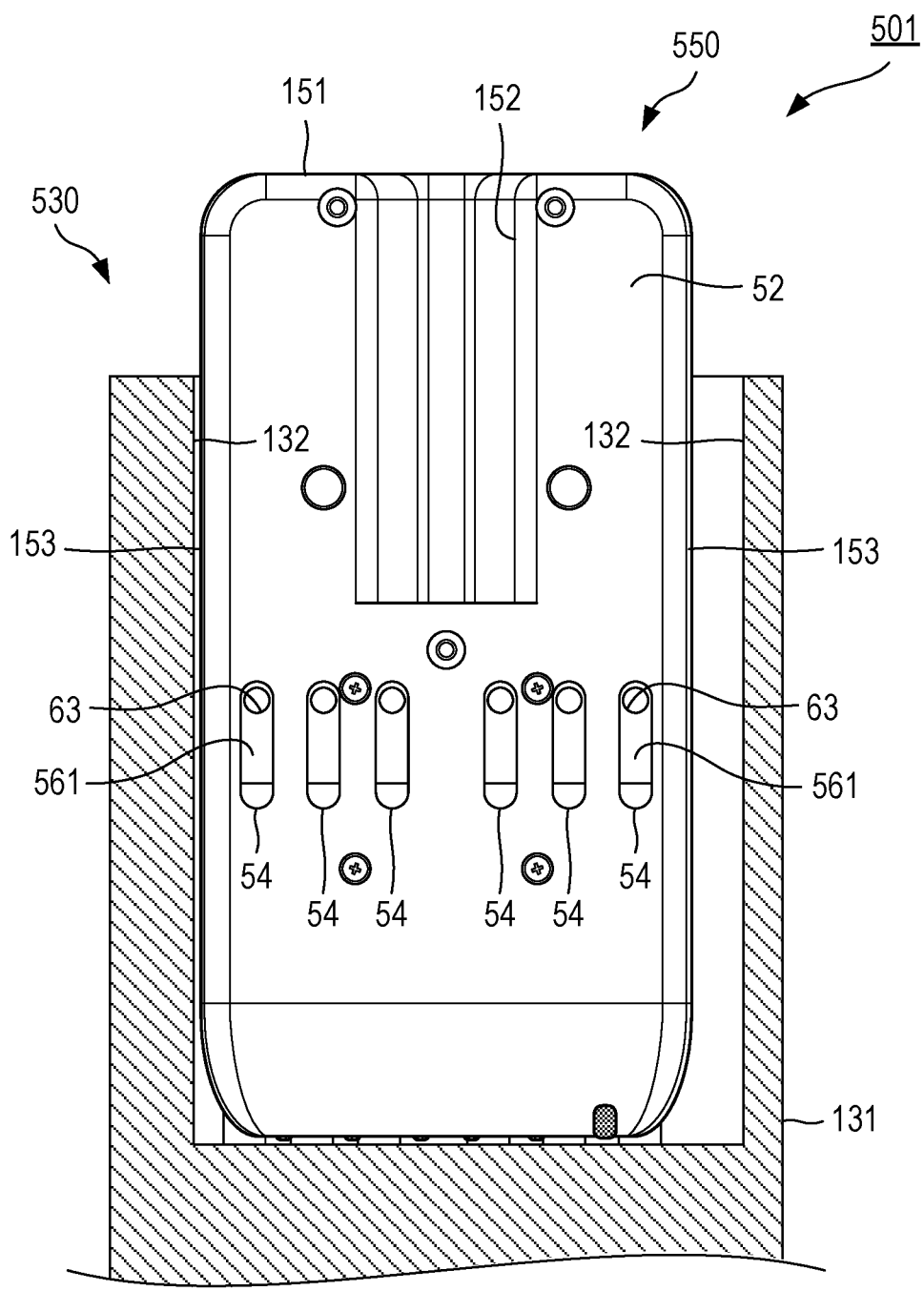
FIG. 18 is a schematic diagram illustrating an attachment state of the power unit of FIG. 16 and the motive power transmission adapter of FIG. 17.

As shown in FIG. 19B, the transmission engagement portion 562 abuts against the second drive abutment surface 536 and the motive power transmission adapter 550 is attached to the power unit 530 at a predetermined relative position (refer to FIG. 18). In this case, the power transmission portion 561 is regulated by the drive portion 535 to be aligned at a desired position. In the sixth embodiment, as shown in FIG. 18, the disposition positions of the six power transmission portions 561 in the front-rear direction are aligned so as to be the same as each other.

Thereafter, as shown in FIGS. 18 and 19C, the motive power transmission adapter 550 is moved in the right-left direction with respect to the power unit 530, and the centers of the power unit 530 and the motive power transmission adapter 550 in the right-left direction coincide with each other. In this case, the transmission engagement portion 562 is disposed inside the concave-shaped portion of the second drive holding portion 537.

In this disposition, if the drive portion 535 moves in the forward direction, the second drive abutment surface 536 and the transmission engagement portion 562 abut against each other and the movement of the drive portion 535 is transmitted to the power transmission portion 561. Conversely, if the drive portion 535 moves in the rearward direction, the convex-shaped portion of the second drive holding portion 537 abuts against the transmission engagement portion 562, and the movement of the drive portion 535 is transmitted to the power transmission portion 561.

According to the medical manipulator system 501 and the motive power transmission adapter 550 having the above-described configurations, the second drive abutment surface 536 is provided, and thus, it is possible to regulate the position of the power transmission portion 561 when the motive power transmission adapter 550 is attached to the power unit 530. Therefore, the drive portion 535 and the power transmission portion 561 easily engage with each other, and thus, workability at the time of the attachment is easily improved.

The second drive holding portion 537 is provided, and thus, it is possible to transmit the movement in both directions in the linear motion direction between the drive portion 535 and the power transmission portion 561, that is, in the forward direction and the rearward direction. Since the engagement state between the drive portion 535 and the power transmission portion 561 is maintained, controllability of the medical manipulator system 501 easily increases, and safety is easily secured in surgery.

[Seventh Embodiment]

Next, a seventh embodiment of the present disclosure will be described with reference to FIGS. 20 and 21. Basic configurations of a medical manipulator system and a motive power transmission adapter of the seventh embodiment are similar to those of the second embodiment. However, shapes of attachment portions of a power unit and the motive power transmission adapter of the seventh embodiment are different from those of the second embodiment. Accordingly, in the seventh embodiment, only peripheries of the attachment portions of the power unit and the motive power transmission adapter will be described with reference to FIGS. 20 and 21, and descriptions of other configurations or the like are omitted.

Figure 20:
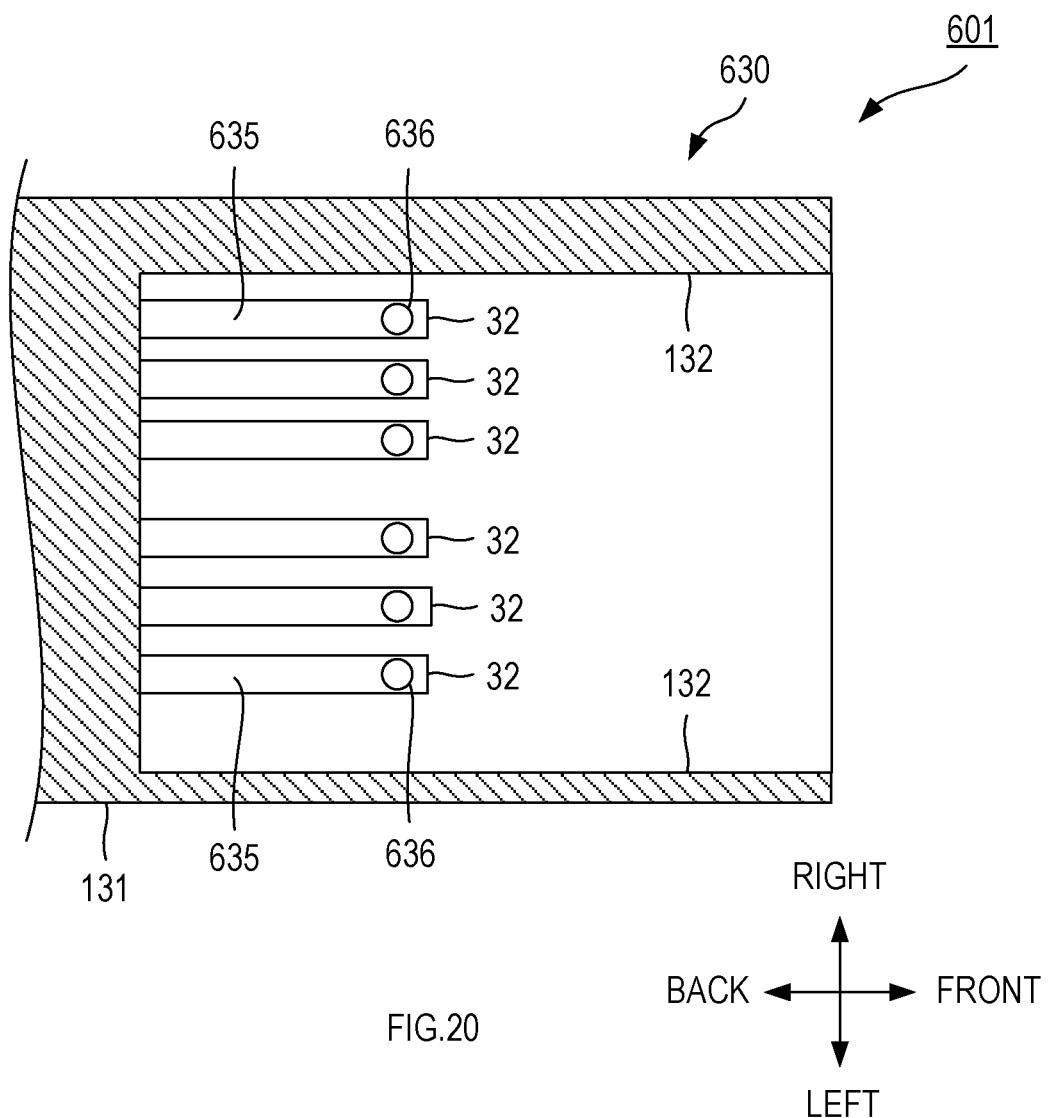
FIG. 20 is a schematic diagram illustrating a configuration of a power unit of a medical manipulator according to a seventh embodiment of the present disclosure.

As shown in FIG. 20, drive portions 635 of a power unit 630 in a medical manipulator system 601 of the seventh embodiment include drive engagement portions 636. Each drive engagement portion 636 is a rod-shaped member which extends from the drive portion 635 toward a motive power transmission adapter 650.

Figure 21:
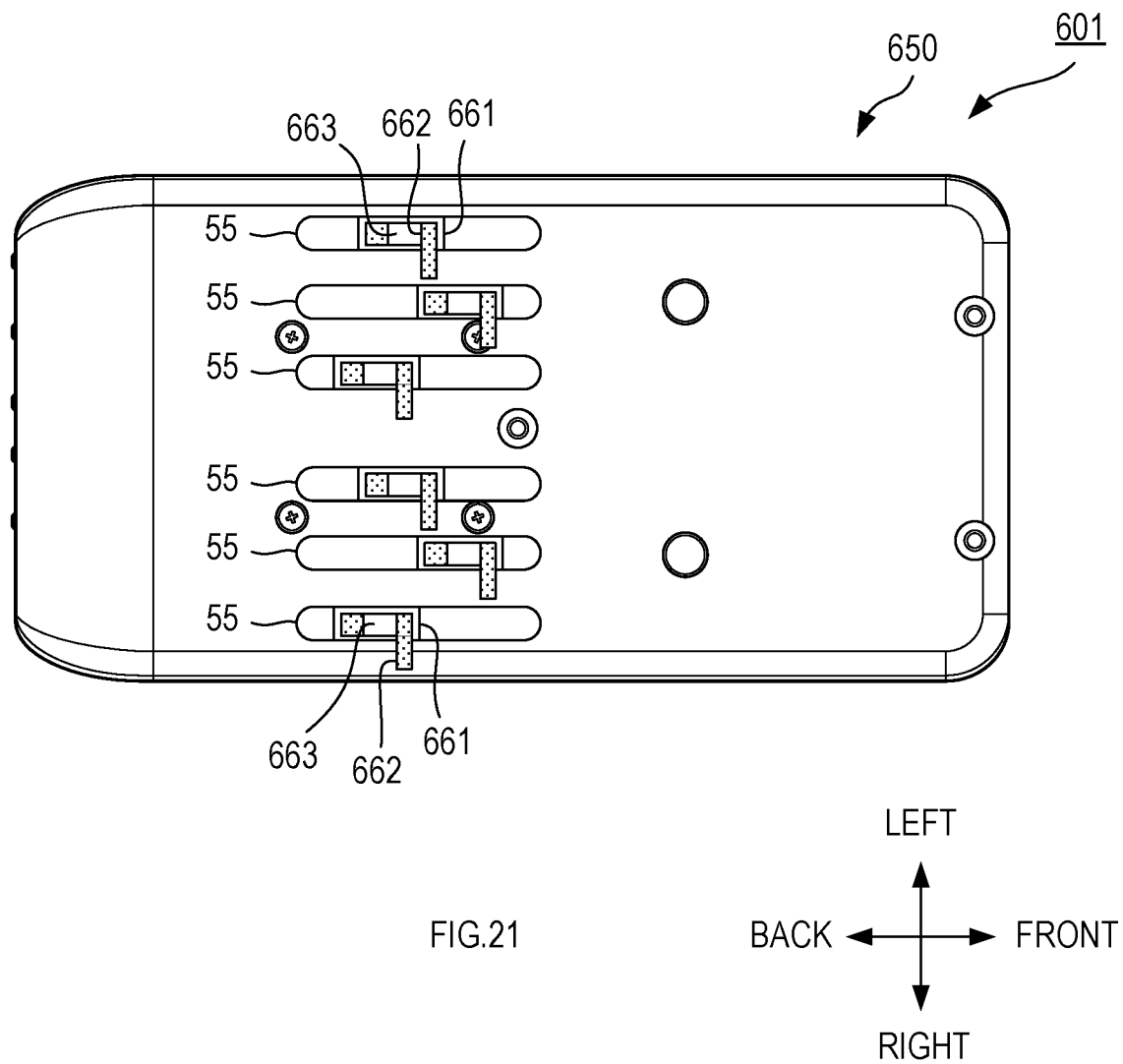
FIG. 21 is a schematic diagram illustrating a configuration of a motive power transmission adapter of the medical manipulator according to the seventh embodiment of the present disclosure.

As shown in FIG. 21, each of power transmission portions 661 of the motive power transmission adapter 650 in the medical manipulator system 601 includes a first drive abutment surface 662 and a first drive holding portion 663.

The first drive abutment surface 662 is a member which protrudes from a surface of the power transmission portion 661 facing the power unit 630 toward the power unit 630 and is formed in a plate shape extending in the right-left direction. In the first drive abutment surface 662, one end portion has a shape which protrudes in the right-left direction from the unclean surface slit 55.

The first drive holding portion 663 has a concave-shaped portion which is formed to be adjacent to the first drive abutment surface 662. The first drive holding portion 663 holds the drive engagement portion 636 inside the concave-shaped portion. The first drive holding portion 663 is a member which is formed to extend in the front-rear direction. The first drive abutment surface 662 is disposed on a forward end portion of the first drive holding portion 663, a convex shape protruding toward the power unit 630 is formed on a rearward end portion of the first drive holding portion 663, and the above-described concave-shaped portion is formed in the center of the first drive holding portion 663. In the concave-shaped portion of the first drive holding portion 663, end portions thereof in the right-left direction are open, and thus, the drive engagement portion 636 can move into or move out of the concave-shaped portion in the right-left direction.

Attachment and detachment of the motive power transmission adapter 650 and the power unit 630 in the medical manipulator system 601 having the above-described configurations are similar to those of the sixth embodiment, and thus, descriptions thereof are omitted.

According to the medical manipulator system 601 and the motive power transmission adapter 650 having the above-described configurations, the first drive abutment surface 662 is provided, and thus, it is possible to regulate the position of the power unit 630 when the power unit 630 is attached to the motive power transmission adapter 650. Therefore, the power transmission portion 661 and the power unit 630 easily engage with each other, and thus, workability is easily improved when the power unit 630 is attached to the motive power transmission adapter 650.

The first drive holding portion 663 is provided, and thus, it is possible to transmit the movement in both directions in the linear motion direction between the power transmission portion 661 and the drive portion 635, that is, in the forward direction and the rearward direction. Since the engagement state between the power transmission portion 661 and the drive portion 635 is maintained, controllability of the medical manipulator system 601 easily increases, and safety is easily secured in surgery.

[Eighth Embodiment]

Next, an eighth embodiment of the present disclosure will be described with reference to FIG. 22A. Basic configurations of a medical manipulator system and a motive power transmission adapter of the eighth embodiment are similar to those of the first embodiment. However, a shape of a drive portion of a power unit and a shape of a clean-side engagement portion of the power transmission portion of the eighth embodiment are different from those of the first embodiment. Accordingly, in the eighth embodiment, only the shape of the drive portion of the power unit, the shape of the clean-side engagement portion of the motive power transmission adapter, or the like will be described with reference to FIG. 22A, and descriptions of other configurations or the like are omitted.

Figure 22A:
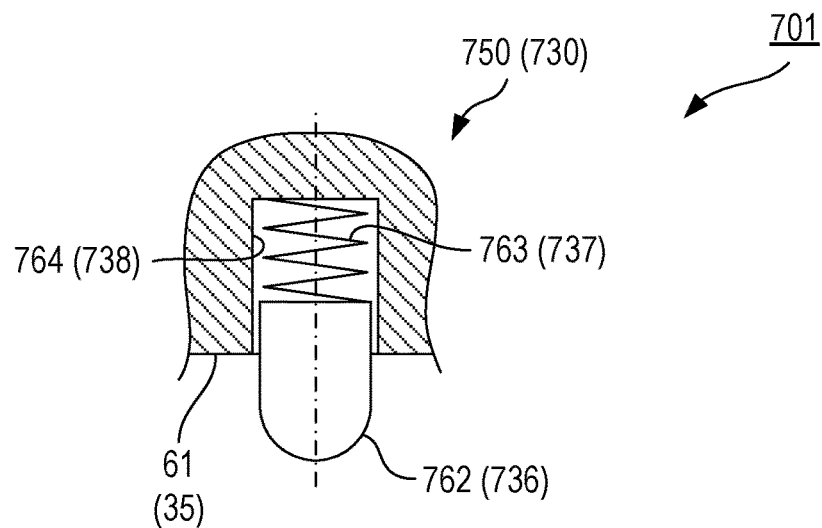
FIG. 22A is a schematic diagram illustrating a shape of a drive portion of a power unit and a shape of a clean-side engagement portion of a power transmission portion of a medical manipulator according to an eighth embodiment of the present disclosure.

As shown in FIG. 22A, the power transmission portion 61 of a motive power transmission adapter 750 in a medical manipulator system 701 of the eighth embodiment includes a clean-side engagement portion 762 and a first elastic portion 763. The clean-side engagement portion 762 corresponds to an example of a first engagement convex portion.

The clean-side engagement portion 762 is a member which is accommodated in a concave portion 764 which is formed on a surface of the power transmission portion 61 on the clean surface 52 side, and is a columnar member which is disposed so as to be able to protrude toward a surgical tool 10 and to be retracted from the surgical tool 10. The clean-side engagement portion 762 is a member which engages with the driven-side engagement portion 14.

The first elastic portion 763 is a spring member which is disposed between a bottom surface of the concave portion 764 which is formed on a surface of the power transmission portion 61 on the clean surface 52 side and the clean-side engagement portion 762. In the eighth embodiment, an example in which the first elastic portion 763 is a spring member formed of a metal material is described. However, the present invention is not limited to this. For example, the first elastic portion 763 may be a member formed of a resin such as a rubber as long as it can generate a force pressing the clean-side engagement portion 762 to the driven-side engagement portion 14 and can support the clean-side engagement portion 762 to be retractable toward the concave portion 764 according to the external force.

As shown in FIG. 22A, the drive portion 35 of a power unit 730 in the medical manipulator system 701 of the eighth embodiment includes a drive-side engagement portion 736 and a second elastic portion 737. The drive-side engagement portion 736 corresponds to an example of a second engagement convex portion.

The drive-side engagement portion 736 is a member which is accommodated in a concave portion 738 formed on a surface of the drive portion 35 on the motive power transmission adapter 750 side and is a columnar member which is disposed to be able to protrude toward the motive power transmission adapter 750 and to be retractable from the motive power transmission adapter 750. The drive-side engagement portion 736 is a member which engages with the unclean-side engagement portion 63.

The second elastic portion 737 is a spring member which is disposed between a bottom surface of the concave portion 738 which is formed on a surface of the drive portion 35 on the motive power transmission adapter 750 side and the drive-side engagement portion 736. In the eighth embodiment, an example in which the second elastic portion 737 is a spring member formed of a metal material is described. However, the present invention is not limited to this. For example, the second elastic portion 737 may be a member formed of a resin such as a rubber as long as it can generate a force pressing the drive-side engagement portion 736 to the unclean-side engagement portion 63 and can support the drive-side engagement portion 736 to be retractable toward the concave portion 738 according to the external force.

According to the medical manipulator system 701 and the motive power transmission adapter 750 having the above-described configurations, the clean-side engagement portion 762 and the first elastic portion 763 are provided, and thus, the surgical tool 10 is easily attached to the motive power transmission adapter 750. That is, when the surgical tool 10 is attached, the first elastic portion 763 is deformed and the clean-side engagement portion 762 can be retracted into the concave portion 764 or can protrude from the concave portion 764, and thus, the clean-side engagement portion 762 can easily engage with the driven portion 13. Moreover, the clean-side engagement portion 762 is pressed onto the driven portion 13 by a biasing force generated by the deformation of the first elastic portion 763, and thus, the engagement between the clean-side engagement portion 762 and the driven portion 13 is not easily released.

The drive-side engagement portion 736 and the second elastic portion 737 are provided, and thus, the power unit 730 is easily attached to the motive power transmission adapter 750. That is, when the power unit 730 is attached, the second elastic portion 737 is deformed, and thus, the drive-side engagement portion 736 easily engages with the power transmission portion 61. Moreover, the drive-side engagement portion 736 is pressed onto the power transmission portion 61 by a biasing force generated by the deformation of the second elastic portion 737, and thus, the engagement between the drive-side engagement portion 736 and the power transmission portion 61 is not easily released.

Moreover, in the above-described embodiment, the example is described, in which the clean-side engagement portion 762 which is the first engagement convex portion and the first elastic portion 763 are provided on the clean surface 52 side of the power transmission portion 61. However, the first engagement convex portion and the first elastic portion may be provided on the unclean surface 53 side of the power transmission portion 61. In this case, a concave portion which engages with the first engagement convex portion may be provided in the drive portion 35 instead of the drive-side engagement portion 36.

Moreover, in the above-described embodiment, the example is described, in which the drive-side engagement portion 736 which is the second engagement convex portion and the second elastic portion 737 are provided in the drive portion 35. However, the second engagement convex portion and the second elastic portion may be provided in the driven portion 13. In this case, a concave portion which engages with the second engagement convex portion may be provided in the power transmission portion 61.

[First Modification Example of Eighth Embodiment]

Next, a first modification example of the eighth embodiment of the present disclosure will be described with reference to FIG. 22B. Basic configurations of a medical manipulator system and a motive power transmission adapter of the first modification example are similar to those of the eighth embodiment. However, a shape of a drive portion of a power unit and a shape of a clean-side engagement portion of a power transmission portion of the first modification example are different from those of the eighth embodiment. Accordingly, in the first modification example, only the shape of the drive portion of the power unit, the shape of the clean-side engagement portion of the power transmission portion, or the like will be described with reference to FIG. 22B, and descriptions of other configurations or the like are omitted.

Figure 22B:
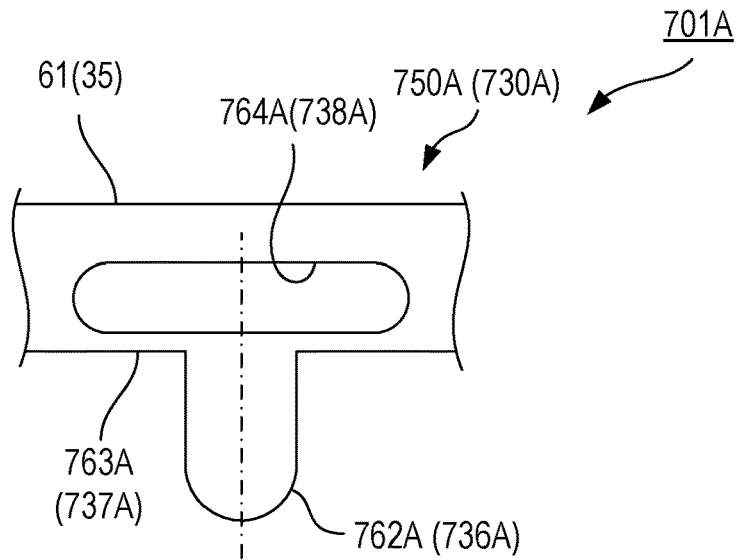
FIG. 22B is a schematic diagram illustrating another shape of the drive portion of the power unit and another shape of the clean-side engagement portion of the power transmission portion.

As shown in FIG. 22B, the power transmission portion 61 of a motive power transmission adapter 750A in a medical manipulator system 701A of the first modification example includes a clean-side engagement portion 762A and a first elastic portion 763A. The clean-side engagement portion 762A corresponds to an example of the first engagement convex portion.

The clean-side engagement portion 762A is a columnar member which is formed on a surface of the power transmission portion 61 on the clean surface 52 side and protrudes toward the surgical tool 10. The clean-side engagement portion 762A is a member which engages with the driven-side engagement portion 14.

The first elastic portion 763A is a member, which connects the power transmission portion 61 and the clean-side engagement portion 762A to each other, has elasticity, is formed in a beam shape or a thin film shape, and constitutes a wall surface of a space 764A provided in the power transmission portion 61.

In the first modification example, an example is described, in which the first elastic portion 763A is integrally formed of the same material as those of the power transmission portion 61 and the clean-side engagement portion 762A. However, the first elastic portion 763A may be formed of a material different from those of the power transmission portion 61 and the clean-side engagement portion 762A and may be separately formed from the power transmission portion 61 and the clean-side engagement portion 762A.

As shown in FIG. 22B, the drive portion 35 of a power unit 730A in the medical manipulator system 701A of the first modification example includes a drive-side engagement portion (second engagement convex portion) 736A and a second elastic portion 737A.

The drive-side engagement portion 736A is a columnar member which is formed on a surface of the drive portion 35 on the motive power transmission adapter 750 side and protrudes toward the motive power transmission adapter 750. The drive-side engagement portion 736A is a member which engages with the unclean-side engagement portion 63.

The second elastic portion 737A is a member which connects the drive portion 35 and the drive-side engagement portion 736A to each other, has elasticity, and is formed in a beam shape or a thin film shape, and constitutes a wall surface of a space 738A provided in the drive portion 35.

In the first modification example, an example is described, in which the second elastic portion 737A is integrally formed of the same material as those of the drive portion 35 and the drive-side engagement portion 736A. However, the second elastic portion 737A may be formed of a material different from those of the drive portion 35 and the drive-side engagement portion 736A and may be separately formed from the drive portion 35 and the drive-side engagement portion 736A.

According to the medical manipulator system 701A and the motive power transmission adapter 750A having the above-described configurations, the clean-side engagement portion 762A and the first elastic portion 763A are provided, and thus, the surgical tool 10 is easily attached to the motive power transmission adapter 750A. That is, when the surgical tool 10 is attached, the first elastic portion 763A is deformed and the clean-side engagement portion 762A can be pushed in or can protrude, and thus, the clean-side engagement portion 762A can easily engage with the driven portion 13. Moreover, the clean-side engagement portion 762A is pressed onto the driven portion 13 by a biasing force generated by the deformation of the first elastic portion 763A, and thus, the engagement between the clean-side engagement portion 762A and the driven portion 13 is not easily released.

The drive-side engagement portion 736A and the second elastic portion 737A are provided, and thus, the power unit 730A is easily attached to the motive power transmission adapter 750A. That is, when the power unit 730A is attached, the second elastic portion 737A is deformed, and thus, the drive-side engagement portion 736A easily engages with the power transmission portion 61A. Moreover, the drive-side engagement portion 736A is pressed onto the power transmission portion 61 by a biasing force generated by the deformation of the second elastic portion 737A, and thus, the engagement between the drive-side engagement portion 736A and the power transmission portion 61A is not easily released.

Moreover, in the above-described modification example, the example is described, in which the clean-side engagement portion 762A which is the first engagement convex portion and the first elastic portion 763A are provided on the clean surface 52 side of the power transmission portion 61. However, the first engagement convex portion and the first elastic portion may be provided on the unclean surface 53 side of the power transmission portion 61. In this case, a concave portion which engages with the first engagement convex portion may be provided in the drive portion 35 instead of the drive-side engagement portion 36.

Moreover, in the above-described modification example, the example is described, in which the drive-side engagement portion 736A which is the second engagement convex portion and the second elastic portion 737A are provided in the drive portion 35. However, the second engagement convex portion and the second elastic portion may be provided in the driven portion 13. In this case, a concave portion which engages with the second engagement convex portion may be provided in the power transmission portion 61.

[Second Modification Example of Eighth Embodiment]

Next, a second modification example of the eighth embodiment of the present disclosure will be described with reference to FIG. 22C. Basic configurations of a medical manipulator system and a motive power transmission adapter of the second modification example are similar to those of the eighth embodiment. However, a shape of a drive portion of a power unit and a shape of a clean-side engagement portion of a power transmission portion of the second modification example are different from those of the eighth embodiment. Accordingly, in the second modification example, only the shape of the drive portion of the power unit, the shape of the clean-side engagement portion of the power transmission portion, or the like will be described with reference to FIG. 22C, and descriptions of other configurations or the like are omitted.

Figure 22C:
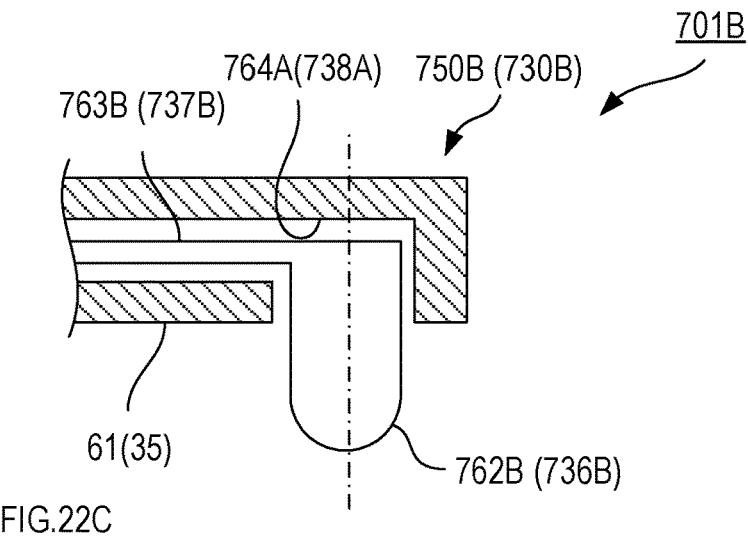
FIG. 22C is a schematic diagram illustrating still another shape of the drive portion of the power unit and still another shape of the clean-side engagement portion of the power transmission portion.

As shown in FIG. 22C, the power transmission portion 61 of a motive power transmission adapter 750B in a medical manipulator system 701B of the second modification example includes a clean-side engagement portion 762B and a first elastic portion 763B. The clean-side engagement portion 762B corresponds to an example of the first engagement convex portion.

The clean-side engagement portion 762B is a member which is accommodated in an internal space 738B having an opening on a surface of the drive portion 35 on the motive power transmission adapter 750B side, and is a columnar member which is disposed to be able to protrude toward or to be retracted from the motive power transmission adapter 750B. The clean-side engagement portion 762B is a member which engages with the driven-side engagement portion 14.

The first elastic portion 763B is a member which is disposed between a side of the internal space 738B of the power transmission portion 61 and the clean-side engagement portion 762B and is formed in a beam shape. In the second modification example, an example is described, in which the first elastic portion 763B is integrally formed of the same material as that of the clean-side engagement portion 762B. However, the first elastic portion 763B may be formed of a material different from that of the clean-side engagement portion 762B and may be separately formed from the clean-side engagement portion 762B.

As shown in FIG. 22C, the drive portion 35 of a power unit 730B in the medical manipulator system 701B of the second modification example includes a drive-side engagement portion 736B and a second elastic portion 737B. The drive-side engagement portion 736B corresponds to an example of the second engagement convex portion.

The drive-side engagement portion 736B is a member which is accommodated in an internal space 738B having an opening on a surface of the drive portion 35 on the motive power transmission adapter 750B side, and is a columnar member which is disposed to be able to protrude toward or to be retracted from the motive power transmission adapter 750B. The drive-side engagement portion 736B is a member which engages with the unclean-side engagement portion 63.

The second elastic portion 737B is a member which is disposed between the internal space 738B of the drive portion 35 and the drive-side engagement portion 736B and is formed in a beam shape. In the second modification example, an example is described, in which the second elastic portion 737B is integrally formed of the same material as that of the drive-side engagement portion 736B. However, the second elastic portion 737B may be formed of a material different from that of the drive-side engagement portion 736B and may be separately formed from the drive-side engagement portion 736B.

According to the medical manipulator system 701B and the motive power transmission adapter 750B having the above-described configurations, the clean-side engagement portion 762B and the first elastic portion 763B are provided, and thus, the surgical tool 10 is easily attached to the motive power transmission adapter 750B. That is, when the surgical tool 10 is attached, the first elastic portion 763B is deformed and the clean-side engagement portion 762B can be pushed in or can protrude, and thus, the clean-side engagement portion 762B can easily engage with the driven portion 13. Moreover, the clean-side engagement portion 762B is pressed onto the driven portion 13 by a biasing force generated by the deformation of the first elastic portion 763B, and thus, the engagement between the clean-side engagement portion 762B and the driven portion 13 is not easily released.

The drive-side engagement portion 736B and the second elastic portion 737B are provided, and thus, the power unit 730B is easily attached to the motive power transmission adapter 750B. That is, when the power unit 730B is attached, the second elastic portion 737B is deformed, and thus, the drive-side engagement portion 736B easily engages with the power transmission portion 61B. Moreover, the drive-side engagement portion 736B is pressed onto the power transmission portion 61 by a biasing force generated by the deformation of the second elastic portion 737B, and thus, the engagement between the drive-side engagement portion 736B and the power transmission portion 61B is not easily released.

Moreover, in the above-described modification example, the example is described, in which the clean-side engagement portion 762B which is the first engagement convex portion and the first elastic portion 763B are provided on the clean surface 52 side of the power transmission portion 61. However, the first engagement convex portion and the first elastic portion may be provided on the unclean surface 53 side of the power transmission portion 61. In this case, a concave portion which engages with the first engagement convex portion may be provided in the drive portion 35 instead of the drive-side engagement portion 36.

Moreover, in the above-described modification example, the example is described, in which the drive-side engagement portion 736B which is the second engagement convex portion and the second elastic portion 737B are provided in the drive portion 35. However, the second engagement convex portion and the second elastic portion may be provided in the driven portion 13. In this case, a concave portion which engages with the second engagement convex portion may be provided in the power transmission portion 61.

[Third Modification Example of Eighth Embodiment]

Next, a third modification example of the eighth embodiment of the present disclosure will be described with reference to FIG. 23A. Basic configurations of a medical manipulator system and a motive power transmission adapter of the third modification example are similar to those of the first modification example of the eighth embodiment. However, a shape of a drive portion of a power unit and a shape of a clean-side engagement portion of a power transmission portion of the third modification example are different from those of the eighth embodiment. Accordingly, in the third modification example, only the shape of the drive portion of the power unit, the shape of the clean-side engagement portion of the power transmission portion, or the like will be described with reference to FIG. 23A, and descriptions of other configurations or the like are omitted.

Figure 23A:
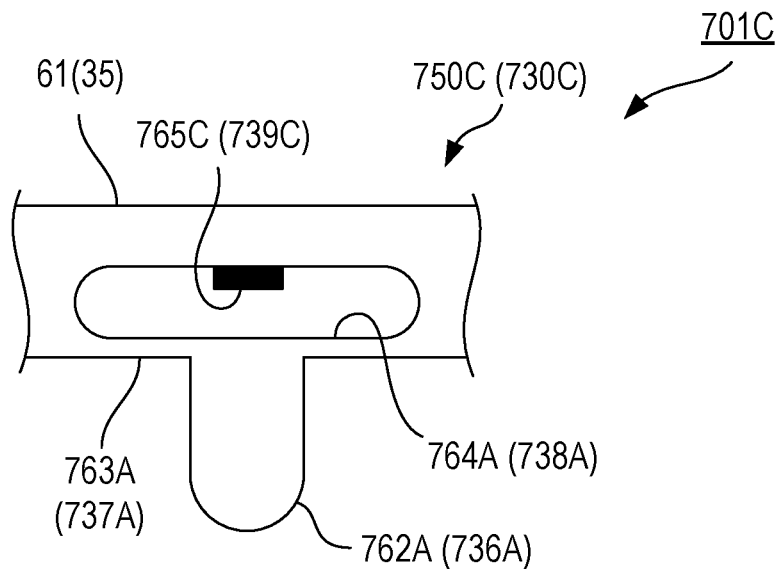
FIG. 23A is a schematic diagram illustrating still another shape of the drive portion of the power unit and still another shape of the clean-side engagement portion of the power transmission portion.

As shown in FIG. 23A, the power transmission portion 61 of a motive power transmission adapter 750C in a medical manipulator system 701C of the third modification example includes the clean-side engagement portion 762A, the first elastic portion 763A, and a first detection unit 765C.

The first detection unit 765C detects a movement of the clean-side engagement portion 762A generated by elastic deformation of the first elastic portion 763A. The first detection unit 765C is an inner surface of the space 764A and is disposed in a region facing a region in which the clean-side engagement portion 762A is provided. For example, a signal indicating the movement of the clean-side engagement portion 762A detected by the first detection unit 765C is output to an external control unit.

A method of detecting the movement of the clean-side engagement portion 762A by the first detection unit 765C can use a known method. For example, the method includes a method of detecting that the region of the space 764A facing the first detection unit 765C comes into contact with the first detection unit 765C by the elastic deformation of the first elastic portion 763A, a method of detecting the elastic deformation of the first elastic portion 763A, or the like.

As shown in FIG. 23A, the drive portion 35 of the power unit 730C in a medical manipulator system 701C of the third modification example includes the drive-side engagement portion 736A, the second elastic portion 737A, and a second detection unit 739C.

The second detection unit 739C detects a movement of the drive-side engagement portion 736A generated by elastic deformation of the second elastic portion 737A. The second detection unit 739C is the inner surface of the space 738A and is disposed in a region facing a region in which the drive-side engagement portion 736A is provided. For example, a signal indicating the movement of the drive-side engagement portion 736A detected by the second detection unit 739C is output to an external control unit.

As a method of detecting the movement of the drive-side engagement portion 736A by the second detection unit 739C, a known method can be used. Examples of the method include a method of detecting that the region of the space 738A facing the second detection unit 739C comes into contact with the second detection unit 739C by the elastic deformation of the second elastic portion 737A, a method of detecting the elastic deformation of the second elastic portion 737A, and the like.

According to the medical manipulator system 701C and the motive power transmission adapter 750C having the above-described configurations, the first detection unit 765C is provided, and thus, it is possible to detect the movement of the clean-side engagement portion 762A by the elastic deformation of the first elastic portion 763A. Accordingly, when the surgical tool 10 is attached, it is possible to detect a movement such as protrusion or retraction of the clean-side engagement portion 762A, and the surgical tool 10 is reliably attached to the motive power transmission adapter 750C easily.

According to the medical manipulator system 701C and the motive power transmission adapter 750C having the above-described configurations, the second detection unit 739C is provided, and thus, it is possible to detect the movement of the drive-side engagement portion 736A by the elastic deformation of the second elastic portion 737A. Accordingly, when the power unit 730C is attached, it is possible to detect a movement such as protrusion or retraction of the drive-side engagement portion 736A, and the power unit 730C is reliably attached to the motive power transmission adapter 750C easily.

[Fourth Modification Example of Eighth Embodiment]

Next, a fourth modification example of the eighth embodiment of the present disclosure will be described with reference to FIG. 23B. Basic configurations of a medical manipulator system and a motive power transmission adapter of the fourth modification example are similar to those of the eighth embodiment. However, a shape of a drive portion of a power unit and a shape of a clean-side engagement portion of a power transmission portion of the fourth modification example are different from those of the eighth embodiment. Accordingly, in the fourth modification example, only the shape of the drive portion of the power unit, the shape of the clean-side engagement portion of the power transmission portion, or the like will be described with reference to FIG. 23B, and descriptions of other configurations or the like are omitted.

Figure 23B:
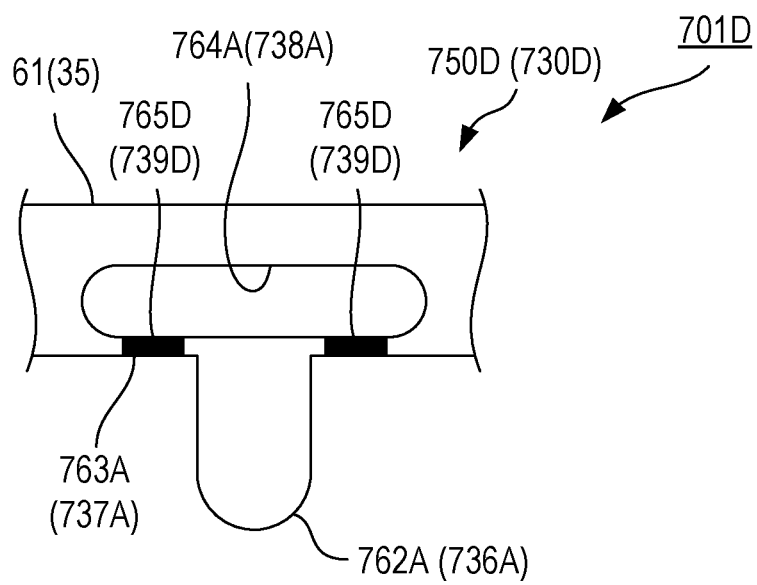
FIG. 23B is a schematic diagram illustrating still another shape of the drive portion of the power unit and still another shape of the clean-side engagement portion of the power transmission portion.

As shown in FIG. 23B, the power transmission portion 61 of a motive power transmission adapter 750D in a medical manipulator system 701D of the fourth modification example includes the clean-side engagement portion 762A, the first elastic portion 763A, and a first detection unit 765D.

The first detection unit 765D detects the movement of the clean-side engagement portion 762A generated by elastic deformation of the first elastic portion 763D. The first detection unit 765D is disposed in any one of an inner surface, an outer surface, and an inside of the first elastic portion 763D. For example, a signal indicating the movement of the clean-side engagement portion 762A detected by the first detection unit 765D is output to an external control unit.

As a method of detecting the movement of the clean-side engagement portion 762A by the first detection unit 765D, a known method such as a method of detecting the elastic deformation of the first elastic portion 763A can be used. Moreover, in the fourth modification example, an example in which two first detection units 765D are provided is described. However, the number of the first detection units 765D may be one or greater than two.

As shown in FIG. 23A, the drive portion 35 of the power unit 730D in a medical manipulator system 701D of the fourth modification example includes the drive-side engagement portion 736A, the second elastic portion 737A, and a second detection unit 739D.

The second detection unit 739D detects the movement of the drive-side engagement portion 736A generated by the elastic deformation of the second elastic portion 737A. The second detection unit 739D is disposed in any one of an inner surface, an outer surface, and an inside of the second elastic portion 737A. For example, a signal indicating the movement of the drive-side engagement portion 736A detected by the second detection unit 739D is output to an external control unit.

As a method of detecting the movement of the drive-side engagement portion 736A by the second detection unit 739D, a known method such as a method of detecting the elastic deformation of the second elastic portion 737A can be used. Moreover, in the fourth modification example, an example in which two second detection units 739D are provided is described. However, the number of the second detection units 739D may be one or greater than two.

According to the medical manipulator system 701D and the motive power transmission adapter 750D having the above-described configurations, the first detection unit 765D is provided, and thus, it is possible to detect the movement of the clean-side engagement portion 762A by the elastic deformation of the first elastic portion 763A. Accordingly, when the surgical tool 10 is attached, it is possible to detect a movement such as protrusion or retraction of the clean-side engagement portion 762A, and the surgical tool 10 is reliably attached to the motive power transmission adapter 750D easily.

According to the medical manipulator system 701D and the motive power transmission adapter 750D having the above-described configurations, the second detection unit 739D is provided, and thus, it is possible to detect the movement of the drive-side engagement portion 736A by the elastic deformation of the second elastic portion 737A. Accordingly, when the power unit 730D is attached, it is possible to detect a movement such as protrusion or retraction of the drive-side engagement portion 736A, and the power unit 730D is reliably attached to the motive power transmission adapter 750D easily.

[Fifth Modification Example of Eighth Embodiment]

Next, a fifth modification example of the eighth embodiment of the present disclosure will be described with reference to FIG. 24A. Basic configurations of a medical manipulator system and a motive power transmission adapter of the fifth modification example are similar to those of the eighth embodiment. However, shapes of attachment portions of a power unit and the motive power transmission adapter of the fifth modification example are different from those of the eighth embodiment. Accordingly, in the fifth modification example, only peripheries of the attachment portions of the power unit and the motive power transmission adapter will be described with reference to FIG. 24A, and descriptions of other configurations or the like are omitted.

Figure 24A:
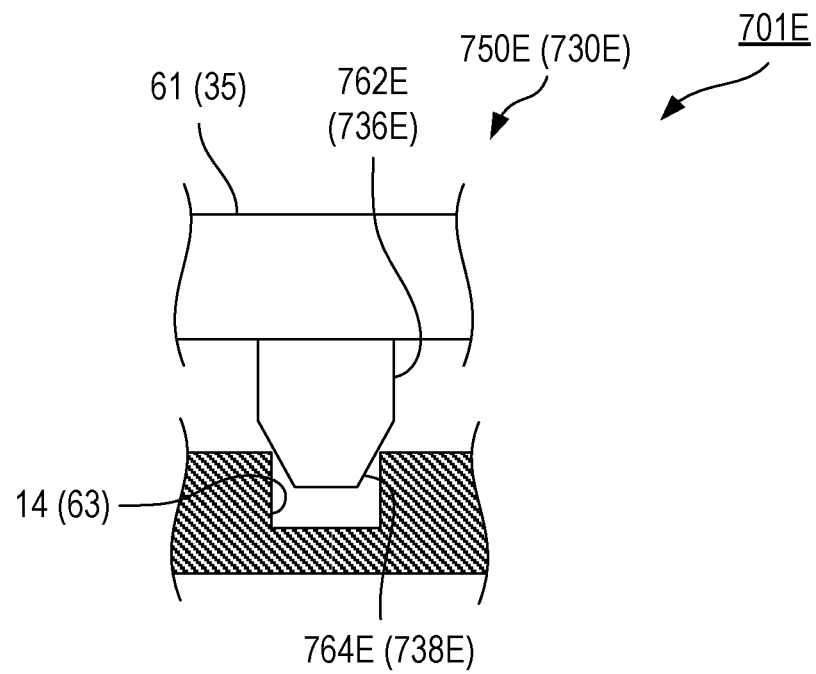
FIG. 24A is a schematic diagram illustrating still another shape of the drive portion of the power unit and still another shape of the clean-side engagement portion of the power transmission portion.

As shown in FIG. 24A, the power transmission portion 61 of a motive power transmission adapter 750E in a medical manipulator system 701E of the fifth modification example includes a clean-side engagement portion (first engagement convex portion) 762E and the first elastic portion 763 (refer to FIG. 22A).

The clean-side engagement portion 762E is a columnar member which is disposed to be able to protrude or to be retracted from a surface of the power transmission portion 61 on the clean surface 52 side toward the surgical tool 10. The clean-side engagement portion 762E is a member which engages with the driven-side engagement portion 14. The clean-side engagement portion 762E includes a first inclined surface 764E in which a cross-sectional area of the clean-side engagement portion 762E gradually increases from a distal end of the clean-side engagement portion 762E toward a root thereof.

As shown in FIG. 24A, the drive portion 35 of a power unit 730E in the medical manipulator system 701E of the fifth modification example includes a drive-side engagement portion 736E and the second elastic portion 737 (refer to FIG. 22A). The drive-side engagement portion 736E corresponds to an example of the second engagement convex portion.

The drive-side engagement portion 736E is a columnar member which is disposed to be able to protrude or to be retracted from a surface of the drive portion 35 on the motive power transmission adapter 750 side toward the motive power transmission adapter 750E. The drive-side engagement portion 736E is a member which engages with the unclean-side engagement portion 63.

The drive-side engagement portion 736E includes a second inclined surface 738E in which a cross-sectional area of the drive-side engagement portion 736E gradually increases from a distal end of the drive-side engagement portion 736E toward a root thereof.

According to the medical manipulator system 701E and the motive power transmission adapter 750E having the above-described configurations, the first inclined surface 764E is provided in the clean-side engagement portion 762E. Accordingly, compared to a case where the first inclined surface 764E is not provided, a gap (rattling) generated when the clean-side engagement portion 762E engages with the driven-side engagement portion 14 of the driven portion 13 is easily suppressed.

According to the medical manipulator system 701E and the motive power transmission adapter 750E having the above-described configurations, the second inclined surface 738E is provided in the drive-side engagement portion 736E. Accordingly, compared to a case where the second inclined surface 738E is not provided, a gap (rattling) generated when the drive-side engagement portion 736E engages with the unclean-side engagement portion 63 of the power transmission portion 61 is easily suppressed.

Moreover, in the above-described fifth modification example, the example in which the clean-side engagement portion 762E which is the first engagement convex portion is provided on the clean surface 52 side of the power transmission portion 61 is described. However, the first engagement convex portion may be provided on the unclean surface 53 side of the power transmission portion 61. In this case, a concave portion which engages with the first engagement convex portion may be provided in the drive portion 35 instead of the drive-side engagement portion 36.

Moreover, in the above-described fifth modification example, the example is described, in which the drive-side engagement portion 736E which is the second engagement convex portion is provided in the drive portion 35. However, the second engagement convex portion may be provided in the driven portion 13. In this case, a concave portion which engages with the second engagement convex portion may be provided in the power transmission portion 61.

[Sixth Modification Example of Eighth Embodiment]

Next, a sixth modification example of the eighth embodiment of the present disclosure will be described with reference to FIG. 24B. Basic configurations of a medical manipulator system and a motive power transmission adapter of the sixth modification example are similar to those of the eighth embodiment. However, shapes of attachment portions of a power unit and the motive power transmission adapter of the sixth modification example are different from those of the eighth embodiment. Accordingly, in the sixth modification example, only peripheries of the attachment portions of the power unit and the motive power transmission adapter or the like will be described with reference to FIG. 24B, and descriptions of other configurations or the like are omitted.

Figure 24B:
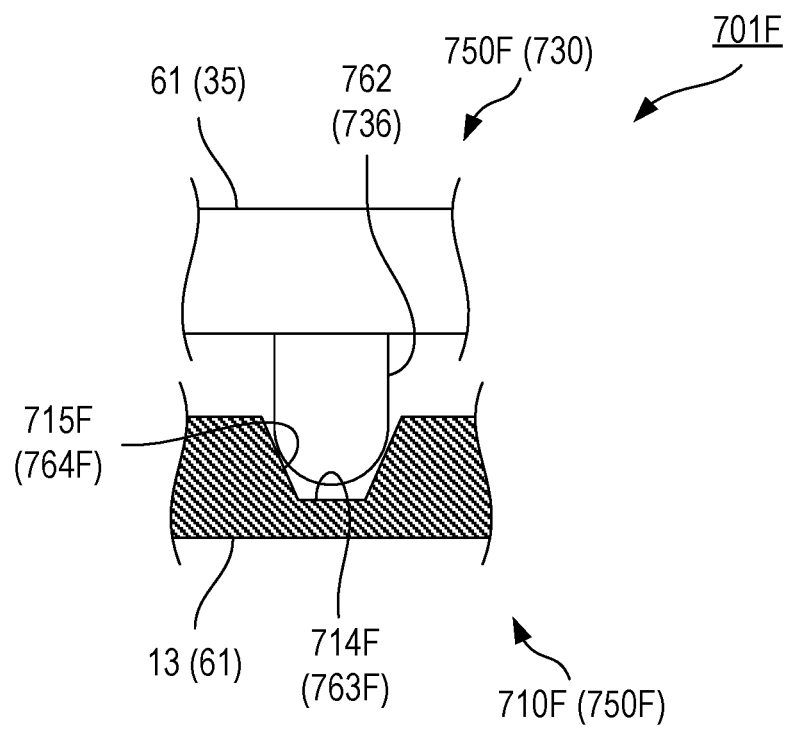
FIG. 24B is a schematic diagram illustrating still another shape of the drive portion of the power unit and still another shape of the clean-side engagement portion of the power transmission portion.

As shown in FIG. 24B, the power transmission portion 61 of a motive power transmission adapter 750F in a medical manipulator system 701F of the sixth modification example includes a clean-side engagement portion 762 and the first elastic portion 763 (refer to FIG. 22A).

The driven portion 13 in a surgical tool 710F includes a driven-side engagement portion (second engagement concave portion) 714F which engages with the clean-side engagement portion 762. The driven-side engagement portion 714F includes a second inclined surface 715F in which an opening area of the driven-side engagement portion 714F increases from a bottom surface toward an opening.

As shown in FIG. 24B, the drive portion 35 of the power unit 730 in the medical manipulator system 701F of the sixth modification example includes the drive-side engagement portion 736 and the second elastic portion 737 (refer to FIG. 22A).

The power transmission portion 61 of the motive power transmission adapter 750F includes an unclean-side engagement portion (first engagement concave portion) 763F which engages with the drive-side engagement portion 736. The unclean-side engagement portion 763F includes a first inclined surface 764F in which an opening area of the unclean-side engagement portion 763F increases from a bottom surface toward an opening.

According to the medical manipulator system 701E and the motive power transmission adapter 750E having the above-described configurations, the first inclined surface 764F is provided in the unclean-side engagement portion 763F. Accordingly, compared to a case where the first inclined surface 764F is not provided, a gap (rattling) generated when the unclean-side engagement portion 763F engages with the drive portion 35 is easily suppressed.

According to the medical manipulator system 701E and the motive power transmission adapter 750E having the above-described configurations, the second inclined surface 715F is provided in the driven-side engagement portion 714F. Accordingly, compared to a case where the second inclined surface 715F is not provided, a gap (rattling) generated when the driven-side engagement portion 714F engages with the power transmission portion 61 is easily suppressed.

Moreover, in the above-described sixth modification example, the example is described, in which the unclean-side engagement portion 763F which is the first engagement convex portion engaging with the drive-side engagement portion 736 is provided in the power transmission portion 61. However, the first engagement convex portion may be provided on the unclean surface 53 side of the power transmission portion 61. In this case, a concave portion which engages with the first engagement convex portion may be provided in the drive portion 35 instead of the drive-side engagement portion 36.

Moreover, in the above-described sixth modification example, the example is described, in which the driven-side engagement portion 714F which is the second engagement convex portion is provided in the driven portion 13. However, the second engagement convex portion may be provided in the drive portion 35. In this case, the concave portion which engages with the second engagement convex portion may be provided in the power transmission portion 61.

[Ninth Embodiment]

Next, a ninth embodiment of the present disclosure will be described with reference to FIG. 25. Basic configurations of a medical manipulator system and a motive power transmission adapter of the ninth embodiment are similar to those of the first embodiment. However, a configuration for transmitting a driving force generated by an actuator unit in the ninth embodiment is different from that of the first embodiment. Accordingly, in the ninth embodiment, only a periphery of the configuration for transmitting the driving force generated by the actuator unit will be described with reference to FIG. 25, and descriptions of other configurations or the like are omitted.

Figure 25:
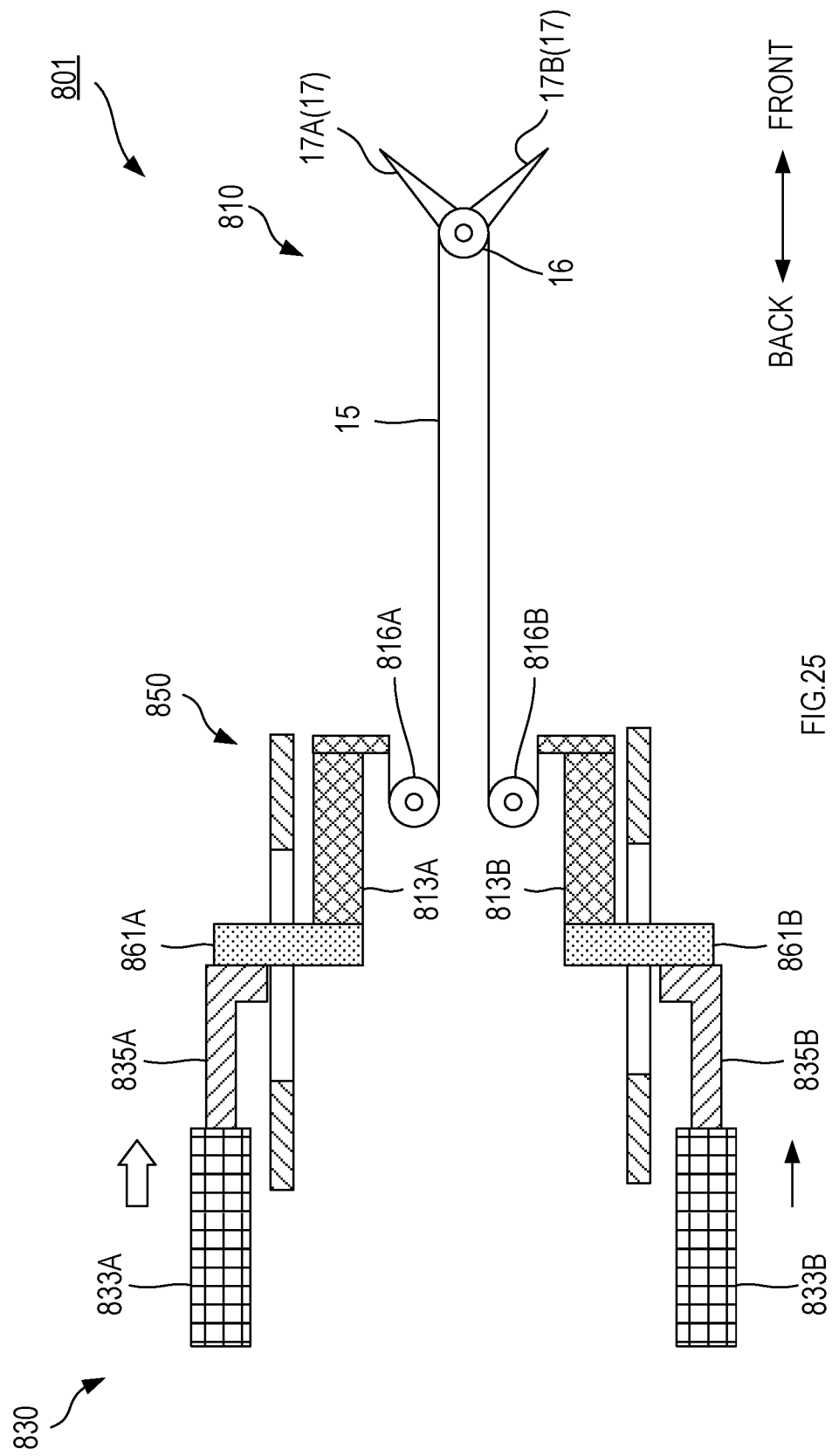
FIG. 25 is a schematic diagram illustrating a configuration of a medical manipulator according to a ninth embodiment of the present disclosure.

As shown in FIG. 25, a power unit 830 of a medical manipulator system 801 of the ninth embodiment includes a drive portion 835A, a drive portion 835B, an actuator unit 833A, and an actuator unit 833B.

Each of the drive portion 835A and the drive portion 835B is a rod-shaped member extending in a forward direction from each of the actuator unit 833A and the actuator unit 833B, and is a member formed in an approximately L shape which has a portion protruding in a direction intersecting the linear motion direction on a forward end portion.

The actuator unit 833A and the actuator unit 833B can push the drive portion 835A and the drive portion 835B in the forward direction (pushing direction) along the linear motion direction and can pull the drive portion 835A and the drive portion 835B in a rearward direction (pulling direction).

A surgical tool 810 includes a driven portion 813A and a driven portion 813B corresponding to the drive portion 835A and the drive portion 835B. Each of the driven portion 813A and the driven portion 813B is a rod-shaped member extending in a front-rear direction, and is a member formed in an approximately L shape which has a portion protruding in the direction intersecting the linear motion direction on a forward end portion. The wire 15 is attached to rear-side surfaces in protrusion portions of the driven portion 813A and the driven portion 813B.

The surgical tool 810 further includes a transmission pulley 816A and a transmission pulley 816B. The wire 15 extending rearward from the drive portion 835A and the drive portion 835B is wound around the transmission pulley 816A and the transmission pulley 816B, and thus, a direction is changed in the forward direction.

A motive power transmission adapter 850 includes at least a power transmission portion 861A and a power transmission portion 861B. Each of the power transmission portion 861A and the power transmission portion 861B is a rod-shaped member extending in the direction intersecting the linear motion direction and is disposed to be relatively movable in the linear motion direction.

In the power transmission portion 861A and the power transmission portion 861B, end portions on the power unit 830 side are disposed to abut against forward end portions of the drive portion 835A and the drive portion 835B, and the driving force in the forward direction is applied from the drive portion 835A and the drive portion 835B to the power transmission portion 861A and the power transmission portion 861B. Moreover, in the power transmission portion 861A and the power transmission portion 861B, end portions on the surgical tool 810 side are disposed to abut against rearward end portions of the driven portion 813A and the driven portion 813B, and the power transmission portion 861A and the power transmission portion 861B transmit the driving force in the forward direction to the driven portion 813A and the driven portion 813B.

Next, a movement of the medical manipulator system 801 having the above-described configuration will be described.

In a case where the forceps 17 is operated in the ninth embodiment, for example, the driving force is generated in the actuator unit 833A to push the drive portion 835A in the forward direction. The driving force in the forward direction of the drive portion 835A is transmitted to the driven portion 813A via the power transmission portion 861A. The driven portion 813A is moved in the forward direction, and thus, the wire 15 is pulled in the forward direction. The movement of the wire 15 is transmitted to the drive pulley 16 via the transmission pulley 816A, and thus, the movable piece 17A of the forceps 17 is moved.

In this case, the actuator unit 833B generates a biasing force for pressing the drive portion 835B in the forward direction. An abutment state between the drive portion 835B and the power transmission portion 861B and an abutment state between the power transmission portion 861B and the driven portion 813B are maintained by the biasing force.

According to the medical manipulator system 801 and the motive power transmission adapter 850 having the above-described configurations, in a case where the drive portion 835A is moved in the forward direction (pushing direction), the other drive portion 835B is biased in the forward direction (pushing direction), and thus, the contact state between the power transmission portion 861A and the driven portion 813A and the contact state where the power transmission portion 861B and the driven portion 813B are easily maintained. Specifically, even when an engagement structure between the power transmission portion 861A and the driven portion 813A and an engagement structure between the power transmission portion 861B and the driven portion 813B are simply configured, the contact state between the power transmission portion 861A and the driven portion 813A and the contact state between the power transmission portion 861B and the driven portion 813B can be maintained, and thus, the surgical tool 810 is easily attached to or detached from the motive power transmission adapter 850.

[Tenth Embodiment]

Next, a tenth embodiment of the present disclosure will be described with reference to FIG. 26. Basic configurations of a medical manipulator system and a motive power transmission adapter of the tenth embodiment are similar to those of the ninth embodiment. However, a configuration for transmitting a driving force generated by an actuator unit in the tenth embodiment is different from that of the ninth embodiment. Accordingly, in the tenth embodiment, only a periphery of the configuration for transmitting the driving force generated by the actuator unit will be described with reference to FIG. 26, and descriptions of other configurations or the like are omitted.

Figure 26:
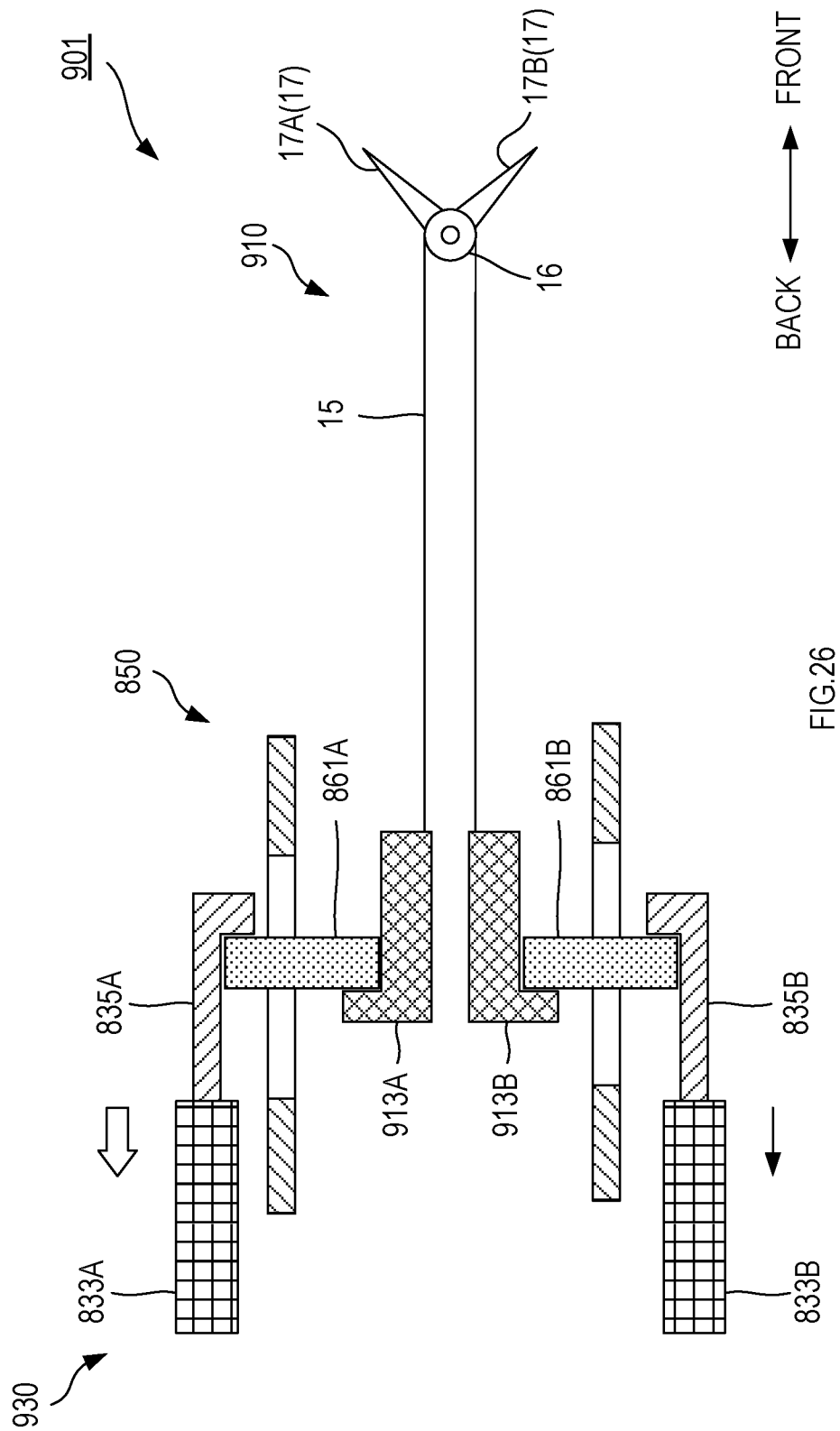
FIG. 26 is a schematic diagram illustrating a configuration of a medical manipulator according to a tenth embodiment of the present disclosure.

As shown in FIG. 26, a surgical tool 910 of a medical manipulator system 901 of the tenth embodiment includes a driven portion 913A and a driven portion 913B corresponding to the drive portion 835A and the drive portion 835B. Each of the driven portion 913A and the driven portion 913B is a rod-shaped member extending in a front-rear direction, and is a member formed in an approximately L shape which has a portion protruding in a direction intersecting the linear motion direction on a rearward end portion. The wire 15 is attached to forward end portions of the driven portion 913A and driven portion 913B.

In the power transmission portion 861A and the power transmission portion 861B of the motive power transmission adapter 850, end portions on a power unit 830 side are disposed to abut against the drive portion 835A and the drive portion 835B. More specifically, the end portions are disposed to abut against rearward facing surfaces of substantially L-shaped protrusions provided in the drive portion 835A and the drive portion 835B. Accordingly, a driving force in a rearward direction from the drive portion 835A and the drive portion 835B is applied to the power transmission portion 861A and the power transmission portion 861B.

Moreover, in the power transmission portion 861A and the power transmission portion 861B, end portions on the surgical tool 810 side are disposed to abut against the driven portion 913A and the driven portion 913B. More specifically, the end portions are disposed to abut against forward facing surfaces of substantially L-shaped protrusions provided in the driven portion 913A and the driven portion 913B. Accordingly, the power transmission portion 861A and the power transmission portion 861B can transmit the driving force in the rearward direction to the driven portion 813A and the driven portion 813B.

Next, a movement of the medical manipulator system 901 having the above-described configuration will be described.

In a case where the forceps 17 is operated in the tenth embodiment, for example, the driving force is generated in the actuator unit 833A to pull the drive portion 835A in the rearward direction. The driving force in the rearward direction of the drive portion 835A is transmitted to the driven portion 913A via the power transmission portion 861A. The driven portion 913A is moved in the forward direction, and thus, the wire 15 is pulled in the forward direction. The movement of the wire 15 is transmitted to the drive pulley 16, and thus, the movable piece 17A of the forceps 17 is moved.

In this case, the actuator unit 833B generates a biasing force for pulling the drive portion 835B in the rearward direction. The abutment state between the drive portion 835B and the power transmission portion 861B and the abutment state between the power transmission portion 861B and the driven portion 913B are maintained by the biasing force.

According to the medical manipulator system 901 and the motive power transmission adapter 850 having the above-described configuration, in a case where the drive portion 835A is moved in the rearward direction (pulling direction), the drive portion 835B is biased in the rearward direction (pulling direction), and thus, the contact state between the power transmission portion 861A and the driven portion 913A and the contact state between the power transmission portion 861B and the driven portion 913B are easily maintained. Specifically, even when an engagement structure between the power transmission portion 861A and the driven portion 913A and an engagement structure between the power transmission portion 861B and the driven portion 913B are simply configured, the contact state between the power transmission portion 861A and the driven portion 913A and the contact state between the power transmission portion 861B and the driven portion 913B can be maintained, and thus, the surgical tool 910 is easily attached to or detached from the motive power transmission adapter 850.

A technical scope of the present disclosure is not limited to the above-described embodiments, and various modifications can be made within a scope which does not depart from the gist of the present disclosure. For example, the present disclosure is not limited to application to the above-described embodiments and may be applied to an embodiment in which these embodiments are appropriately combined, and the application of the present disclosure is not particularly limited.

The invention claimed is:

1. A motive power transmission adapter comprising:
   a casing disposed between a surgical tool and a power unit for driving the surgical tool and comprising a clean surface, which is a surface facing the surgical tool disposed in a clean region, and an unclean surface, which is a surface facing the power unit disposed in an unclean region, the clean surface and the unclean surface being arranged to overlap each other with at least a part of the casing located between the clean surface and the unclean surface;
   a plurality of guide portions having a groove shape provided in the clean surface and the unclean surface of the casing, the plurality of guide portions extending along the clean surface and the unclean surface and penetrating the casing from the clean surface to the unclean surface; and a plurality of power transmission portions, each having a part located inside a corresponding guide portion of the plurality of guide portions and movable along the corresponding guide portion, wherein each of the plurality of power transmission portions is: disposed between a drive portion, which is provided in the power unit and linearly moves, and a driven portion, which is provided in the surgical tool in a direction different from a linear motion direction of the drive portion and intersects the linear motion direction; and configured to transmit a movement of the drive portion to the driven portion, the plurality of guide portions extend in the linear motion direction of the drive portion, and the driven portion is configured to move along a path not intersecting an extended line of a path along which the drive portion linearly moves.

2. The motive power transmission adapter according to claim 1, wherein an unclean-side engagement portion capable of engaging with or being disengaged from the drive portion and capable of transmitting a linear motion of the drive portion is provided in a region of each of the plurality of power transmission portions facing the drive portion, and a clean-side engagement portion capable of engaging with or being disengaged from the driven portion and capable of transmitting a movement of each of the plurality of power transmission portions to the driven portion is provided in a region of the each power transmission portion facing the driven portion.

3. The motive power transmission adapter according to claim 1, wherein the motive power transmission adapter is configured such that the surgical tool is attachable to and removable from the motive power transmission adapter so as to face the clean surface, and the power unit is attachable to and removable from the motive power transmission adapter so as to face the unclean surface.

4. The motive power transmission adapter according to claim 1, wherein the casing is formed in a plate shape extending along the clean surface and the unclean surface and extending in the linear motion direction of the drive portion, and the plurality of power transmission portions are disposed in the casing and are disposed to be arranged in the direction intersecting the linear motion direction of the drive portion.

5. The motive power transmission adapter according to claim 1, wherein the casing is formed in a tubular shape extending in the linear motion direction of the drive portion, an outer peripheral surface of the casing on which the power unit is disposed forms the unclean surface, and an inner peripheral surface of the casing inside on which the surgical tool is disposed forms the clean surface, and the plurality of power transmission portions each comprise a part to be disposed on the outer peripheral surface of the casing and are disposed to be arranged in the direction intersecting the linear motion direction of the drive portion.

6. The motive power transmission adapter according to claim 1, wherein the casing comprises a first regulation portion configured to abut against at least one of the surgical tool and the power unit and to regulate a relative movement direction between at least abutting one of the surgical tool and the power unit and the casing in the linear motion direction of the drive portion.

7. The motive power transmission adapter according to claim 1, wherein each of the plurality of power transmission portions comprises a first driven abutment surface configured to abut against a driven engagement portion of the driven portion when the surgical tool moves relative to the casing along the linear motion direction and engages with the casing.

8. The motive power transmission adapter according to claim 7, wherein an unclean-side engagement portion capable of engaging with or being disengaged from the drive portion and capable of transmitting a linear motion of the drive portion is provided in a region of each of the plurality of power transmission portions facing the drive portion, a clean-side engagement portion capable of engaging with or being disengaged from the driven portion and capable of transmitting a movement of each of the plurality of power transmission portions to the driven portion is provided in a region of each power transmission portion facing the driven portion, each of the plurality of power transmission portions comprises a first driven holding portion, and the first driven holding portion is formed to have a length in the direction intersecting the linear motion direction with respect to the first driven abutment surface and is configured to regulate a relative movement in the linear motion direction between the driven engagement portion of the driven portion which moves relative to the first driven abutment surface in the intersection direction and the clean-side engagement portion.

9. The motive power transmission adapter according to claim 1, wherein each of the plurality of power transmission portions comprises a first drive abutment surface which abuts against a drive engagement portion of the drive portion when the power unit moves relative to the casing along the linear motion direction and engages with the casing.

10. The motive power transmission adapter according to claim 9, wherein an unclean-side engagement portion capable of engaging with or being disengaged from the drive portion and capable of transmitting a linear motion of the drive portion is provided in a region of each of the plurality of power transmission portions facing the drive portion, a clean-side engagement portion capable of engaging with or being disengaged from the driven portion and capable of transmitting a movement of each of the plurality of power transmission portions to the driven portion is provided in a region of each power transmission portion facing the driven portion, each of the plurality of power transmission portions comprises a first drive holding portion, and the first drive holding portion is formed to have a length in the direction intersecting the linear motion direction with respect to the first drive abutment surface and is configured to regulate a relative movement in the linear motion direction between the drive engagement portion of the drive portion which moves relative to the first drive abutment surface in the intersection direction and the unclean-side engagement portion.

11. The motive power transmission adapter according to claim 1, wherein
each of the plurality of power transmission portions comprises a first engagement convex portion configured to engage with at least one of the drive portion and the driven portion and a first elastic portion configured to be elastically deformed by a force applied to the first engagement convex portion.

12. The motive power transmission adapter according to claim 11, wherein
each of the plurality of power transmission portions comprises a first detection unit configured to detect a movement of the first engagement convex portion by elastic deformation of the first elastic portion.

13. The motive power transmission adapter according to claim 11, wherein
the first engagement convex portion comprises an inclined surface in which a cross-sectional area of the first engagement convex portion increases from a distal end of the first engagement convex portion toward a root thereof.

14. The motive power transmission adapter according to claim 11, wherein
each of the plurality of power transmission portions comprises a first engagement concave portion configured to engage with at least one of a convex portion provided in the drive portion and a convex portion provided in the driven portion, and
the first engagement concave portion comprises an inclined surface in which an opening area of the first engagement concave portion increases from a bottom surface toward an opening.

15. A medical manipulator system comprising:
a power unit disposed in an unclean region and having at least one drive portion driven in a linear motion direction;
the motive power transmission adapter according to claim 1; and
a surgical tool disposed in a clean region and having at least one driven portion which receives a transmission of a driving force from the plurality of power transmission portions and is driven.

16. The medical manipulator system according to claim 15, wherein
at least one of the power unit and the surgical tool comprises a second regulation portion configured to abut against the casing and regulate a relative movement direction of the abutted casing in a linear motion direction of at least one drive portion.

17. The medical manipulator system according to claim 15, wherein
the at least one drive portion comprises a second drive abutment surface configured to abut against a transmission engagement portion of the plurality of power transmission portions when the power unit moves relative to the casing along the linear motion direction and engages with the casing.

18. The medical manipulator system according to claim 17, wherein
the at least one drive portion comprises a second drive holding portion formed to have a length in the direction intersecting the linear motion direction with respect to the second drive abutment surface and configured to regulate a relative movement in the linear motion direction between the transmission engagement portion which moves relative to the second drive abutment surface in the intersection direction and the at least one drive portion.

19. The medical manipulator system according to claim 15, wherein
the at least one driven portion comprises a second driven abutment surface which abuts against a transmission engagement portion of the plurality of power transmission portions when the surgical tool moves relative to the casing along the linear motion direction and engages with the casing.

20. The medical manipulator system according to claim 19, wherein
the at least one driven portion comprises a second driven holding portion formed to have a length in the direction intersecting the linear motion direction with respect to the second driven abutment surface and configured to regulate a relative movement in the linear motion direction between the transmission engagement portion which moves relative to the second driven abutment surface in the intersection direction and the at least one driven portion.

21. The medical manipulator system according to claim 15, wherein
at least one of the at least one drive portion and the at least one driven portion comprises a second engagement convex portion configured to engage with the plurality of power transmission portions and a second elastic portion configured to be elastically deformed by a force applied to the second engagement convex portion.

22. The medical manipulator system according to claim 21, wherein
at least one of the at least one drive portion and the at least one driven portion comprises a second detection unit configured to detect a movement of the second engagement convex portion by elastic deformation of the second elastic portion.

23. The medical manipulator system according to claim 21, wherein
the second engagement convex portion comprises an inclined surface in which a cross-sectional area of the second engagement convex portion increases from a distal end of the second engagement convex portion toward a root thereof.

24. The medical manipulator system according to claim 21, wherein
at least one of the at least one drive portion and the at least one driven portion comprises a second engagement concave portion configured to engage with a convex portion provided in the plurality of power transmission portions, and
the second engagement concave portion comprises an inclined surface in which an opening area of the second engagement concave portion increases from a bottom surface toward an opening.

25. The medical manipulator system according to claim 15, wherein
the at least one drive portion is a plurality of drive portions,
the power unit comprises the plurality of drive portions, and a plurality of actuator units configured to push the plurality of drive portions in a pushing direction along linear motion directions of the plurality of drive portions and to pull the plurality of drive portions in a pulling direction,
the at least one driven portion is a plurality of driven portions, the surgical tool comprises the plurality of driven portions corresponding to the plurality of drive portions, and in a case where the plurality of driven portions are moved by the plurality of drive portions, one of the drive portions is moved in one of the pushing direction and the pulling direction by corresponding one of the actuator units so as to move one driven portion and at least one of the other drive portions is biased in one of the pushing direction and the pulling direction by corresponding at least one of the actuator units.

* * * * *